(12) United States Patent
Gerson et al.

(10) Patent No.: US 8,324,282 B2
(45) Date of Patent: *Dec. 4, 2012

(54) ALKYLATING AGENT COMBINATIONS IN THE TREATMENT OF CANCER

(75) Inventors: Stanton L. Gerson, Hunting Valley, OH (US); Lili Liu, Northfield, OH (US)

(73) Assignee: Case Western Reserve University, Cleveland, OH (US)

( * ) Notice: Subject to any disclaimer, the term of this patent is extended or adjusted under 35 U.S.C. 154(b) by 942 days.

This patent is subject to a terminal disclaimer.

(21) Appl. No.: 10/505,400

(22) PCT Filed: Feb. 19, 2003

(86) PCT No.: PCT/US03/05032
§ 371 (c)(1),
(2), (4) Date: Jun. 22, 2005

(87) PCT Pub. No.: WO03/070234
PCT Pub. Date: Aug. 28, 2003

(65) Prior Publication Data
US 2006/0241186 A1    Oct. 26, 2006

Related U.S. Application Data

(63) Continuation-in-part of application No. 10/079,049, filed on Feb. 19, 2002, now Pat. No. 6,635,677, which is a continuation-in-part of application No. 09/373,693, filed on Aug. 13, 1999, now Pat. No. 6,465,488.

(51) Int. Cl.
*A61K 31/13* (2006.01)
*A61K 31/33* (2006.01)

(52) U.S. Cl. .......... 514/645; 514/589; 514/274; 514/33; 514/50; 514/34; 514/23

(58) Field of Classification Search .................. 514/645, 514/589, 274, 33, 50, 34, 23
See application file for complete search history.

(56) References Cited

U.S. PATENT DOCUMENTS

| 4,325,950 | A | * | 4/1982 | Cramer | 514/186 |
| 4,978,332 | A | * | 12/1990 | Luck et al. | 604/19 |
| 5,731,304 | A |   | 3/1998 | Baer et al. |  |
| 6,465,448 | B1 | * | 10/2002 | Gerson et al. | 514/183 |
| 6,635,677 | B2 | * | 10/2003 | Gerson et al. | 514/645 |

FOREIGN PATENT DOCUMENTS

| JP | 10045589 | 2/1998 |
| WO | WO 94/15615 | 7/1994 |
| WO | WO 9415615 A1 * | 7/1994 |

OTHER PUBLICATIONS

Scharer, O.D., et al., "A Designed Inhibitor of Base-Excision DNA Repair", J. Am. Chem. Soc., 117, 10781-10782, (1995).*
Griffin et al (Biochemie (1995) 77, 408-422.*
Suggitt and Bibby, Clinical Cancer Research, 2005, vol. 11, 971-981.*
Fortini et al (Carcinogenesis vol. 13 No. 1 (1992) pp. 87-93).*
Rosa et al (Nucleic Acids Research, vol. 19, No. 20 (1991) 5569-5574).*
Boulton et al (British J of Cancer (295) 72 849-856).*
Boulton et al, (British Journal of Cancer (1995) 72, 849-856).*
Ahnen. Colon Cancer Prevention by NSAIDs: What is the Mechanism of Action? Eur. J. Surg. 582, 111-114 (1998).
Bianchi et al. O6-methylguanine-DNA Methyltransferase Activity and Induction of Novel Immunogenicity in Murine Tumor Cells Treated with Methyhylating Agents. Cancer Chemother. Pharmacol. 29, 277-282 (1992).
Boulton et al. Potentiation of temozolomide-induced cytotoxicity: a comparative study of the biological effects of poly (ADP-ribose) polymerase inhibitors. Br. J. Cancer 72, 849-856 (1995).
Branch et al. Defective mismatch binding ad a mutator phenotype in cells tolerant to DNA damage. Nature 362, 652-654 (1993).
Buschfort et al. DNA excision repair profiles of normal and leukemic human lymphocytes: functional analysis at the single-cell level. Cancer Res. 57, 651-658 (1997).
Caldecott et al. XRCC1 polypeptide interacts with DNA polymerase-beta and possibly poly (ADP-ribose) polymerase, and DNA ligase III is a novel molecular 'nick-sensor' in vitro. Nucleic Acids Res. 24, 4387-4394 (1996).
Chou and Talalay. "Quantitative analysis of dose-effect relationship: the combined effects of multiple drugs on enzyme inhibitors," in Advances in Enzyme Regulation, G. Weber, ed. New York: Pergamon Press, p. 27-55 (1983).
Choy et al. Concurrent Paclitaxel, Carboplatin, and Radiation Therapy for Locally Advanced Non-small Cell Lung Cancer. Seminars in Oncology 26, Suppl. 2: 36-43 (1999).
Claij et al. Microsatellite Instability in Human Cancer: A Prognostic Marker for Chemotherapy? Exper. Cell Res. 246, 1-10 (1999).
Coquerelle et al. Overexpression of N-methylpurine-DNA glycosylase in Chinese hamster ovary cells renders them more sensitive to the production of chromosomal aberrations by methylating agents: a case of imbalanced DNA repair. Mutation Res. 336, 9-17 (1995).
De Murcia, J.M. et al. Requirement of poly (ADP-ribose) polymerase in recovery from DNA damage in mice and in cells. PNAS 94, 7303-7304 (1997).
Engelward et al. Repair-deficient 3-methyladenine DNA glycosylase homozygous mutant mouse cells have increased sensitivity to alkylation-induced chromosome damage and cell killing. EMBO J. 15, 945-952 (1996).
Fink et al. The role of DNA mismatch repair in drug resistance. Clin. Cancer Res. 4, 1-6 (1998).
Gonzaga et al. Identification of the cross-link between human O6-methylguanine-DNA methyltransferase and chloroethlnitrosourea-treated DNA. Cancer Res. 52, 6052-6058 (1992).

(Continued)

*Primary Examiner* — Benjamin Packard
(74) *Attorney, Agent, or Firm* — Tarolli, Sundheim, Covell & Tummino LLP

(57) ABSTRACT

This application provides compositions and methods useful in the treatment of certain cancers. In part, this application is based on the recognition that certain molecules that target abasic lesions or AP sites in DNA improve, augment, or potentiate the chemotherapeutic efficacy of certain anticancer agents.

12 Claims, 24 Drawing Sheets

OTHER PUBLICATIONS

Griffin et al. DNA mismatch binding and incision at modified guanine bases by extracts of mammalian cells: implications for tolerance to DNA methylation damage. Biochemistry 33, 4787-4793 (1994).

Gunderson. Indications for and Results of Combined Modality Treatment of Colorectal Cancer. Acta Oncologica 38, 7-21 (1999).

Hainsworth et al. The Current Role and Future Prospects of Paclitaxel in the Treatment of Small Cell Lung Cancer. Seminars in Oncology 26, Suppl. 2: 60-66 (1999).

Kaina et al. Chromosomal instability, reproductive cell death and apoptosis induced by O6-methylguanine in Mex−, Mex+ and methylation-tolerant mismatch repair compromised cells: facts and models. Mutation Res. 381, 227-241 (1997).

Karran and Bignami. DNA damage tolerance, mismatch repair and genome instability. BioEssays 16, 833-839 (1994).

Kat et al. An alkylation-tolerant, mutator human cell line is deficient in strand-specific mismatch repair. PNAS 90, 6424-6428 (1993).

Kerr et al. Novel therapeutic strategies for colorectal cancer. Hosp. Med. 59, 617-621 (1998).

Kingma and Osheroff. Apurinic sties are position-specific topoisomerase II poisons. J. Biol. Chem. 272, 11413-1155 (1997).

Lazebnik et al. Cleavage of poly(ADP-ribose) polymerase by a proteinase with properties like ICE. Nature 371, 346-347 (1994).

Lindahl et al. Post-translation modification of poly(AD-P-ribose) polymerase induced DNA strand breaks. Trends Biochem. Scil 20, 405-411 (1995).

Link et al. Basic research supported developments of chemotherapy in nonresectable isolated colorectal liver metastases to a protocol of hepatic artery infusion using mitoxantrone, 5-FU + folinic acid and mitomycin C. Gan To Kagaku Ryoho 26, 269-281 (1999).

Liu et al. Mismatch repair mutations override alkyltransferase in conferring resistance to temozolomide by not to 1,3-bis(2-chloroethyl)nitrosourea. Cancer Res. 56, 5375-5379 (1996).

Liu, L. et al. Clin. Cancer Res. 5, 2908-2917 (1999).

Liu, L. et al. Methoxyamine Mediated Inhibition of Base Excision Repair (BER) Significantly Enhances Temozolomide Antitumor Effect in Mismatch Repair (MMR) Proficient and Deficient Colon Cancer Xenografts. Proc. Am. Assoc. Cancer Res. 41, 98 (Mar. 2000).

Malapetsa et al. Identification of a 116 kDa protein able to bind 1,3-bis (2-chloroethyl)-1-nitrosourea-damaged DNA as poly (ADP-ribose) polymerase: Mutation Res. 362, 41-50 (1996).

Matijasevic et al. Protection against chloroethylnitrosourea cytotoxicity by eukaryotic 3-methyladenine DNA glycosylase. PNAS 90, 11855-11859 (1993).

Midgley et al. Colorectal Cancer. Lancet 353, 391-399 (1999).

Mitchell and Dolan. Effect of temozolomide and dacarbazine on O6-alkylguanine-DNA alkyltransferase activity and sensitivity of human tumor cells and xenografts to 1,3-bis(2-chloroethyl)-1-nitrosourea. Cancer Chemother. Pharmacol. 32, 59-63 (1993).

Molinete et al. Over production of the poly (ADP-ribose) polymerase beta. Mutation Res. 407, 203-215 (1998).

Morris et al. Flow cytometric evaluation of cell-cycle progression in ethyl methanesulfonate and methyl methanesulfonate-exposed P3 cells: relationship to the induction of sister-chromatid exchanges and cellular toxicity. Environ. Mol. Mutagen. 18, 139-149 (1991).

Neddermann et al. Cloning and Expression of Human G/T Mismatch-specific Thymine-DNA Glycosylase. J. Biol. Chem. 271, 12767-12774 (1996).

Neijt et al. Paclitaxel/Carboplatin for the Initial Treatment of Advanced Ovarian Cancer. Seminars in Oncology 26, Suppl. 2: 78-83 (1999).

O'Connor et al. Isolation and structure of a cDNA expressing a mammalian 3-methyladenine-DNA glycosylase. EMBO J. 9, 3337-3342 (1990).

Olsen et al. Molecular cloning of human uracil-DNA glycosylase, a highly conserved DNA repair enzyme. EMBO J. 8, 3121-3125 (1989).

Pegg et al. Structure, function and inhibition of O6-alkylguanine-DNA AGT. Prog. Nucleic Acid Res. Mol. Biol. 51, 167-233 (1995).

Pera et al. Exceptional sensitivity of testicular germ cell tumour cell lines to the new anti-cancer agent, tomozolomide. Br. J. Cancer 71, 904-906 (1995).

Perez. Paclitaxel Plus Nonanthracycline Combinations in Metastatic Breast Cancer. Seminars in Oncology 26, Suppl. 2, 21-26 (1999).

Prakash and Gibson. Sequence-selective depurination, DNA interstrand cross-linking and DNA strand break formation associated with alkylated DNA. Carcinogenesis 13, 425-431 (1992).

Radicella et al. Cloning and characterization of hOOG1, a human homolog of the OGG1 gene of *Saccharomyces cerevisiae*. PNAS 94, 8010-8015 (1997).

Robertson et al. Down-regulation of apurinic/apyrimidinic endonuclease expression is associated with the induction of apoptosis in differentiating myeloid leukemia cells. Cell Growth and Differentiation 8, 443-449 (1997).

Rosenquist et al. Cloning and characterization of a mammalian 8-oxoguanine DNA glycosylase. PNAS 94, 7429-7434 (1997).

Samson et al. Cloning and characterization of a 3-methyladenine DNA glycosylase cDNA from human cells whose gene maps to chromosome 16. PNAS 88, 9127-9131 (1991).

Sobol et al. Requirement of mammalian DNA polymerase-beta in base-excision repair. Nature 379, 183-186 (1996).

Taverna, P. et al. Methoxyamine (MX) Potentiates DNA Single Strand and Double Strand Breaks Induced by Temozolomide (TMZ) in Colon Cancer Cells. Proc. Am. Assoc. Cancer Res. 41, 265 (Mar. 2000).

Tentori et al. Role of Wild-Type p53 on the Antineoplastic Activity of Temozolomide Alone or Combined with Inhibitors of Poly(ADP-Ribose) Polymerase. J. Pharmacol. Exp. Ther. 285, 884-893 (1998).

Tentori, L. et al. Cytotoxic and clastogenic effects of a DNA minor groove binding methyl sulfonate ester in mismatch repair deficient leukemia cells. Leukemia 14, 1451-1459 (2000).

Thomale et al. Haematol. Blood Transfus. 39, 3-12 (1998).

Vollberg et al. Isolation and characterization of the human uracil DNA glycosylase gene. PNAS 86, 8693-8697 (1989).

Von Hoff. Promising New Agents for Treatment of Patients with Colorectal Cancer. Seminars in Oncology 25, Suppl 11: 47-52 (1998).

Walker et al. A role for the human DNA repair enzyme HAP1 in cellular protection against DNA damaging agents and hypoxic stress. Nucleic Acids Res. 22, 4884-4889 (1994).

Wedge et al. 3-Aminobenzamide and/or O6-benzylguanine evaluated as an adjuvant to temozolomide or BCNU treatment in cell lines of variable mismatch repair status and O6-alkylguanine-DNA alkyltransferase activity. Br. J. Cancer 74, 1030-1036 (1996).

Wedge et al. In vitro evaluation of temozolomide combined with X-irradiation. Anti-Cancer Drugs 8, 92-97 (1997).

Wedge et al. Effect of single and multiple administration of an O6-benzylguanine/temozotomide combination: an evaluation in a human melenoma xenograft model. Cancer Chemother. Pharmacol. 40, 266-272 (1997).

Wilson et al. Life without DNA repair. PNAS 94, 12754-12757 (1997).

Wilson. Mammalian base excision repair and DNA polymerase beta. Mutation Res. 407, 203-215 (1998).

Fortini et al., "Mutagenic processing of esthylation damage in mammalian cells: the use of methoxyamine to study apurinic/apyrimidinic site-induced mutagenesis," Cancer Res. 53:1149-1155 (1993).

Fortini et al., Methoxyamine modification of abasic sites protects CHO cells from the cytotoxic and mutagenic effects of oxygen alkylation, Carcinogenesis 13: 87-93 (1992).

Liuzzi and Talpeart-Borle, "A new approach to the study of the base-excision repair pathway using methoxyamine," J. Biol. Chem. 260:5252-5258 (1985).

Menissier-de Murcia et al., "Requirement of poly (ADP—ribose) polymerase in recovery from DNA damage in mice and in cells," Proc. Natl. Acad. Sci. USA 94:7303-7304 (1997).

Rosa et al., "Processing in vitro of an abasic site reacted with methoxyamine: a new assay for the detection of abasic sites formed in vivo," Nucleic Acids Res. 19:5569-5574 (1991).

* cited by examiner

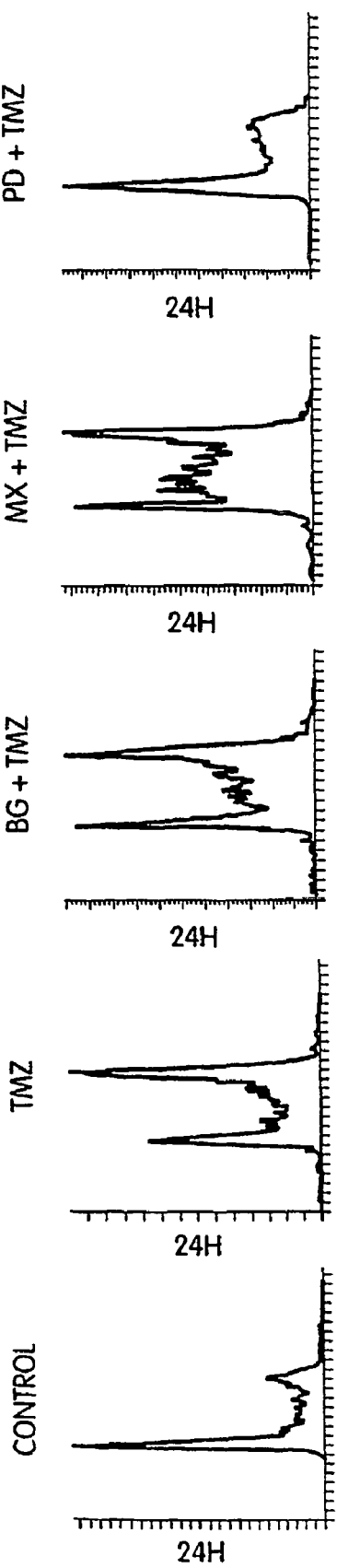
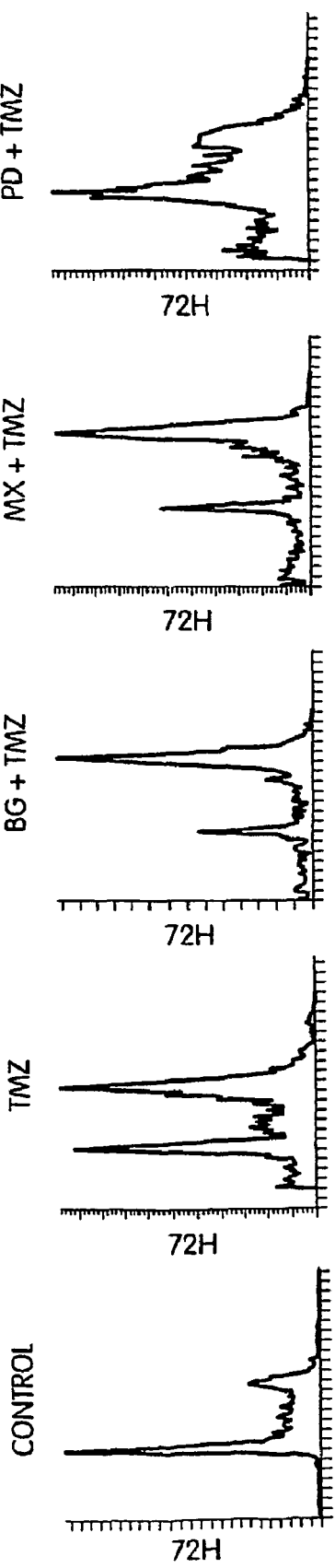

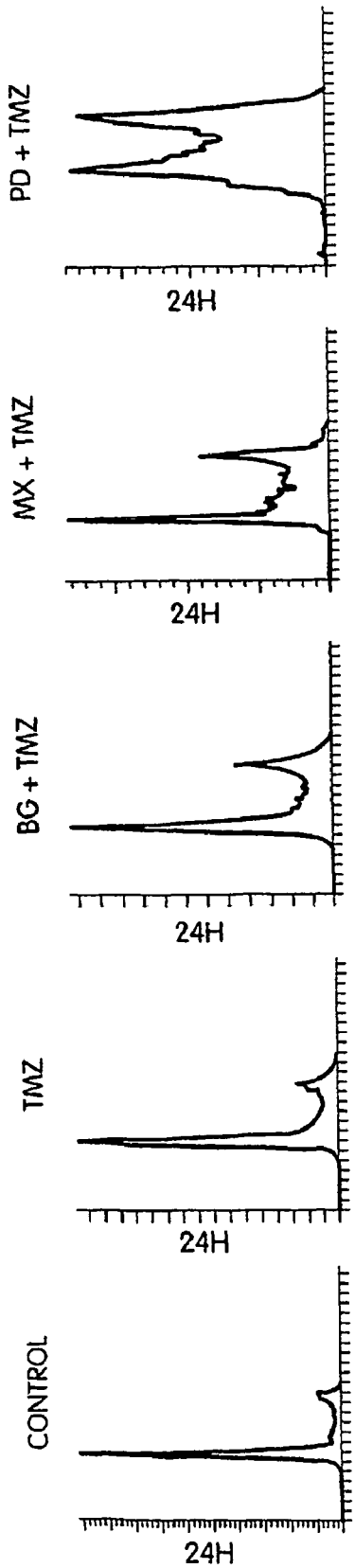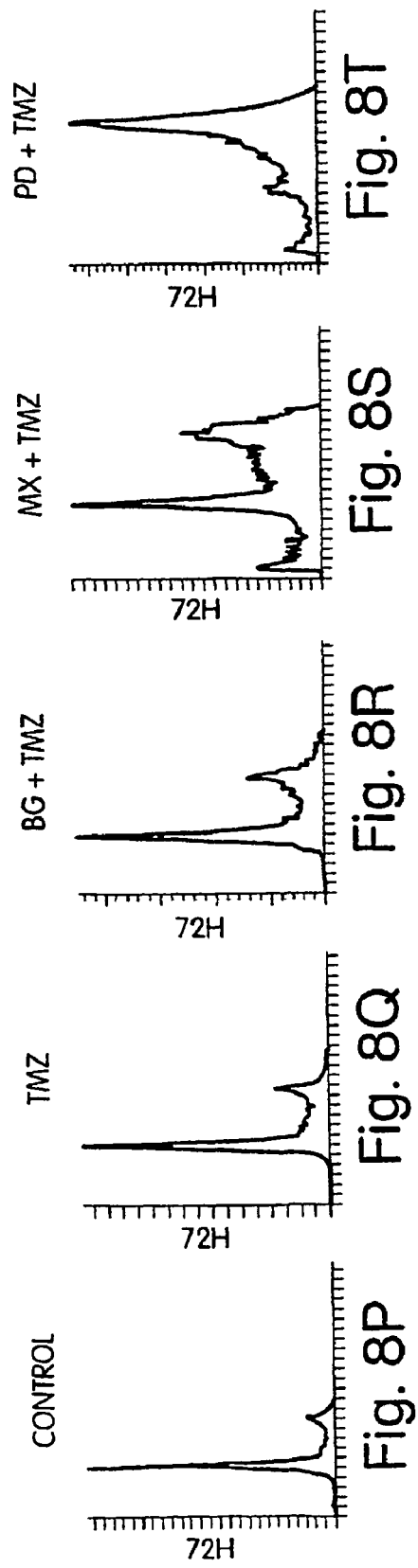

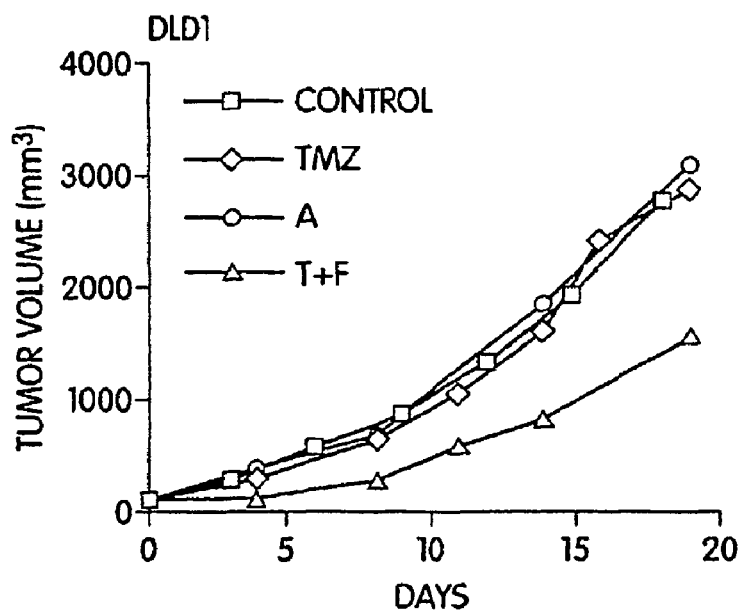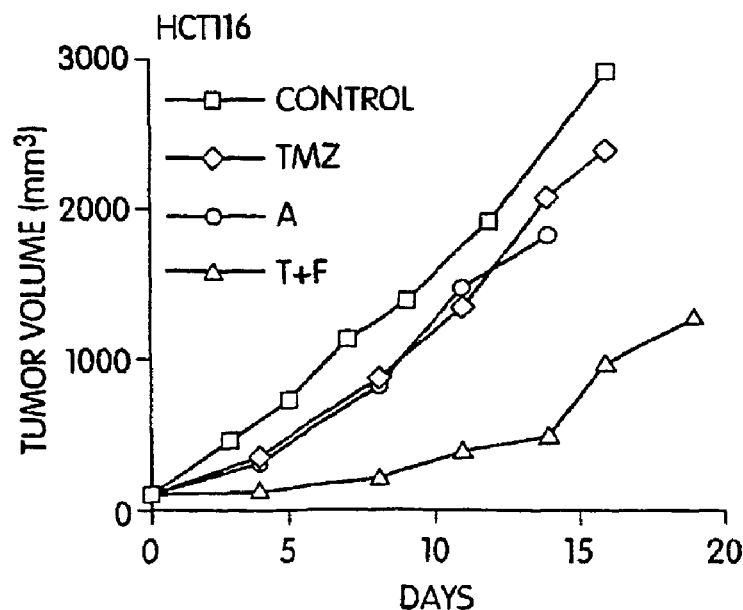
Fig. 16

*SW480 AND HCT116 CELLS WERE TREATED WITH ETOPOSIDE (5mM) FOR 4 HRS

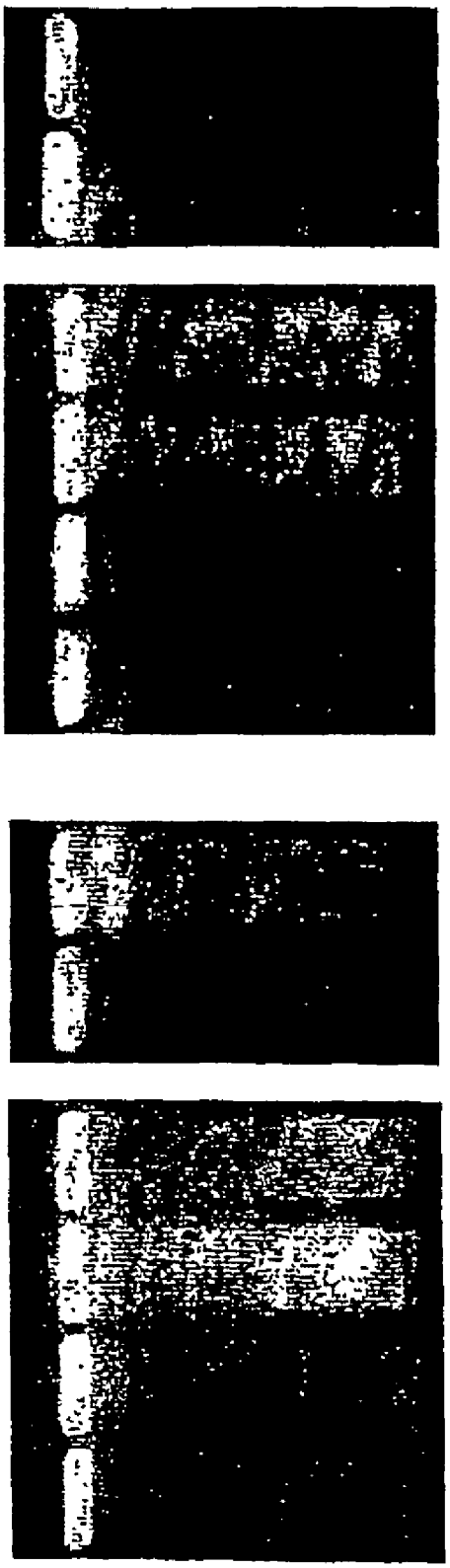

ALKYLATING AGENT COMBINATIONS IN THE TREATMENT OF CANCER

RELATED APPLICATIONS

This application claims priority from PCT/US2003/05032, filed Feb. 19, 2003, which is a continuation-in-part of 10/079,049, filed Feb. 19, 2002, now U.S. Pat. No. 6,635,677, which is a continuation-in-part of U.S. Pat. No. 09/373,693, filed Aug. 13, 1999, now U.S. Pat. No. 6,465,488.

This invention was made in part with government support under grants RO1CA73062, RO1ES06288, U01CA75525 and P30CA43703 from the USPHS, and grant NIH-CA-86357 as well as a RAID initiative through the NCI as NSC3801. The government has certain rights in the invention.

FIELD OF THE INVENTION

This invention generally relates to novel compositions and methods for the treatment of certain cancers. Additionally, this invention relates to novel compositions and methods to screen drugs useful for the treatment of certain cancers.

BACKGROUND

Cancer is a worldwide problem. The American Cancer Society estimates that over one half million people will die from cancer in the United States alone in 1999. As such, finding novel compositions and methods for the treatment of cancer is of vital interest. The treatment of cancer falls into three general categories: chemotherapy, radiation therapy and surgery. Often, therapies are combined since a combination of therapies often increases the probability the cancer will be eradicated as compared to treatment strategies utilizing a single therapy. Most typically, the surgical excision of large tumor masses is followed by chemotherapy and/or radiation therapy.

Chemotherapeutic agents can work in a number of ways. For example, chemotherapeutic can work by interfering with cell cycle progression or by generating DNA strand breaks. If the cancer cell is not able to overcome the cell cycle blockage or cell injury caused by the therapeutic compound, the cell will often die via apoptotic mechanisms. The use of a single chemotherapeutic agent in the treatment of cancer, with or without surgery or radiation, has several disadvantages. First, the cells may develop resistance to the chemotherapeutic agent. Such resistance results either in the requirement for higher dosages of the drug and/or the renewed spread of the cancer. Chemotherapeutic agents can be toxic to the patient. Therefore, there is a practical upper limit to the amount that a patient can receive. However, if two chemotherapeutic agents are used in concert, the dosage of any single drug can be lowered. This is beneficial to the patient since using lower levels of chemotherapeutic agents is generally safer for the patient. Additionally, cancer cells are less likely to generate resistance to the combination of drugs as they are to a single drug.

The design of drug combinations for the chemotherapeutic treatment of cancer should be approached with the goals of 1) finding a combination that is synergistic with and not merely additive to the first compound with respect to the elimination of the tumor, and 2) finding a second drug that does not potentiate the toxic effects of the first chemotherapeutic agent. These conditions require a great deal of empirical testing of agents known to have anticancer properties with agents that either may have anticancer properties, or that may augment the first agent in other ways. TMZ is currently employed in chemotherapeutic treatment of certain tumors. It works by dramatically increasing the mutation rate of cells undergoing DNA replication. Such cells, because of the high number of mutations which they have acquired as a result of the treatment with TMZ, are rapidly removed by apoptosis, thereby potentially eliminating the tumor. Some tumor cells are resistant to treatment by TMZ due to deficiencies in the mismatch repair (MMR) system in the cell. A defective MMR system prevents the cell from recognizing $O^6$ mG DNA adducts thereby making the cell resistant to elimination.

Baer et al., in U.S. Pat. No. 5,731,304, note that the toxicity of temozolomide can be potentiated by agents that inhibit the enzyme $O^6$-alkylguanine DNA alkyltransferase (ATase). In particular, they note that $O^6$-benzylguanine (BG) can enhance the toxicity of temozolomide in certain cell lines that exhibit high levels of ATase (e.g. 300-fold in MAWI cells). However, in other cell lines that exhibit lower levels of ATase (e.g. U373 cells) the effect is significantly less.

Mitchell and Dolan (*Cancer Chemother Pharmocol* 32:59-63, 1993) note that temozolomide (TMZ) and an analogue, 5-(dimethyltriazeno)imidazole-4-caroxamide (DITC), can be effective in enhancing the anti-tumor effects of 1,3-bis(2-chloroethyl) 1-nitrosourea (BCNU). TMZ and DITC work by depleting cells or tumors of $O^6$-alkylguanine-DNA alkytransferase (AGT). AGT is a DNA repair protein that selectively removes adducts from the $0^6$ position of guanine in DNA by a stoichiometric transfer of the alkyl group to a cysteine moiety. Removal of the alkyl group from the DNA by methylation of the $0^6$ position of the guanine effectively inactivates the AGT. As with the patent referred to above, the disclosed method is limited to specific cells or cancers.

Therefore, what is needed are therapies that utilize the synergistic properties of two or more therapeutic agents for the treatment of cancer that have a broader range of targets or a different range of targets than those combination therapies already known.

SUMMARY OF THE INVENTION

This application provides compositions and methods useful in the treatment of certain cancers. In part, this application is based on the recognition that certain molecules that target abasic lesions or AP sites in DNA improve, augment, or potentiate the chemotherapeutic efficacy of certain anticancer agents.

The present invention relates generally to compositions and methods for the treatment of hyperproliferation, such as cancer, that utilize both a chemotherapeutic that induces the formation of AP sites in the DNA of a cell and an inhibitor of the base excision repair pathway (BER pathway). In preferred embodiments, the BER inhibitor is methoxyamine or compound A.

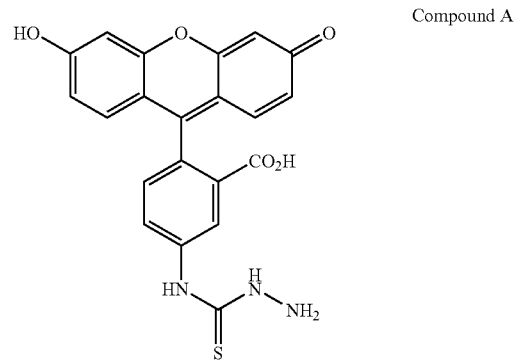

Compound A

In one embodiment, this application provides methods for enhancing the therapeutic effect of an anticancer agent, such as, for example, an anticancer agent that induces the formation of AP sites, by administering a base excision repair (BER) inhibitor, whereby the BER inhibitor enhances the effect of the anticancer agent. The BER inhibitor may be administered either prior to the administration of the anticancer agent or at the same time. It may be administered either orally or intravenously.

The certain embodiments, the BER inhibitor may be any one of an AP endonuclease inhibitor, a DNA glycosylase inhibitor, a DNA polymerase inhibitor, a PARP inhibitor, a DNA alkyltransferase inhibitor, and a DNA ligase inhibitor.

In one aspect, the AP endonuclease inhibitor may be anyone of methoxyamine, compound A, and N-ethylmaleimide. In other aspects, the BER inhibitor is a PARP inhibitor selected from PD128763, 3-AB, 6-AN, NU1025, and 4-amino-1,8-naphthalimide. In another aspect the BER inhibitor is an inhibitor of DNA polymerase, such as DNA polymerase $\beta$, $\gamma$, or $\epsilon$. The DNA polymerase inhibitor may be selected from prunasin; aphidicolin; ddCTP; ddTTP; ddATP; ddGTP; Ara-C; and arabinocytidine.

In yet other aspects, the BER inhibitor is a DNA ligase inhibitor that inhibits the action of DNA ligase I or DNA ligase II. In other embodiments, the BER inhibitor is a DNA glycosylase inhibitor.

In certain aspects of the invention, the anticancer agent is an agent that induces the formation of AP sites and may be selected from any one of the following agents: a DNA oxidizing agent; ultraviolet radiation; a DNA intercalating agent; a radiosensitizing agent; a cross-linking agent; and an alkylating agent.

In certain embodiments, examples of the alkylating agents include TMZ (temozolomide); $MeOSO_2(CH_2)_2$-lexitropsin (Me-Lex); Cis-diamminedichloroplatinum II (cis-DDP); mitomycin bioreductive alkylating agents; quinones; STZ (streptozotocin); cyclophosphamide; nitrogen mustard family members such as chloroambucil; pentostatin (purine analogs); fludarabine; bendamustine hydrochloride which is the active ingredient of Ribomustin (alkylating group in common with the nitrogen mustard family, also an antimetabolites); chloroethylating nitrosoureas (lomustine, fotemustine, cystemustine); dacarbazine (DTIC); and procarbazine.

In other aspects, the anticancer agent is a DNA oxidizing agent and the DNA oxidizing agent may be any one of the following: hydrogen peroxide, bleomycin, and adriamycin. In yet other aspects, the agents that induce the formation of AP sites include ultraviolet radiation, gamma irradiation, UVA, UVB, and radiosensitizing agent. Examples of radiosensitizing agents include agents such as IUdR.

In yet other aspects, agents that induce the formation of AP sites include cross-linking agents such as BCNU; intercalating agents such as bleomycin; adriamycin; quinacrine; echinomycin; and anthrapyrazoles. In other embodiments, the anticancer agent may be any one of uracil; hypoxanthine; 5-FU; flavonoids; ecteinascidin-743; cis-diamminedichloroplatinum II; 6-thioguanine; taxol; and camptothecin analogs.

The formulations and compositions disclosed herein may be useful in the treatment of cancers such as carcinomas, melanomas, sarcomas, lymphomas, leukemias, astrocytomas, gliomas, malignant melanomas, chronic lymphocytic leukemia, lung cancers, and breast cancers.

In yet another embodiment, the application provides kits comprising: 1) a first pharmaceutical preparation comprising an anticancer agent that induces formation of AP sites; and 2) a second pharmaceutical preparation comprising a base excision repair inhibitor, and instructions for administering the first and second pharmaceutical preparations to a patient for the treatment of cancer.

In certain embodiments, the invention contemplates that anticancer agents such as temozolomide (TMZ) may be used together with BER inhibitors such as methoxyamine (MX) as a treatment for certain tumors that are resistant to treatment by the anticancer agent alone. Additionally, the invention contemplates that anticancer agents such as TMZ and inhibitors of poly-ADP-ribose polymerase (PARP) may be used as a treatment for certain tumors that are resistant to treatment by the anticancer agent alone. The present invention generally comprises novel compositions to 1) screen for compounds that can potentiate or modulate the therapeutic effect of anticancer agents such as temozolomide (TMZ), either alone or combined with methoxyamine (MX), 2) provide model systems for the study of cancer treatments by agents that modulate DNA repair mechanisms and 3) provide treatments for certain hyperproliferative disorders such as cancers.

With regard to the treatment of cancer, the present invention contemplates methods of treating cancer that utilize an anticancer agent such as TMZ in conjunction with another agent that is capable of potentiating the toxic effect of the anticancer agent. More specifically, the invention relates to potentiating the effect of anticancer agents such as TMZ with agents that modify DNA adducts created by the anticancer agent. Even more specifically, the invention relates to potentiating the effect of anticancer agents such as TMZ with agents that interact with AP sites and/or modify $N^7$-methylguanine ($N^7$ mG) and $N^3$-methyladenine ($N^3$ mA) DNA adducts. Examples of such agents are MX and compound A. The present invention is not limited by the order in which the agents are administered. In one embodiment, the agents are administered sequentially. In another embodiment, the agents are administered as a combined formulation (e.g., a formulation comprising methoxyamine and temozolomide). In one embodiment, the present invention contemplates a method of treating cancer by administering to a patient diagnosed with cancer a first formulation comprising a BER inhibitor such as methoxyamine and a second formulation comprising an anticancer agent such as temozolomide. In certain alternative embodiments, the anticancer agent and the BER inhibitor are administered to the patient in a single formulation.

Additionally, the invention relates to potentiating anticancer agents such as temozolomide with agents that interfere with the ability of PARP to be effective in DNA repair by either competing with PARP, inhibiting PARP, or degrading PARP. The present invention is not limited to the agent used to inhibit PARP activity. In one embodiment, PD128763 is used. In another embodiment 6-AN is used. In another embodiment, 3-AB is used. The present invention is not limited by the order in which the agents are administered. In one embodiment the agents are administered sequentially. In another embodiment, the agents are administered as a combined formulation. In one embodiment, the present invention contemplates a method of treating cancer by administering to a patient diagnosed with cancer a first formulation comprising a poly-(ADP-ribose)-polymerase inhibitor and a second formulation comprising an anticancer agent such as temozolomide. In certain alternative embodiments, the inhibitor and the agent are administered to the patient in a single formulation.

The present invention is not limited to the method of administration of the treatment. In one embodiment, the treatment is administered orally. In another embodiment the treatment is administered intravenously. In yet another embodiment, the treatment is administered intraperitoneally. In yet another embodiment, the treatment is administered directly to the tumor by injection or, in the case of skin tumors, for example, by direct application of creams or ointments. In certain embodiments, one agent is administered by one route, while the second agent is administered by a second route (e.g., temozolomide is administered orally, while the BER inhibitor is administered by injection).

As noted above, the present invention also contemplates screening assays to identify drugs that augment the ability of anticancer agents such as temozolomide to inhibit tumor growth, drugs that augment the ability of temozolomide with methoxyamine to inhibit tumor growth, and drugs that augment the ability of temozolomide with PARP inhibitors to inhibit tumor growth. A variety of assay formats are contemplated for testing the potential of compounds suspected of augmenting the anti-tumor effect of anticancer agents such as TMZ. In one embodiment, cells are pretreated with the test compound that may augment the antitumor effect of the agent, followed by treatment with the anticancer agent. Cell growth and/or cell death are then measured to determine if there is an anti-tumor effect. In another embodiment, cells are treated with the test compound that may augment the anti-tumor effect of the agent at approximately the same time as they are treated with the anticancer agent. Cell growth and/or cell death are then measured to determine if the regime had an anti-tumor effect. The invention is not limited to any particular measurement technique for apoptosis or cell growth. Various methods are envisioned. For example, mitosis can be measured by use of fluorescent dyes that intercalate into DNA, by the measurement of $^3$H-thymidine incorporation, or by colormetric assays. Such assays permit the use of high-throughput screening methods. Apoptosis can be measured by the use of fluorescent dyes that intercalate into DNA, annexin-V staining of phosphotidyl serine residues of the cell surface or morphological changes in cell appearance.

The present invention contemplates a method of screening for compounds that augment the anti-tumor effect of an anticancer agent such as temozolomide by contacting tumor cells (e.g., in vitro, or optionally in vivo) with a first formulation comprising a test compound that may potentiate the anticancer agent and a second formulation comprising the anticancer agent and measuring the growth and death rates of said cells to determine whether the test compound potentiates the activity of the anticancer agent.

The present invention contemplates a method of screening for compounds that augment the anti-tumor effect of an anticancer agent such as temozolomide by implanting tumor cells in an animal, and administering to the animal a first formulation comprising a test compound that may potentiate an anticancer agent such as temozolomide and a second formulation comprising the anticancer agent, and measuring the growth and death rates of said cancer cells to determine whether the test compounds potentiates the anticancer agent.

It is not intended that the present invention be limited by the nature of the compounds to be screened in the screening assay of the present invention. For example, a variety of compounds including peptides, organic compounds, and inorganic compounds, are contemplated. Additionally, combinations of compounds are contemplated by the present invention.

In some embodiments, a method is provided in which a patient diagnosed with cancer is administered a dose of a first formulation comprising a BER inhibitor such as methoxyamine and a dose of a second formulation comprising an anticancer agent such as 1,3-bis (chloroethyl) 2-nitrosourea (BCNU), wherein said inhibitor is administered in an amount sufficient to potentiate toxicity of said agent. In some embodiments, the inhibitor and agent are administered sequentially, while in other embodiments the inhibitor and agent are administered in a single formulation. In some embodiments, said the inhibitor and agent are administered orally, while in other embodiments, said the inhibitor and agent are administered intravenously. In yet other embodiments, a formulation comprising both the inhibitor and agent is contemplated.

In other embodiments, a method is provided comprising administering to a patient diagnosed with cancer a first formulation comprising a BER inhibitor such as methoxyamine and a second formulation comprising an anticancer drug or agent that exerts cytotoxicity mediated by oxidative DNA damage, wherein said BER inhibitor is administered in an amount sufficient to potentiate toxicity of said anticancer agent or drug. In some embodiments, said anticancer drug or agent is selected from bleomycin and adriamycin. In some embodiments, said inhibitor and said anticancer drug or agent are administered sequentially. In other embodiments, said inhibitor and said anticancer drug or agent are administered as a formulation.

In other embodiments, a method is provided comprising administering to a patient diagnosed with cancer a first formulation comprising a BER inhibitor such as methoxyamine and a second formulation comprising an anticancer drug or agent selected from hypoxanthine, 5-FU, uracil, IUdR, bleomycin and adriamycin, wherein said inhibitor is administered in an amount sufficient to potentiate toxicity of said anticancer drug or agent. In some embodiments, said inhibitor and said anticancer drug or agent are administered sequentially, while in other embodiments, said inhibitor and said anticancer drug or agent are administered in a single formulation. In some embodiments, said administration is oral administration, in other embodiments, said administration is intravenous administration.

In some embodiments, a formulation comprising a BER inhibitor such as methoxyamine and an anticancer drug or agent selected from hypoxanthine, 5-FU, uracil, IUdR, bleomycin and adriamycin is contemplated. In some embodiments, said anticancer drug or agent is BAR. In some embodiments, a formulation comprising methoxyamine and hydrogen peroxide is contemplated.

In some embodiments, a method is provided comprising administering to a patient diagnosed with cancer a formulation comprising a BER inhibitor such as methoxyamine and treating said patient with radiation; wherein said inhibitor is administered in an amount sufficient to potentiate the toxicity of said radiation. In some embodiments, said inhibitor administration and radiation treatment occur sequentially, while in other embodiments, said inhibitor administration occurs essentially simultaneously with said radiation treatment.

In some embodiments, a method is provided comprising administering to a patient diagnosed with cancer a first formulation comprising a BER inhibitor such as methoxyamine and a second formulation comprising a DNA oxidizing agent such as hydrogen peroxide, wherein said inhibitor is administered in an amount sufficient to potentiate the cytotoxic effects of said oxidizing agent.

In other embodiments, a method is provided comprising administering to a patient diagnosed with cancer a first formulation comprising a BER inhibitor such as methoxyamine and a second formulation comprising an antineoplastic agent such as iododeoxyuridine (IUdR), wherein said methoxyamine is administered in an amount sufficient to further increase the radiosensitivity of the tumor cells in said patient. In some embodiments, the method further comprises treating said patient with radiation therapy. In some embodiments, said the inhibitor and agent are administered sequentially, while in other embodiments, they are administered as a formulation. In some embodiments, the inhibitor and agent are administered orally, while in other embodiments, said they are administered intravenously.

In certain embodiments, the compositions and methods of the invention are used to treat a patient having a cancer selected from carcinomas, melanomas, sarcomas, lymphomas, leukemias, astrocytomas, gliomas, malignant melanomas, chronic lymphocytic leukemia, lung cancers, and breast cancers.

DESCRIPTION OF THE FIGURES

FIG. 8. Distribution of cell cycle and apoptosis in colon cancer cell lines after treatment with TMZ plus modifiers. A. MMR wt SW480 cells; B. MMR-deficient HCT116 cells.

FIG. 16 shows enhanced inhibition of tumor growth by TMZ and compound A in nude mice.

FIG. 20 shows DNA double strand breaks (DSBs) induced by the combination of TMZ, MX, and etoposide, at 4 hours and 72 hours after treatment, respectively.

DEFINITIONS

Figure 1A:
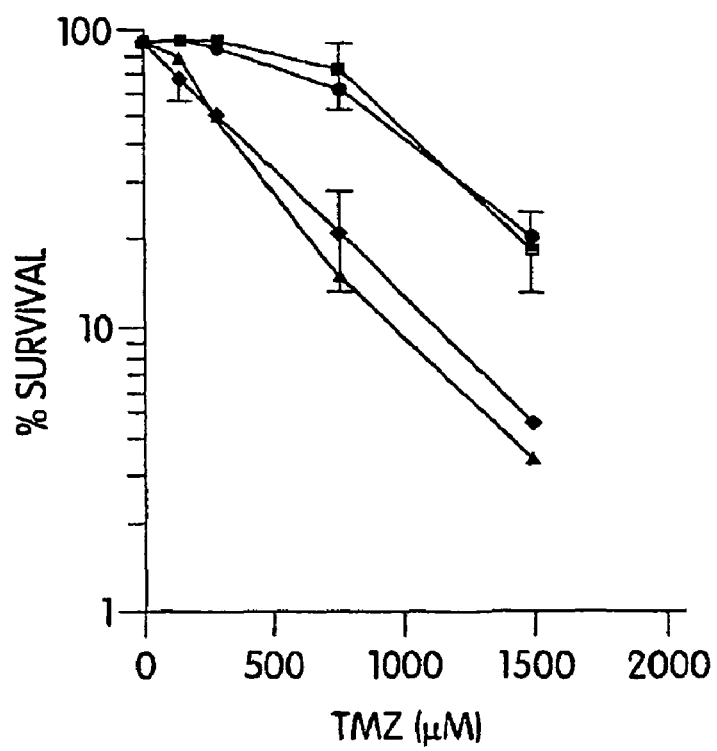
FIG. 1. MX increases the sensitivity of colon cancer cells to TMZ. Cells were treated with 0-1500 µM TMZ for 2 h or TMZ and 6 mM MX or plus 10 µM BG for 2 h prior to 2 h exposure to TMZ. A. HTC116 cells; B. SW480 cells. (■), TMZ alone; (♦), MX plus TMZ; (●), BG plus TMZ; (▲), BG and MX plus TMZ. Results are the mean±SD of at least three separate experiments performed in duplicate.

To facilitate understanding of the invention, a number of terms are defined below.

As used herein "agent" or "drug" is used herein to denote a chemical compound, a mixture of chemical compounds, a biological macromolecule, or an extract made from biological materials such as bacteria, plants, fungi, or animal particularly mammalian) cells or tissues that are suspected of having therapeutic properties. The agent or drug may be purified, substantially purified or partially purified.

As used herein "agonist" refers to molecules or compounds which mimic the action of a "native" or "natural" compound. Agonists may be homologous to these natural compounds in respect to conformation, charge or other characteristics. Thus, agonists may be recognized by, e.g., receptors expressed on cell surfaces. This recognition may result in physiologic and/or biochemical changes within the cell, such that the cell reacts to the presence of the agonist in the same manner as if the natural compound was present.

As used herein "antagonist" refers to molecules or compounds which inhibit the action of a "native" or "natural" compound. Antagonists may or may not be homologous to these natural compounds in respect to conformation, charge or other characteristics. Thus, antagonists may be recognized by the same or different receptors or molecules that are recognized by an agonist. Antagonists may have allosteric effects which prevent the action of an agonist (e.g., by modifying a DNA adduct, or antagonists may prevent the function of the agonist (e.g., by blocking a DNA repair molecule).

As used herein, the term "fusion protein" refers to a chimeric protein containing the protein of interest joined to an exogenous protein fragment. The fusion partner may provide a detectable moiety, may provide an affinity tag to allow purification of the recombinant fusion protein from the host cell, or both. If desired, the fusion protein may be removed from the protein of interest by a variety of enzymatic or chemical means known to the art.

As used herein, the term "purified" or "to purify" refers to the removal of one or more contaminants from a sample. The present invention contemplates purified compositions (discussed above).

As used herein, the term "partially purified" refers to the removal of a moderate portion of the contaminants of a sample to the extent that the substance of interest is recognizable by techniques known to those skilled in the art as accounting for a measurable amount of the mixture. Preferably, the compound of interest is at least 5% of the total preparation and up to 50% of the total preparation.

As used herein, the term "substantially purified" refers to the removal of a significant portion of the contaminants of a sample to the extent that the substance of interest is recognizable by techniques known to those skilled in the art as the most abundant substance in the mixture.

As used herein the term "portion" when in reference to a protein (as in "a portion of a given protein") refers to fragments of that protein. The fragments may range in size from four amino acid residues to the entire amino acid sequence minus one amino acid. In one embodiment, the present invention contemplates "functional portions" of a protein. Such portions are "functional" if they contain a binding region (i.e., a region having affinity for another molecule) and such binding can take place (i.e., the binding region functions, albeit with perhaps lower affinity than that observed for the full-length protein). Such "functional portions" of the gene product are typically greater than 10 amino acids in length, and more typically greater than 50 amino acids in length, and even more typically greater than 100 amino acids in length. "Functional portions" may also be "conserved portions" of the protein. The alignment of the various gene products permit one skilled in the art to select conserved portions of the protein (i.e., those portions in common between two or more species) as well as unconserved portions (i.e., those portions unique to two or more species). In one embodiment, the present invention contemplates conserved portions 10 amino acids in length or greater, and more typically greater than 50 amino acids in length.

"Staining" shall be defined as any number of processes known to those in the field that are used to better visualize, distinguish or identify a specific component(s) and/or feature(s) of a cell or cells.

"Immunofluorescence" is a staining technique used to identify, mark, label, visualize or make readily apparent by procedures known to those practiced in the art, where a ligand (usually an antibody) is bound to a receptor (usually an antigen) and such ligand, if an antibody, is conjugated to a fluorescent molecule, or the ligand is then bound by an antibody specific for the ligand, and said antibody is conjugated to a fluorescent molecule, where said fluorescent molecule can be visualized with the appropriate instrument (e.g., a fluorescent microscope).

"Antibody" shall be defined as a glycoprotein produced by B cells that binds with high specificity to the agent (usually, but not always, a peptide), or a structurally similar agent, that generated its production. Antibodies may be produced by any of the known methodologies [Current Protocols in Immunology (1998) John Wiley and Sons, Inc., N.Y.] and may be either polyclonal or monoclonal.

"In operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

"Antigen" shall be defined as a protein, glycoprotein, lipoprotein, lipid or other substance that is reactive with an antibody specific for a portion of the molecule.

"Morphology" shall be defined as the visual appearance of a cell or organism when viewed with the eye, a light microscope, a confocal microscope or an electron microscope, as appropriate.

"Patient" shall be defined as a human or other animal, such as farm animals or laboratory animals (e.g., guinea pig or mice) capable of having cell cycle (influenced) determined diseases, either naturally occurring or induced, including but not limited to cancer.

A "wild type" (wt) cell or cell line shall be defined as a cell or cell line that retains the characteristics normally associated with that type of cell or cell line for the physiological process or morphological characteristic that is being examined. It is permissible for the cell or cell line to have non-wild type characteristics for physiological process or morphological characteristics that are not being examined as long as they do not appreciably affect the process or characteristic being examined.

DESCRIPTION OF THE INVENTION

This invention generally relates to novel compositions and methods for the treatment of certain cancers. Additionally, this invention relates to novel compositions and methods to screen drugs useful for the treatment of certain cancers.

Injury to DNA is minimized by enzymes that recognize errors, remove them, and replace the damaged DNA with corrected nucleotides. DNA damage occurs when a single-strand break is introduced, a base is removed leaving its former partner unpaired, a base is covalently modified, a base is converted into another that is not appropriately paired with the partner base, or a covalent link is introduced between bases on opposite strands. Excision repair systems remove the mispaired or damaged base from the DNA strand and then synthesize new DNA to replace it. Base excision repair (BER) is initiated during replication of DNA and allows for correction of damaged bases/mispaired bases prior to completion of replication.

Base excision repair is initiated by a DNA glycosylase that removes N-glycosidic (base-sugar) bonds, liberating the damaged base and generating an abasic site (AP site). An apurinic or apyrimidinic site results from the loss of a purine or pyrimidine residue, respectively, from DNA. uracil residues result from the spontaneous deamination of cytosine and can lead to a C→T transition if unrepaired. There is also a glycosylase that recognizes and excises hypoxanthine, the deamination product of adenine. Other glycosylases remove alkylated bases (such as 3-methyladenine, 3-methylguanine, and 7-methylguanine), ring-opened purines, oxidatively damaged bases, and in some organisms, UV photodimers.

The AP site is further processed by a 5'-3' endonuclease (AP endonuclease (APE)) that incises the phosphodiester bond on both sides of the damaged purine or pyrimidine base. The AP endonucleases introduce chain breaks by cleaving the phosphodiester bonds at the AP sites.

PARP aids in processing of DNA strand breaks induced during MMR and BER. PARP is a DNA nick surveillance protein that binds weakly to BER intermediates when single-nucleotide BER proceeds normally to completion. In contrast, when single nucleotide BER is stalled by a block in the excision step, PARP binds strongly to the BER intermediate, along with AP endonuclease (APE), DNA pol β, and FEN-1.

In mammalian cells, the 5'-deoxyribose sugar phosphate is removed by the intrinsic AP lyase (dRP) activity of DNA polymerase β (pol β). DNA polymerase enzyme also fills the gaps with new nucleotides.

Finally, DNA ligase covalently links the 3' end of the new material to the old material. Thus, the wild-type sequence is restored.

Topoisomerases I and II are also involved in DNA repair, as they recognize spontaneous AP sites and form stable cleavable complexes. Topoisomerase II inhibitors promote DNA cleavage and other chromosomal aberrations, including sister chromatid exchanges.

Thus, compounds useful as BER inhibitors include AP endonuclease inhibitors such as methoxyamine (MX), N-ethylmaleimide, O$^6$-benzylguanine, and compounds having structures of formula I:

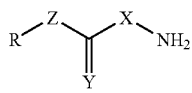

Formula I wherein
X is O or NH,
Y is O, S, or NH,
Z is absent or represents O, S, or NH, and
R represents a hydrogen or a hydrocarbon moiety,
and pharmaceutically acceptable salts thereof.

In single-nucleotide BER, the deoxyribose phosphate (dRP) in the abasic site is removed by the lyase activity of DNA pol β. Compounds such as methoxyamine react with the aldehyde of an abasic site, making it refractory to the β-elimination step of the dRP lyase mechanism, thus blocking single-nucleotide BER. Suitable AP endonuclease inhibitors may act by binding to AP sites and preventing APE-mediated cleavage of phosphodiester bonds, or by acting directly on AP endonuclease. Other compounds that may possess AP endonuclease inhibitory activity (e.g., by binding to AP sites and preventing APE-mediated cleavage of phosphodiester bonds) include Other potential inhibitors include O-benzylohydroxylamine; ethyl aminooxyacetate; aminooxyacetic acid; ethyl aminooxyacetate; $H_2NOCHMeCO_2H$; carboxymethoxyamine; aminooxyacetic acid; $HN=C(NH_2)SCH_2CH_2ONH_2$; $H_2NO(CH_2)_3SC(NH_2)=NH$; $MeOC(O)CH(NH_2)CH_2ONH_2$; $H_2NOCH_2CH(NH_2)CO_2H$; canaline; $H_2NO(CH_2)_4ONH_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; $H_2C=CHCH_2ONH_2$; $H_2NO(CH_2)_4ONH_2$; $H_3C-(CH_2)_{15}-O-NH_2$, 2,2'-(1,2-ethanediyl)bis(3-aminooxy)butenedioic acid dimethyl diethyl ester; compounds having any of the following structures:

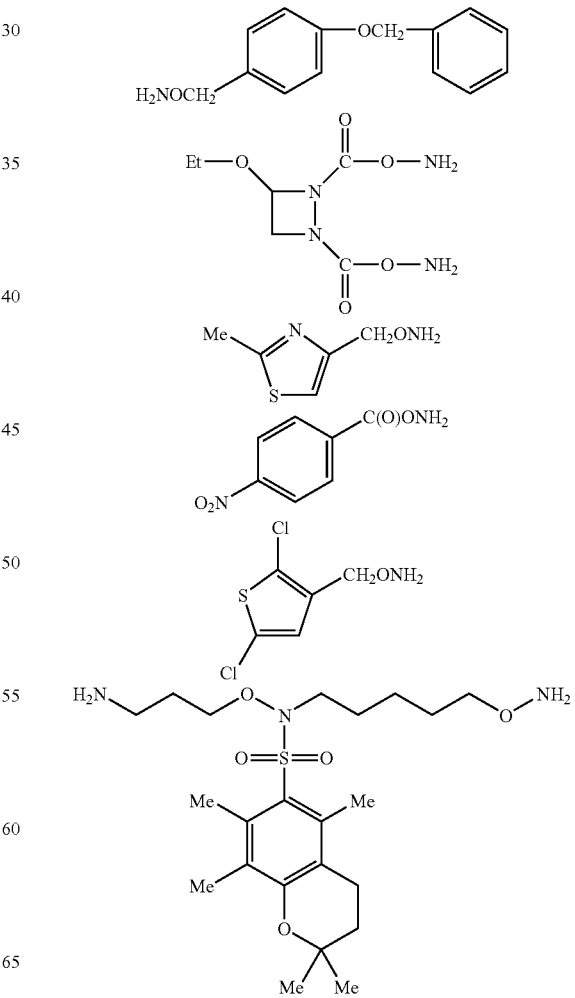

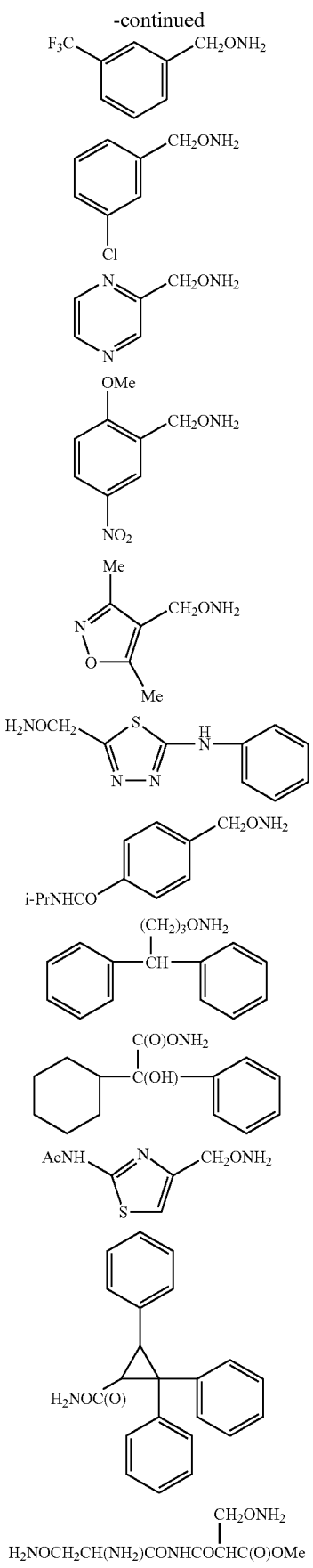

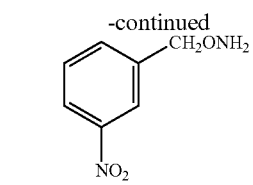

and pharmaceutically acceptable salts of any of these compounds.

Compounds useful as BER inhibitors include PARP inhibitors, such as 4-amino-1,8-naphthalimide (ANI), PD128763, 3-AB, 6-AN, and 8-hydroxy-2-methyl-quinazolin-4-[3H] one (NU-1025).

Compounds useful as BER inhibitors include DNA polymerase inhibitors (e.g., DNA polymerase β, γ, or ε), such as prunasin, aphidicolin, 2',3'-dideoxycytidine triphosphate (ddCTP), 2',3'-dideoxythymidine triphosphate (ddTTP), 2',3'-dideoxyadenosine triphosphate (ddATP), 2',3'-dideoxyguanosine triphosphate (ddGTP), 1-beta-D-arabinofuranosylcytosine (Ara-C), caffeine, arabinocytidine, and bleomycin.

Compounds useful as BER inhibitors include DNA ligase inhibitors (e.g., DNA ligase I, II, or III), such as ursolic and oleanolic acids, aleuritolic acid, protolichesterinic acid, swertifrancheside, fulvoplumierin, fagaronine chloride, and bleomycin. XRCC1 is the protein partner of DNA ligase III, and inhibitors of XRCC1, such as 3-AB, are useful as BER inhibitors as well.

Topoisomerase II inhibitors induce DNA cleavage and other chromosomal aberrations, including sister chromatid exchanges. Compounds useful as BER inhibitors also include topoisomerase II inhibitors, such as etoposide (VP-16, VP-16-123), meso-4,4'-(2,3-butanediyl)-bis-(2,6-piperazinedione) (ICRF-193, a bisdioxopiperazine), doxorubicin (DOX), amsacrine (4',9-acridinylaminomethanesulfon-m-anisidide; mAMSA), pazelliptine, nalidixic acid, oxolinic acid, novobiocin, coumermycin A1, fostriecin, teniposide, mitoxantrone, daunorubicin, N-[2-dimethylamino)ethyl] acridine-4-carboxamide (DACA), merbarone, quinacrine, ellipticines, epipodophyllotoxins, ethidium bromide, epirubicin, pirarubicin, 3'-deamino-3'-morpholino-13-deoxo-10-hydroxy carminomycin; 2",3"-bis pentafluorophenoxyacetyl-4',6'-ethylidene-beta-D glucoside of 4'-phosphate-4'-dimethylepipodophyollotoxin 2N-methyl glucamine salt (F11782; a fluorinated lipophilic epipodophylloid), adriamycin, actinomycin D, anthracyclines (such as 9-aminoanthracycline), and pyrazoloacridine (PZA). Topoisomerase I inhibitors, such as camptothecin and topotecan can also be used as BER inhibitors.

Other inhibitors of these enzymes, whether known in the art or hereafter identified, as well as inhibitors of other elements of the BER pathway, such as DNA alkyltransferase, may be employed in the compositions and methods of the invention without departing from the scope and spirit of the present invention.

In certain embodiments, the present invention contemplates the use of 1) a topoisomerase inhibitor, preferably a topoisomerase II inhibitor such as etoposide, 2) an anticancer agent that induces the formation of AP sites (such as temozolomide), and 3) a BER inhibitor (other than a topoisomerase inhibitor), such as methoxyamine.

Anticancer agents that induce the formation of AP sites include intercalating agents such as bleomycin, adriamycin, quinacrine, echinomycin (a quinoxaline antibiotic), and anthrapyrazoles.

Radiation, such as gamma radiation, UVA, and UVB, can be used to generate AP sites according to the methods of the invention. Ultraviolet light is absorbed in DNA with the formation of UV-specific di-pyrimidine photoproducts. Exposure to gamma irradiation, UVA, and UVB can induce damaged pyrimidine photodimers Anticancer agents that induce the formation of AP sites include DNA oxidizing agents such as hydrogen peroxide.

Anticancer agents that induce the formation of AP sites include alkylating agents such as temozolomide (TMZ), 1,3-bis(2-chloroethyl)-1-nitrosourea (BCNU), MeOSO$_2$(CH$_2$)$_2$-lexitropsin (Me-Lex), cis-diamminedichloroplatinum II (cisplat; cis-DDP), mitomycin bioreductive alkylating agents, quinones, streptozotocin, cyclophosphamide, nitrogen mustard family members such as chloroambucil, pentostatin (and related purine analogs), fludarabine, bendamustine hydrochloride, chloroethylating nitrosoureas (e.g., lomustine, fotemustine, cystemustine), dacarbazine (DTIC), and procarbazine. In certain embodiments, the alkylating agent is a nitrosoruea such as a mustine, i.e., a compound having a structure of Formula II, wherein R is an optionally substituted hydrocarbon substituent, such as an alkyl, cycloalkyl, heterocyclyl, aryl, heteroaryl, cycloalkylalkyl, heterocyclylalkyl, aralkyl, or a heteroaralkyl:

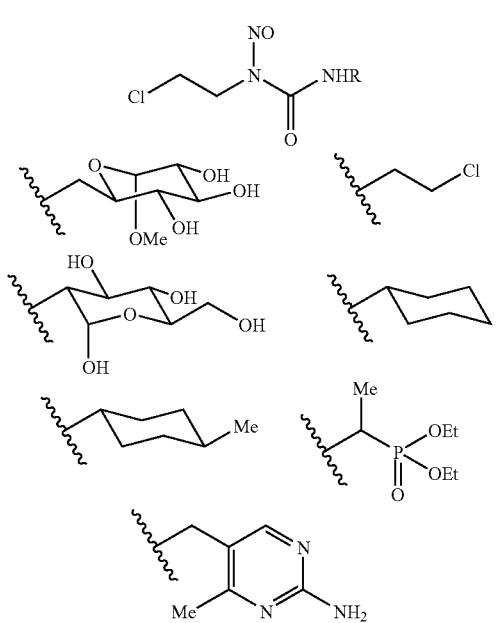

II

In preferred embodiments, R is a substituent shown below or to the right of Formula I, i.e., the chemotherapeutic is carmustine (BCNU), chlorozotocin, fotemustine, lomustine, nimustine, ranimustine, or semustine. In certain related embodiments, the chloroethyl group of Formula I is replaced by a methyl group, as in streptozocin. In certain embodiments, however, R is not 2-chloroethyl, i.e., the compound is not BCNU.

Alkylating agents can function by adding methyl groups to DNA, cross-linking macromolecules essential for cell division, and linking guanine bases in DNA through their N$^7$ atoms. Both inter- and intra-strand cross-links can be mediated by alkylating agents. Inter-strand cross-links prevent the separation of the DNA strands necessary for cell division, and by being more difficult to repair, constitute the more lethal lesion.

In certain embodiments, the anticancer agent is selected from radiosensitizers such as 5-iodo-2'-deoxyuridine (IUdR), 5-fluorouracil (5-FU), 6-thioguanine, hypoxanthine, uracil, ecteinascidin-743, and camptothecin and analogs thereof.

In certain embodiments, the anticancer agent is not temozolomide. In certain embodiments, the anticancer agent is not BCNU. In certain embodiments, the anticancer agent is not PE128723, 6-AN, 3-AB, BCNU, or temozolomide.

Throughout the specification, any recitation of a particular compound should be understood to encompass that compound and any (other) pharmaceutically acceptable salts thereof.

In DNA repair competent cells, DNA adducts formed by methylating agents may be efficiently repaired or may be sites of both mutagenic and cytotoxic damage. In this process, the cellular response is specific for each of the DNA adducts formed. Perhaps the best studied is the response to O$^6$-methylguanine (O$^6$ mG). This adduct may be repaired in a single step reaction by O$^6$-alkylguanine-DNA alkyltransferase (AGT), however, saturation of this protein by an excess of adducts or inhibition by O$^6$-benzylguanine (BG) results in residual adducts which are both cytotoxic and mutagenic (Pegg et al. "Structure, function and inhibition of O$^6$-alkylguanine-DNA AGT" *Prog. Nucleic Acid Res. Mol. Biol.* 51:167-233, 1995.). Cytotoxicity results from recognition of this adduct by components of the mismatch repair (MMR) system, a 5- or 6-protein complex which recognizes O$^6$ mG: thymine base pairs formed by DNA replication past O$^6$ mG, and excises thymine and surrounding bases, resulting in DNA strand breaks. However, a thymine is preferentially reincorporated opposite the persisting O$^6$ mG, triggering MMR function again. It has been hypothesized that this repetitive aberrant repair process increases DNA double strand breaks and acts as a trigger of apoptosis (Fink et al. "The role of DNA mismatch repair in drug resistance" *Clin. Cancer Res.* 4:1-6, 1998.).

MMR deficiency results in inability to process the O$^6$ mG:T mispair. Consequently, cells replicate DNA past O$^6$ mG lesions without cell cycle arrest, chromosomal aberrations, or apoptosis and therefore survive in the face of persistent DNA damage (Branch et al. "Defective mismatch binding and a mutator phenotype in cells tolerant to DNA damage" *Nature* 362:652-654, 1993; Kat et al. "An alkylation-tolerant, mutator human cell line is deficient in strand-specific mismatch repair" *Proc. Natl. Acad. Sci., USA* 90:6424-6428, 1993; Karran and Bignami "DNA damage tolerance, mismatch repair and genome instability" *Bioessays* 16:833-839, 1994; Griffin et al. "DNA mismatch binding and incision at modified guanine bases by extracts of mammalian cells: implications for tolerance to DNA methylation damage" *Biochemistry* 33:47874793, 11994; Liu et al. "Mismatch repair mutations override alkyltransferase in conferring resistance to temozolomide but not to 1,3-bis(2-chloroethyl)nitrosourea" *Cancer Res.* 56:5375-5379, 1996). The presence of MMR deficiency in a number of colon cancer cell lines allowed the present inventors the opportunity to evaluate the relative contribution of this DNA repair defect in resistance to the methylating chemotherapeutic agent, temozolomide (TMZ), where we found that MMR deficiency resulted in 35-60 fold resistance to TMZ in cells defective in either MLH1 or GTBP even after inhibition of AGT by BG (Liu et al. "Mismatch repair mutations override alkyltransferase in conferring resistance to temozolomide by not to 1,3-bis(2-chloroethyl)nitrosourea" *Cancer Res.* 56:5375-5379, 1996).

While O$^6$ mG is the best studied cytotoxic DNA adduct, it is not the most abundant. TMZ, like other methylating agents, also forms N$^7$-methylguanine (N$^7$ mG) and N$^3$-methyladenine ($N^3$ mA) DNA adducts at frequencies 11 and 1.5 times that of $O^6$ mG. These DNA adducts are efficiently removed by base excision repair (BER) and appear to contribute little to cytotoxicity. In the first step of BER, a series of glycosylases recognize abnormal bases such as $N^3$ mA and $N^7$ mG (O'Connor et al. "Isolation and structure of a cDNA expressing a mammalian 3-methyladenine-DNA glycosylase" *EMBO J.* 9:3337-3342, 1990; Samson et al. "Cloning and characterization of a 3-methyladenine DNA glycosylase cDNA from human cells whose gene maps to chromosome 16" *Proc. Natl. Acad. Sci. USA* 88:9127-9131, 1991), the T:G mismatch (Neddermann et al. "Functional expression of soluble human interleukin-11 (IL-11) receptor alpha and stoichiometry of in vitro IL-11 receptor complexes with gp130" *J. Biol. Chem.* 271:12767-12774, 1996), and deaminated bases such as hypoxanthine/oxidized 8-oxo-7,8-dihydroguanine or uracil:A (Vollberg et al. "Isolation and characterization of the human uracil DNA glycosylase gene" *Proc. Natl. Acad. Sci. USA* 86: 8693-8697, 1989; Olsen et al. "Molecular cloning of human uracil-DNA glycosylase, a highly conserved DNA repair enzyme" *EMBO J.* 8:3121-3125, 1989; Radicella et al. "Cloning and characterization of hOGG1, a human homolog of the OGG1 gene of *Saccharomyces cerevisiae*" *Proc. Natl. Acad. Sci.* USA 94.8010-8015, 1997; Rosenquist et al. "Cloning and characterization of a mammalian 8-oxoguanine DNA glycosylase" *Proc. Natl. Acad. Sci.* USA 94:7429-7434, 1997). Following enzymatic or spontaneous hydrolysis of the N-glycosidic bond and release of the abnormal base, AP (apurinic/apyrimidinic) endonuclease hydrolyzes the phosphodiester backbone 5' to the lesion and dRpase (a DNA deoxyribophosphodiesterase and its activity is associated with polymerase β) excises the residual dRp, generating a gap of one nucleotide. DNA polymerase β fills the gap and DNA ligase seals the nick. This pathway is called short-patch BER. An alternative pathway for BER involves DNA synthesis to fill a gap of 2 to 13 nucleotides. This long patch repair requires proliferating cell nuclear antigen (PCNA) and PCNA-dependent DNA polymerase (Willson "Mammalian base excision repair and DNA polymerase beta" *Mutation Res.* 407:203-215, 1998).

Poly-(ADP-ribose)-polymerise (PARP) acts as a nick sensor of DNA strand breaks by itself or interaction with XRCC1 and involves in BER. PARP binds damaged DNA, resulting in autoribosylation. The modified protein then releases and allows other proteins to access and repair DNA strand breaks (Willson "Mammalian base excision repair and DNA polymerase beta" *Mutation Res.* 407:203-215, 1998; Molinete et al. "Over production of the poly (ADP-ribose) polymerase DNA-binding domain blocks alkylation-induced DNA repair synthesis in mammalian cells" *EMBO J.* 12:2109-2117, 1993; Caldecott et al. "XRCCI polypeptide interacts with DNA polymerase β and possibly poly (ADP-ribose) polymerise, and DNA ligase III is a novel molecular 'nick-sensor' in vitro" *Nucleic Acids Res.* 24:4387-4394, 1996). Therefore, PARP participates in BER after nick formation in both short patch and long patch repair. It appears most active in the alternative (long patch repair) pathway for BER.

BER as a therapeutic target to increase the cytotoxicity of methylating agents has been documented. Cells deficient in DNA polymerase B or blocked in expression of AP endonuclease by antisense oligonucleotides are sensitized to methylating agents (Sobol et al. "Requirement of mammalian DNA polymerase-β in base-excision repair" *Nature* 379:183-186, 1996; Walker et al. "A role for the human DNA repair enzyme HAP1 in cellular protection against DNA damaging agents and hypoxic stress" *Nucleic Acids Res* 22:4884-4889, 1994). In addition, mice deficient in $N^3$-methyladenine DNA glycosylase exhibited increased sensitivity to alkylating drugs like BCNU and mitomycin C (Engelward et al. "Repair-deficient 3-methyladenine DNA glycosylase homozygous mutant mouse cells have increased sensitivity to alkylation-induced chromosome damage and cell killing" *EMBO* 15:945-952, 1996). On the other hand, overexpression of the $N^3$-methyladenine DNA glycosylase, which increases the number of AP sites formed, also increases the cytotoxicity of methylating agents (Coquerelle et al. "Overexpression of N-methylpurine-DNA glycosylase in Chinese hamster ovary cells renders them more sensitive to the production of chromosomal aberrations by methylating agents—a case of imbalanced DNA repair" *Mutation Res.* 336:9-17; 1995.). Finally, cells lacking PARP activity are more sensitive to alkylating agents, with increased apoptosis and chromosomal instability (Menissier-de Murcia et al. "Requirement of poly (ADP-ribose) polymerase in recovery from DNA damage in mice and in cells" *Proc. Natl. Acad. Sci.* USA 94:7303-7304, 1997; Boulton et al. "Potentiation of temozolomide-induced cytotoxicity: a comparative study of the biological effects of poly (ADP-ribose) polymerase inhibitors" *Br. J. Cancer,* 72:849-856, 1995). These data suggest that balanced expression of proteins in the base excision repair complex is important to the efficient processing of lesions. BER is an important mechanism of resistance to therapeutic methylating agents. Accordingly, the present invention contemplates compositions and methods that enhance the effect of a DNA-damaging chemotherapeutic agent (e.g., an agent that induces the formation of AP sites in a cell) through the use of a BER inhibitor in conduction with the anticancer agent.

We examined two classes of agents which could inhibit the BER pathway to determine whether they would increase the cytotoxicity of methylating agents in colon cancer cells, particularly in cells deficient in MMR. Since MMR-deficient cells are tolerant to $O^6$ mG formed by TMZ, any change in cytotoxicity observed after use of a BER inhibitor would be due to interruption in repair of $N^7$ mG and $N^3$ mA DNA adducts. Our first strategy was to combine methoxyamine (MX) with TMZ. MX has been shown to react with the free aldehyde formed at the abasic site exposed by glycosylases and to reduce cleavage at AP sites in mammalian cells, suggesting that the MX-bound abasic site is not a substrate for AP endonuclease (Fortini et al. "Mutagenic processing of ethylation damage in mammalian cells: the use of methoxyamine to study apurinic/apyrimidinic site-induced mutagenesis" *Cancer Res.* 53:1149-1155, 1993). Since AP sites modified by MX are relatively stable and must be converted to cytotoxic lesions, we hypothesized that MX would interrupt BER in cells and potentiate the cytotoxic effects of TMZ, even in MMR defective cells. The second strategy we used was to inhibit PARP with 3,4-dihydro-5-methoxyisoquinolin-1 (2H)-one (PD128763), 3-aminobenzamide (3-AB) or 6-aminonicotinamide (6-AN) and to subsequently treat cells with TMZ. We hypothesized that inactivated PARP would affect short- and long-patch BER, destabilize strand breaks, reduce interaction with other proteins during repair of methylated DNA adducts, and lead to cell death in both MMR-proficient and -deficient cells.

As contemplated above, since MMR-defective cell lines are remarkably resistant to methylating agents yet accumulate high levels of 3 methylating DNA adducts, $O^6$ mG, $N^3$ mA and $N^7$ mG, we reasoned that the interruption of repair of $N^3$ mA and $N^7$ mG adducts by the BER process would sensitize cells to methylating agents. To address this issue, we studied the effect of MX on potentiation of TMZ-induced cytotoxicity. MX interacts specifically with the tautomeric open-ring form of deoxyribose generated from the removal of an abnormal base by glycosylase. The MX-modified AP site is relatively stable (Liuzzi and Talpeart-Borle "A new approach to the study of the base-excision repair pathway using methoxyamine" *J. Biol. Chem.* 260:5252-5258, 1985; Rosa et al. "Processing in vitro of an abasic site reacted with methoxyamine: a new assay for the detection of abasic sites formed in vivo" *Nucleic Acids Res.* 19: 5569-5574, 1991) and inhibits the cleavage of AP sites in DNA by AP endonuclease in mammalian cells. This has been shown to protect cells from cytotoxicity and mutagenicity induced by $SN_1$-type ethylating agents, such as ENU, but not $SN_2$ alkylating agents diethylsulfate and MMS (Fortini et al. "Mutagenic processing of ethylation damage in mammalian cells: the use of methoxyamine to study apurinic/apyrimidinic site-induced mutagenesis" Cancer Res. 53: 1149-1155, 1993; Fortini et al. "Methoxyamine modification of abasic sites protects CHO cells from the cytotoxic and mutagenic effects of oxygen alkylation" *Carcinogenesis* 13: 87-93, 1992). Moreover, the protection was strictly time-dependent and was limited to the short period (30 min) after exposure to the alkylating agents (Fortini et al. "Methoxyamine modification of abasic sites protects CHO cells from the cytotoxic and mutagenic effects of oxygen alkylation" *Carcinogenesis* 13: 87-93, 1992).

In our initial studies, we observed that MX reduced cleavage at AP sites and decreased BER in human colon cancer cell extracts. However, we did not see protection of these two cell lines from ENU cytotoxicity using longer duration exposure to MX. The short duration of MX studied previously may not have the same impact on BER inhibition as does a longer exposure to MX. Our results showed that MX synergistically increased TMZ-induced cytotoxicity in human colon cancer cell lines in both MMR-proficient and -deficient cells. A similar degree of enhanced cytotoxicity was observed with MX and MMS and with TMZ as well. The effect of BG inhibition of AGT was additive to the effect of MX only in the MMR-proficient SW480 cell line but not in the MMR defective HCT116 cell line. These data suggest that $O^6$ mG DNA adducts do not contribute to the enhanced cytotoxic effect of TMZ by MX. Furthermore, a similar degree of enhanced cytotoxicity was observed with MX and MMS as with TMZ, again implicating $N^3$ nA and $N^7$ mG induced abasic sites as the major targets for MX. In our recent studies, a prolonged exposure to low dose MX results in even greater potentiation of TMZ cytotoxicity.

Without wishing to be bound by any theory, mechanisms of MX-enhanced cytotoxicity of methylating agents in colon cancer cells may be due to i) the MX-AP site complex being able to block the AP endonucleolytic step of the BER pathway; ii) the persistence of abasic sites increasing topoisomerase II-mediated DNA cleavage (Kingma and Osheroff "Apurinic sites are position-specific topoisomerase II poisons" *J. Biol. Chem.* 272: 1148-1155, 1997); iii) AP sites inhibiting DNA replication and triggering programmed cell death Robertson et al. "Down-regulation of apurinic/apyrimidinic endonuclease expression is associated with the induction of apoptosis in differentiating myeloid leukemia cells" *Cell Growth & Differentiation* 8: 443-449, 1997).

Under normal circumstances, TMZ produces strand breaks during BER-mediated repair of $N^7$ mG and $N^3$ mA adducts which are efficiently repaired and do not contribute to cytotoxicity until high concentrations of adducts are achieved. When DNA strand breaks are present, one component of the response is recognition, binding and activation of PARP. Activated PARP leads to autoribosylation, and this in turn facilitates access of repair enzymes to DNA damage (Willson "Mammalian base excision repair and DNA polymerase beta" *Mutation Res.* 407: 203-215, 1998; Buschfort et al. "DNA excision repair profiles of normal and leukemic human lymphocytes: functional analysis at the single-cell level" *Cancer Res.* 57: 651-658, 1997) and appears to enhance processing of stand breaks and religation by polymerase-β and ligase I (Althaus et al. "Histone shuttle driven by the automodification cycle of poly(ADP-ribose) polymerase" *Environ Mol Mutagen*, 22: 278-282, 1993). In the alternative BER pathway, PARP interacts with XRCC1 to facilitate repair (Caldecott et al. "XRCC 1 polypeptide interacts with DNA polymerase β and possibly poly (ADP-ribose) polymerase, and DNA ligase III is a novel molecular 'nick-sensor' in vitro" *Nucleic Acids Res.* 24: 4387-4394, 1996). It seems likely that PARP plays an important role in communication between repair proteins and stability of the repair complex involved in BER. This suggests that inhibition of PARP leads to an impaired ability to rejoin DNA strand breaks which can initiate both apoptotic and non-apoptotic cell death cascades and thereby increase cytotoxicity of TMZ (Wedge et al. "3-Aminobenzamide and/or $O^6$benzylguanine evaluated as an adjuvant to temozolomide or BCNU treatment in cell lines of variable mismatch repair status and $O^6$-alkylguanine-DNA alkyltransferase activity" *Br. J. Cancer* 74: 1030-1036, 1996). Our results support this hypothesis. Potentiation of cytotoxicity of methylating agent with PARP inhibitors was observed with a marked increase in apoptosis and PARP cleavage.

Results of BCNU combined with either MX or PD128763 are in sharp contrast to TMZ; little if any potentiation is observed in the absence of BG in either cell line. This suggests that while BER appears to process BCNU induced crosslinks, inhibition of BER in this manner has little impact on BCNU toxicity. One of the best studied BCNU-induced lethal lesions is the $N^3$C—$N^1$ G interstrand cross-link formed after initial chloroethyl monoadducts at $O^6$ G and cyclic rearrangement to $N^1,O^6$-ethanoguanine (Wilson et al. "Life without DNA repair" *Proc. Natl. Acad. Sci.* USA 94: 7303-7304, 1997). However, treatment of cells with BCNU also produces alkylated bases that may be labile and spontaneously result in breakage or nicking of the phosphoribosyl backbone (Gonzaga et al. "Identification of the cross-link between human $0^6$-metnine-DNA methyltransferase and chloroethylnitrosourea-treated DNA" *Cancer Res.* 52:6052-6058, 1992). Since PARP has been shown to bind to BCNU-induced DNA nicks in vitro (Prakash and Gibson "Sequence-selective depurination, DNA interstrand cross-linking and DNA strand break formation associated with alkylated DNA" *Carcinogenesis* 13: 425-431, 1992), it is reasonable to assume that PD128763 might increase BCNU-mediated cytotoxicity. However, our studies showed only minor enhancement of toxicity in HCT116 cells and no enhancement in SW480 cells. Even though methyladenine DNA glycosylase has been implicated in BCNU cross-link repair and its absence sensitizes cells to BCNU (Malapetsa et al. "Identification of a 116 kDa protein able to bind 1,3-bis (2-chloroethyl)-1-nitrosourea-damaged DNA as poly (ADP-ribose) polymerase" *Mutation Res.* 362: 41-50, 1996), we did not observe sensitization to BCNU by treatment with MX in the absence of BG. In the presence of BG, MX potentiated BCNU toxicity, indicating that MX may interfere with DNA cross-link repair pathway and suggesting that BER may be involved in repair of the $N^1O^6$anoguanine cross-link which is not formed if AGT reacts with the $O^6$chloroethylguanine adduct. Taken together, these data suggest a different reaction of MX with damaged DNA induced by BCNU compared to TMZ. With TMZ, MX-enhanced cytotoxicity is associated with AP sites generated from repair of $N^7$ mG and $N^3$ mA DNA adducts formed by methylating agent but with BCNU, it might be the $O^6$ lesion-induced cross-link which controls BCNU toxicity.

While an understanding of the precise mechanism is not needed to practice the present invention, it appears that apoptosis mediates both MX and PD128763-enhanced cytotoxicity of TMZ. Increased apoptosis was observed in MMR wt SW480 cells but not in NMR-deficient HCT116 cells after treatment with BG and TMZ. This suggests that MMR processing of $O^6$ mG is a potent apoptosis-inducing event (Matijasevic et al. "Protection against chloroethylnitrosourea cytotoxicity by eukaryotic 3-methyladenine DNA glycosylase" *Proc. Nad. Acad. Sci.* USA, 90:11855-11859, 1993). Although the biological and functional consequences of PARP and its cleavage in apoptosis still remain to be further identified, it has been demonstrated that PARP is rapidly and specifically cleaved during apoptosis (Kaina et al. "Chromosomal instability, reproductive cell death and apoptosis induced by $O^6$-methylguanine in Mex–, Mex+ and methylation-tolerant mismatch repair compromised cells: facts and models" *Mutation Res.* 381: 227-241, 1997; Lindahl et al. "Post-translational modification of poly(ADP-ribose) polymerase induced by DNA strand breaks" *Trends Biochem Sci* 20: 405-411, 1995). PARP cleavage was observed in both SW480 and HCT116 cells after treatment with either MX or one of the PARP inhibitors and TMZ, confirming activation of apoptotic pathways.

We noted that arrest at cell cycle checkpoints paralleled the cellular response to DNA damage and that these were dependent on MMR and BER pathways. MMR wt SW480 cells were sensitive to TMZ alone with arrest in the S and G2 phases (Fink et al. "The role of DNA mismatch repair in drug resistance" *Clin. Cancer Res.* 4: 1-6, 1998). The S and G2 arrest were potentiated by MX or by PD128763 despite the fact that SW480 is a p53 mutant cell line. In contrast, even high levels of DNA adducts formed by TMZ in the MMR deficient HCT116 cells did not induce cell cycle checkpoint arrest despite the fact that p53 is wild type in this cell line. This dysregulation of damage-induced cell cycle checkpoint control appeared due to failure of processing $O^6$ mG lesions in MMR deficient cells. However after combined treatment with TMZ and either MX or PD 128763, HCT 116 cells showed S/G2 phase arrest and apoptosis. These results are consistent with previous studies of cell cycle changes following MMS exposure or other compounds that produce 90% $N^3$ mA (Lazebnik et al. "Cleavage of poly(ADP-ribose) polymerase by a proteinase with properties like ICE" Nature 371: 346-347, 1994; Morris et al. "Flow cytometric evaluation of cell-cycle progression in ethyl methanesulfonate and methyl methanesulfonate-exposed P3 cells: relationship to the induction of sister-chromatid exchanges and cellular toxicity" *Environ. Mol. Mutagen.* 18: 139-149, 1991) and the prolonged G2 arrest observed in PARP knockout mice or derived cell lines (Menissier-de Murcia et al. "Requirement of poly (ADP-ribose) polymerase in recovery from DNA damage in mice and in cells" *Proc. Nad. Acad. Sci.* USA 94: 7303-7304, 1997) following DNA damage. These data indicate that both SW480 and HCT116 cells have a similar response to persistent $N^7$ mG and $N^3$ mA lesions, following interruption of BER.

Again, while an understanding of the mechanism is not necessary to practice the invention, it appears that disrupted BER processing of non-$O^6$ mG, most likely $N^7$ mG and $N^3$ mA DNA adducts formed by TMZ is cytotoxic to colon cancer cell lines. This may be particularly important in MMR deficient cells which are resistant to TMZ alone due to the failure to recognize $O^6$ mG DNA adducts. These studies provide evidence that disrupting repair of $N^7$ mG and $N^3$ mA by inhibiting BER or PARP may improve the therapeutic efficacy of methylating agents.

We also investigated whether TMZ and MX-induced MX-AP sites may also act as poisons of topoisomerase II α (topo II), producing dual lethal targets. To analyze the effect of MX-AP site on topo II-mediated DNA cleavage, a position-specific MX-AP site was generated on topo II cleavage sites using oligonuleotides for cleavage assay. Results showed that MX-AP sites were cleaved by both topo II and nuclear extraction from tumor cells, suggesting that MX-AP sites, when located within a topo II cleavage site, stimulate topo II-mediated cleavage, which has been referred to the action of topo II poison. We also found prolonged induction of topo II and remarkable increase in DNA double strand breaks in cells treated with TMZ and MX compared to TMZ alone. Similar results were also observed in cells treated with etoposide but not with N-methyl-maleimide (a catalytic inhibitor of topo II and also an antagonizer of etoposide). Moreover, the potentiation of TMZ by MX was decreased in DEtp cell line that was a subline derived from DLD1 and 5-fold more resistant to etoposide compared to the parental cell line. These findings demonstrate that treatments with TMZ combined with MX exert the same effect as etoposide does to trap or stabilize topo II in DNA cleavage complex that leads to the accumulation of cytotoxic DNA breaks.

Generally, the nomenclature used hereafter and the laboratory procedures in cell culture, tissue culture, tumor biology, and molecular genetics described below are those well known and commonly employed in the art. Standard techniques are used for cell culture methods, experimental design and compound formulation and nomenclature. Generally chemical reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y., which are incorporated herein by reference) which are provided throughout this document. All the information contained therein is incorporated herein by reference. Assays for detecting the ability of agents to inhibit or enhance TMZ-mediated tumor reduction provide for facile high-throughput screening of agent banks (e.g., compound libraries, peptide libraries, and the like) to identify potentiators. Such TMZ potentiators may be further developed as potential therapeutics and/or diagnostic or prognostic tools for diverse types of cancers. Likewise, TMZ and various potentiators may be useful in the treatment or diagnostics of other diseases. For example, such combinations of drugs may be directed to virally or parasitically infected cells.

Thus, the present invention provides a method for potentiating the toxicity of temozolomide in human cancer cells by administering an APE- or a PARP-inhibiting amount of an APE or PARP inhibitor. The present invention also provides a product comprising temozolomide and an APE or PARP inhibitor as a combined preparation for simultaneous, separate or sequential administration in said treatment of human cancer cells. Additionally, the present invention provides a method for screening compounds that may potentiate the toxicity of temozolomide by inhibiting APE or PARP, or by other mechanisms.

I. Potentiation of Temozolomide Treatment for Cancer

The present invention contemplates compositions and methods for the potentiation of the elimination of cancer cells by temozolomide. While not limiting the invention to any particular mechanism, it is believed that temozolomide works as an anticancer agent by producing the DNA adducts $O^6$ mG, $N^7$ mG and $N^3$ mA. An accumulation of adduct results in the apoptotic elimination of the cell. However, the $O^6$ mG adducts are typically repaired by the MMR system and the $N^7$ mG and $N^3$ mA adducts are typically repaired by the base excision repair (BER) system. After removal of the abnormal base by methylpurine glycosylase, AP endonuclease (APE) cleaves the back bone and removes the sugar, allowing DNA repair. If the number of adducts produced outstrips the cells ability to repair the damage, or the BER repair mechanism is rendered ineffective, damage will accumulate and the cell will be eliminated through an apoptotic mechanism. Methoxyamine reacts with the abasic site and prevents APE cleavage, disrupting DNA repair. Methoxyamine has been shown in the present invention to potentiate the activity of temozolomide in the treatment of cancer. PARP aids in the repair of DNA strand breaks induced during MMR and BER. As such, inhibitors of PARP activity have been shown in the present invention to be effective in potentiating the activity of temozolomide in the elimination of cancer cells. The effectiveness of temozolomide as an anticancer agent can be greatly enhanced when used in conjunction with a potentiator that prevents the repair of the DNA adducts created as a result of treatment of the cell with temozolomide.

Temozolomide has been found to be most preferably administered in repeat dosages on consecutive days, and the dramatic potentiation effects of the present invention are realized in the highly preferred regimen involving the administration of MX or a PARP inhibitor prior to, or concurrent with, the administration of each dose.

Preferably, this administration of an APE or PARP inhibitor is repeated over a period of several days and is prior to the administered doses of temozolomide. Repeat doses can be administered at 1, 2, 3, 4 or 5 days or more with the preferred period of therapy determined by the response of the tumor to the treatment.

In a preferred embodiment, the APE or PARP inhibitor is administered in an APE- or PARP-inhibiting amount, i.e., an amount sufficient to sensitize the tumor in vivo without causing undue sensitization of normal tissue, when the APE or PARP inhibitor is used concurrently with temozolomide.

The amount of the APE or PARP inhibitor used in the present invention varies according to the degree of the effective amount required for the treating of tumor cells. A suitable dosage is that which will result in a concentration of the APE or PARP inhibitor in the tumor cells to be treated which results in the depletion of the APE or PARP activity, respectively. If desired, some tumor cells can be obtained by biopsy and can be tested in vitro for their sensitivity prior to in vivo treatment.

The neoplasms for which temozolomide is a particularly suitable treatment include carcinomas, melanomas, sarcomas, lymphomas and leukemias, with specific utility for astrocytoma, gliomas, malignant melanoma, chronic lymphocytic leukemia, lung cancer and best(sic) cancer.

Typical dosage ranges of temozolomide are generally between 0.1 and 200, preferably between 1 and 20 mg/kg body weight per day. The amount of APE inhibitor or PARP inhibitor necessary for the potentiation of temozolomide is dependent upon the amount of APE or PARP, respectively, normally present in the cancer cell type. A cancer cell having higher levels of APE or PARP may be affected more dramatically by the preadministration or simultaneous administration of the APE or PARP inhibitor. Additionally, the amount of APE or PARP inhibitor necessary depends on the age and condition of the patient, the severity of the cancer being treated and the particular inhibitor being utilized.

II. Drug Screens

As noted above, the present invention contemplates screening assays for identifying compounds that inhibit tumor growth. The present invention contemplates a screening assay utilizing cell lines that are resistant to an anticancer drug such as temozolomide to screen for compounds that potentiate the anticancer drug. In one embodiment, a resistant cell line is pretreated with the test compound followed by treatment with the anticancer agent. Cell growth and/or apoptosis are then measured. In another embodiment, the test compound is given simultaneously with the anticancer agent.

Additionally, the present invention contemplates the screening of compounds by the use of xenographs. In one embodiment, tumor cells are injected into immune-compromised mice (or other suitable animal) and allowed to grow. Mice carrying the tumors are then treated with the test compound in parallel with or prior to treatment with an anticancer agent such as temozolomide. Tumor size is then measured to follow the effect of the treatment.

It is not intended that the present invention be limited by the nature of the drugs screened in the screening assay of the present invention. A variety of compounds, including peptides, organic compounds, nonorganic compounds, as well as, formulations of more than one compound, are contemplated.

It is also not intended that the present invention be limited by the particular tumor cells used for the drug testing. A variety of tumor cells (for both positive and negative controls) are contemplated (including but not limited to cells set forth above and in the examples below).

It is also not intended that the present invention be limited by the mechanism by which the potentiation is induced. For example, the compound may work by inhibiting APE cleavage, by inhibiting other DNA repair mechanisms (e.g., PARP) or by other as of yet unidentified mechanisms.

It is contemplated that the invention be utilized in the screening of compounds by high-throughput screening methods. For example, automated systems and microscale assay systems are contemplated. Furthermore, it is contemplated that the invention can be used for the screening of compound libraries (e.g., drug libraries) utilizing these high-throughput screening methods.

The identification of BER inhibitors as enhancers of anticancer drugs is important because it identifies a new target, AP sites in DNA for anticancer drug development. Recent evidence indicates that AP sites are common DNA lesions for anticancer drugs that attack DNA, generating modified bases that are removed by DNA glycosylases. Thus, BER inhibitors have the potential to improve the therapeutic efficacy of a broad spectrum of anticancer agents. MX is an effective prototypical agent and leads to the direction for the development of new drugs. Below is a high-throughput screening assay to identify new inhibitors of BER that are able to block AP site cleavage by APE and potentially enhance therapeutic efficacy. Screening studies will provide a broad effort at new drug development.

Figure 22A:
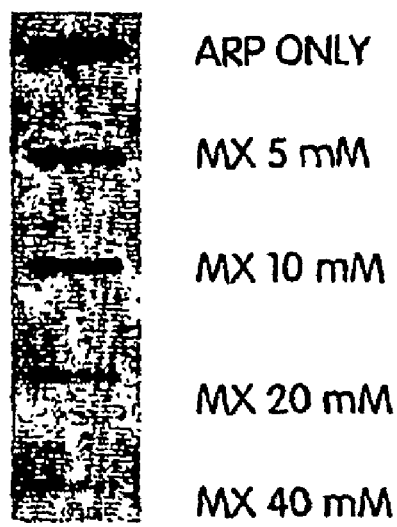
FIG. 22A shows that MX inhibited detection of AP sites by ARP.
Figure 22B:
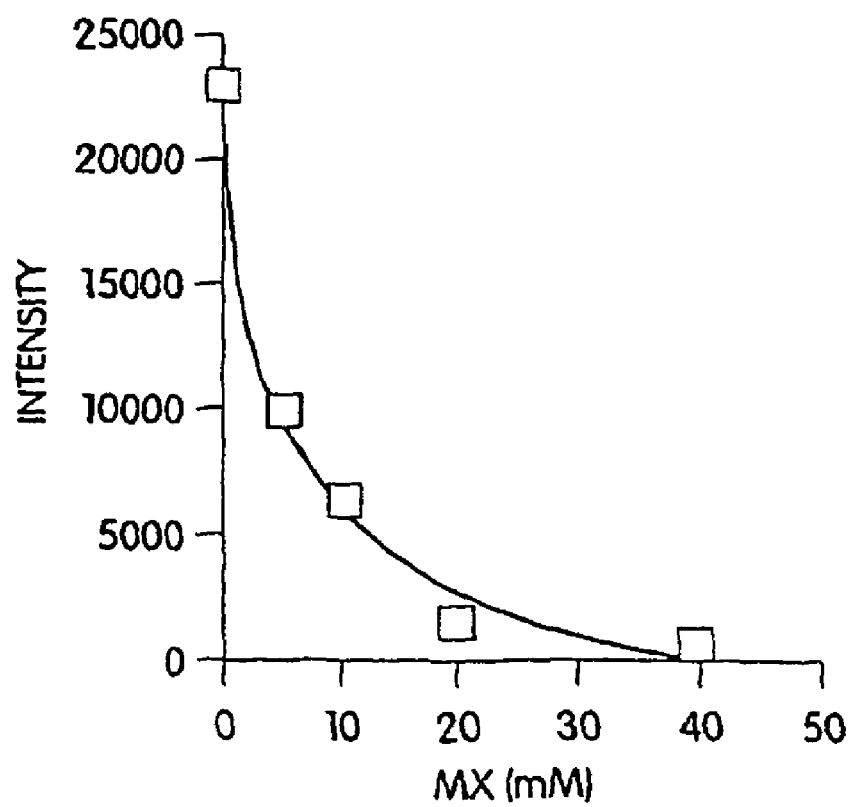
FIG. 22B shows the relative reduction of AP sites estimated by densitometric intensity, indicating that MX (5-20 mM) blocked 38-80% of AP binding sites.

High-throughput screening methods include two molecular reaction assays:

1. Analysis of chemical—modified AP Sites assayed by Aldehyde Reactive Probe (ARP). This is a competitive assay to measure the reactivity with AP site between ARP reagent (Dojindo Molecular Technologies Inc., Gaithersburg, Md.) and the screening compounds. ARP and MX have a similar reactivity with AP sites. They react specifically with an aldehyde group that is open ring form of the AP sites. Thus this assay will allow identification of compounds with potential to block AP site repair based on the binding affinity and efficiency to AP sites of screening compounds compared to ARP and MX.

a. AP site standard preparation: AP sites were produced in a calf thymus DNA by heat/acid-buffer solution. Intact calf thymus DNA was added to sodium citrate buffer (10 mM sodium citrate containing 10 mM $NaH_2PO_4$ and 10 mM NaCl, pH 5.0) and held at 70° C. for 30 min. The reaction was stopped by chilling rapidly on ice, and the DNA was then precipitated with cold ethanol, washed with 70% ethanol, dried, and resuspended in sterilized distilled water.

b. AP-DNA (15 pg) was incubated with test compounds at different concentrations at 37° C. for 30 min prior to ARP (1 mM) or ARP alone (Dojindo Molecular Technologies Inc., Gaithersburg, Md.) for 30 min. After precipitation and wash with ethanol, DNA was resuspended in TE buffer (10 mM Tris-HCI, 1 mM EDTA, pH 7.2). DNA was heat-denatured at 100° C. for 5 min, quickly chilled on ice, and mixed with an equal amount of 2 M ammonium acetate. The single-stranded DNA was then immobilized on a BAS-85 NC membrane (Schleicher and Schuell) using a vacuum filter device (Schleicher and Schuell). The NC membrane was incubated with streptavidinconjugated horseradish peroxidase (BioGenix) at room temperature for 30 min. After NC membrane was rinsed with washing buffer containing NaCl (0.26 M), EDTA (1 mM), Tris-HCI (20 mM), and Tween 20 (1%), ARP-AP sites are visualized with ECL reagents (Amersham Corp.) (FIG. 22A) and quantitated by scanning densitometer (FIG. 22B).

Figure 23B:
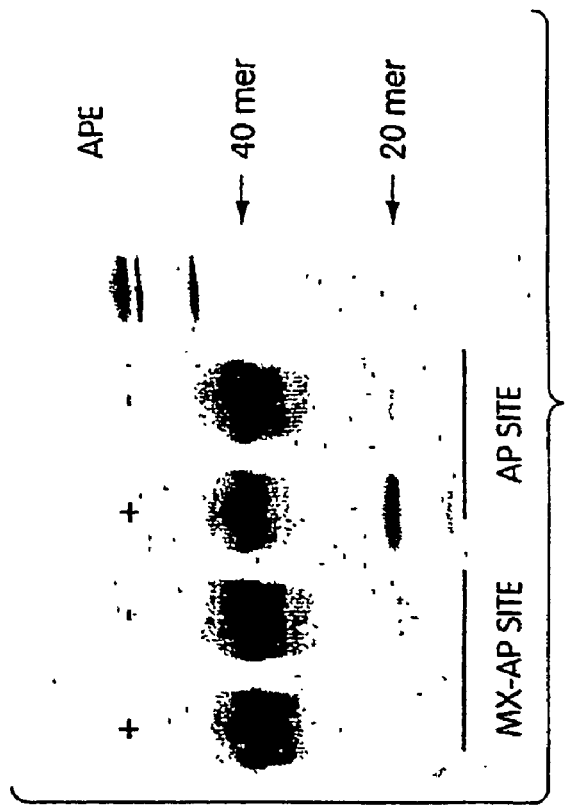
FIG. 23B shows that MX-AP sites are resistant to cleavage by APE.
Figure 23A:
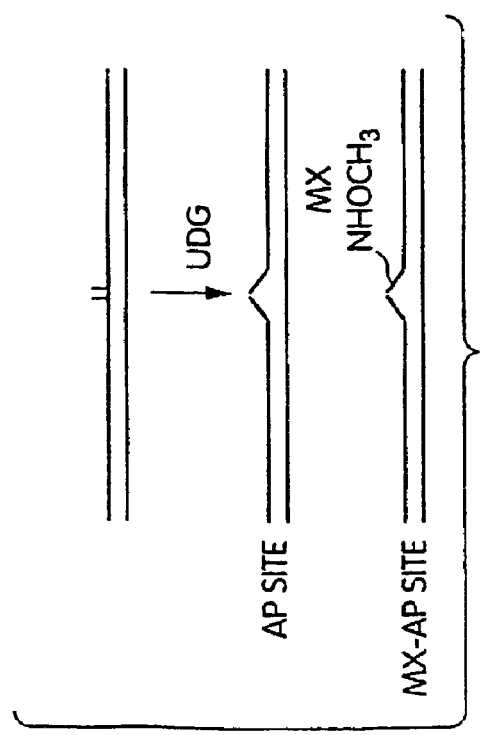
FIG. 23A is a diagram depicting the preparation of DNA substrates containing either regular AP sites or MX-modified AP sites.

2. AP sites cleavaged by AP-endonuclease (APE). This assay confirms that AP sites modified by potential BER inhibitors are resistant to cleavage by APE, (Trevigen, Gaithersburg, Md.) a BER protein. The assay may be performed as follows (see also FIGS. 23A and B):

a. AP site is prepared by replacing single nucleoside with deoxyuridine in duplex oligonucleotides (40 mer).

b. Regular AP site is produced in the duplex oligonucleotides by human uracil DNA glycosylase (LIDGase, Trevigen, Gaithersburg, Md.) to remove the uracil residue.

c. To generate MX-adducted AP site substrates: the UDG-treated duplex oligonucleotides are mixed with 10 mM MX in buffer containing 10 mM KPO4, pH 7.1 and incubated at 37° C. After 30 min, the substrates are recovered by ethanol precipitation, lyophilized, resuspended in water, and stored at −20° C.

d. APE-cleavage reaction: DNA substrates containing either regular AP-sites or chemicalmodified AP sites are incubated with APE (Trevigen, Gaithersburg, Md.) for 30 min and reactants are precipitated with 100% cold ethanol, washed with 70% ethanol and resuspended in TE buffer. The reactants are resolved by denaturing 20% polyacrylamide gel electrophoresis and visualized by silver staining (Silver Staining Kit, Pharmacia Biotech).

EXEMPLIFICATION

Materials and Methods

Chemicals and Reagents. BG was generously provided by Dr. Robert Moschel (Frederick Cancer Research and Development Center, National Cancer Institute). Stock solution was made in dimethylsulfoxide. TMZ and BCNU were obtained from the Drug Synthesis and Chemistry Branch, Drug Therapeutic Program, National Cancer Center Institute. PD128763 was a gift from Park-Davis Pharmaceutical Division. 6-AN, 3-AB, MX and methylmethane sulfonate (MMS) were purchased from Sigma (ST. Louis, Mo.). Stock solutions of PD128763, 3-AB and 6-AN were prepared by dissolving in dimethylsulfoxide and added to cell culture at a final concentration of <1% DMSO, when cells were treated with these compounds. MX was dissolved in sterilized water (pH 7.0). All stock solutions were kept at −20° C. BCNU was prepared fresh in 0.5 ml of 100% ethanol, diluted in PBS, and used with in 10 min.

Colony Survival Assay. SW480 cells were obtained from the ATCC. HCT116 cells were obtained from R. Boland, University of Michigan Medical Center. All cell lines were cultured in appropriate growth medium.

Cells (2000/dish) were plated, adhered for 18 hrs and treated with TMZ or

MMS plus or minus modifiers such as BX, MX, 6-AN, 3-AB or PD128763, according to experimental protocol. After treatment, cells were washed and fresh medium was replaced. The cells were grown for a further 7 days prior to staining with methylene blue for determination of colonies containing more than 50 cells. Comparisons of drug induced cytotoxicity consisted of a calculation of the dose modification factor (DMF), defined as the ratio of the $IC_{50}$ of either TMZ or MMS in the absence to that in the presence of indicted modifier(s), i.e., DMF=$IC_{50}$ for TMZ alone/$IC_{50}$ for TMZ plus modifier(s).

Median Effect Analysis (MEA). MEA was used to determine the dose-response interactions between TMZ and either MX or PD 128763. Drugs were combined at the ratio of the $IC_{50}$ values for either TMZ and MX or TMZ and PD 128763 as determined by survival/concentration curves. The combination was compared to the cytotoxicity of each drug alone in every experiment. The combination index (CI) was determined from colony-forming assays at increasing levels of cell killing, using analysis of multiple drug interaction program (Biosoft, Cambridge, United Kingdom) developed based on method of Chou and Talalay (Chou and Talalay "Quantitative analysis of dose-effect relationship: the combined effects of multiple drugs on enzyme inhibitors" In: G. Weber (ed.) *Advances in Enzyme Regulation*, pp. 27-55, New York: Pergamon Press, 1983). CI values of less than or grater than 1 indicate synergy and antagonism, respectively, whereas a CI value of 1 indicates additivity of the drugs.

Flow Cytometry for Cell Cycle Distribution Analysis. For cell cycle analysis, $10^6$ cells were plated in 100-mm tissue culture dishes and exposed to MX (6 mM)/PD128763 (100 μM) or MX (6 mM)/PD128763 (100 μM) plus TMZ (300 μM) at 37° C. After 24 h-72 h of culture, cells were fixed in 80% ethanol and DNA was stained with 20 μg/ml propidium iodide. DNA fluorescence of PI-stained cells was measured with an Elite ESP flow cytometer/cell sorter (Coulter, Miami, Fla.). Cell cycle distribution was analyzed with Modfit 5.2 program (Verity software, Topsham, Mass.) at least 10,000 cells per data point.

Western Blotting for PARP Cleavage Detection. Cell extracts were resolved by SDS-PAGE (12% polyacrylamide) in a Bio-Rad minigel apparatus at 150 V for 1 hr. Proteins were transferred onto PVDV membranes, using a Bio-Rad mini Trans-Blot cell for 1 hr at 100 V. The blotted membranes were blocked with 5% dry milk in 15 TBS buffer and then probed for 2 hr with anti-PARP antibody C2-10 (Trevigen, Gaithersburg, Md.). After three 5 min washes with TBS-Tween20 (0.05%), the blots were incubated with secondary antibody, anti-mouse HRPO-anti IgG for 1 hr (Amersham Life Science, Arlington Height Ill.). Antibody binding was visualized by ECL according to manufacturer's instructions (Amersham Life Science, Arlington Heights, Ill.).

Tumors in Nude Mice. Tumor cells ($5 \times 10^6$) were injected into flanks of female athymic HSD nude mice, at 6-8 weeks of age. The tumors were measured with calipers using the National Cancer Institute formula: V=L(mm)×$I^2$ (mm)/2 where L is the largest diameter and I is the smallest diameter of the tumor. When the volume of the nodules had achieved about 100-150 mm³, tumor-bearing mice were assigned randomly for the control or treatment groups (3-5 mice/group).

Antitumor Effects of TMZ and MX plus TMZ. Nude mice carrying tumors were received TMZ, MX or MX combined with TMZ daily for a period of 5 days of treatment. Doses used per group were as follows: a) TMZ alone, 120 mg/kg; b) MX alone, 2 mg/kg; c) BG plus TMZ, 30 mg/kg BG+120 mg/kg; d) MX plus TMZ, 0.2 mg/kg MX+120 mg/kg TMZ.

Experimental End Point. Tumor measurements were taken every 3 days. The relative tumor volume (V/V$_0$) was calculated by dividing the measured tumor volume (V) by the initial tumor volume (V$_0$) at day 0. Tumor responses were quantified by tumor regrowth delay. Tumor growth delays were calculated according to: tumor growth delay=$T_{2X}C_{2X}$, where $T_{2X}$ and $C_{2X}$ represent the number of days treated and control tumors take to double in size from the day of treatment, respectively.

Toxicity Evaluation. Toxicity after treatment was evaluated by body weight measurements and peripheral WBC counting. Body weight was measured three times weekly from the first treatment until 2 weeks after the end of treatment. The weight loss was expressed as a percentage of the initial weight (initial weight−lowest weight/initial weight×100%). Peripheral WBCs were monitored 5 days after the end of treatment compared with WBCs of control mice.

Example 1

Methoxyamine Potentiates Cytotoxicity of TMZ

Figure 1B:
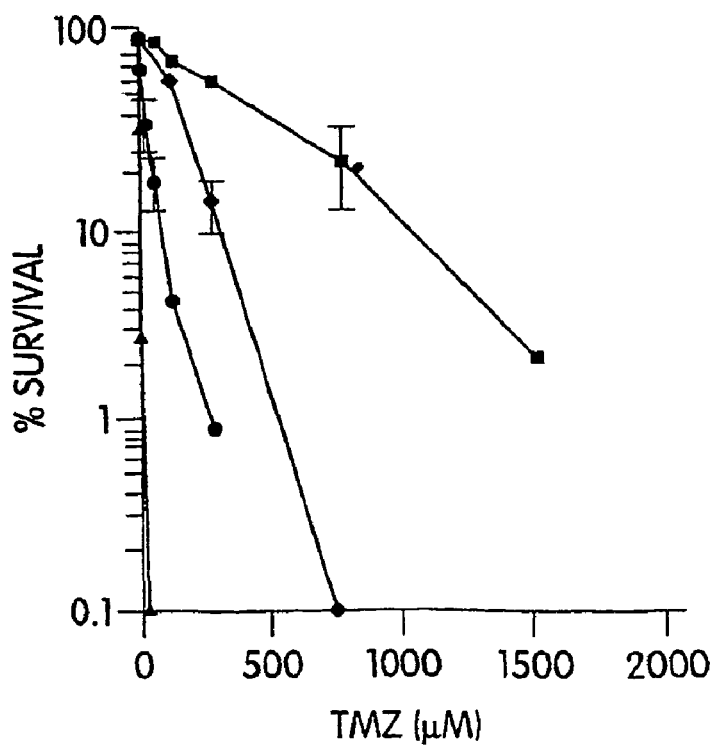

We have previously reported the comparative cytotoxicity of TMZ and BG in the SW480 and HCT116 cells lines (Liu et al "Mismatch repair mutations override alkyltransferase in conferring resistance to temozolomide but not to 1,3-bis(2-chloroethyl)nitrosourea" *Cancer Res.* 56: 5375-5379, 1996). In order to test whether MX would alter TMZ cytotoxicity, we treated SW480 and HCT116 with 6 mM MX (itself a nontoxic concentration) plus TMZ (0-1500 μM) for 2 hr, with or without BG to abolish AGT mediated removal of O$^6$ mG DNA adducts. SW480 cells were moderately resistant to TMZ, with an IC$_{50}$ of 395 μM which was reduced 14-fold to 28 μM by BG pretreatment. Greater resistance to TMZ was observed in MH1 defective cells, even after inhibition of AGT by BG (IC$_{50}$, 950 μM). In both cell lines, MX potentiated the cytotoxic effect of TMZ with a DMF of 2.4 in SW480 and 3.1 in HCT116 (FIG. 1). In SW480 cells, additive effects of MX and BG were noted (IC$_{50}$ was reduced from 395 μM to 6 μM), whereas, with HCT116 cells no effect of BG was seen in the presence of MX (FIG. 1: A. HTC116 cells; B. SW480 cells. (■), TMZ alone; (♦), MX plus TMZ; (●), BG plus TMZ; (▲), BG and MX plus TMZ).

Figure 2A:
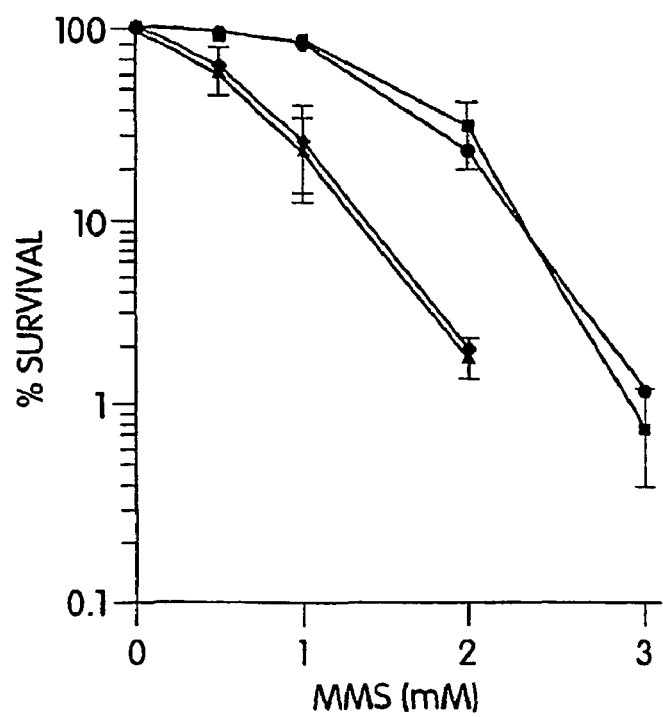
FIG. 2. Cytotoxicity of MMS enhanced by MX in colon cancer cell lines. Cells were treated with 0-3 mM MMS for 1 h or MMS and 6 mM MX plus 10 µM BG for 2 h prior to 2 h exposure to MMS. A. HCT116 cells; B. SW480 cells. (■), MMS alone; (♦), MX plus MMS; (●), BG plus MMS; (▲), BG and MX plus MMS. Results are the mean±SD of at least three separate experiments performed in duplicate.
Figure 2B:
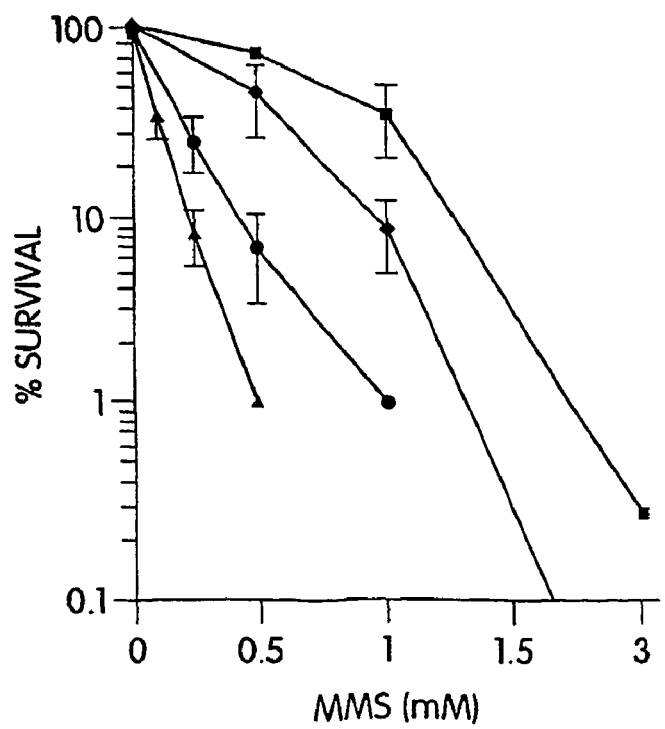

To further decipher the role of N$^3$ mA and N$^7$ mG DNA adducts in the relative absence of O$^6$ mG, we evaluated the effect of MX on MMS mediated cytotoxicity. NMS is a methylating agent which produces far fewer O$^6$ mG adducts (0.3%) and a greater proportion of N$^3$ mA (10%) and N$^7$ mG adducts (87%) than TMZ (Chou and Talalay "Quantitative analysis of dose-effect relationship: the combined effects of multiple drugs on enzyme inhibitors" In: G. Weber (ed.) *Advances in Enzyme Regulation*, pp. 27-55, New York: Pergamon Press, 1983). The IC$_{50}$ of MMS was 0.82 mM in SW480 and 1.4 mM in HCT116 cells. This difference is smaller that the difference in the TMZ IC$_{50}$ between these cell lines, probably because the low level of O$^6$ mG adducts formed by MMS increases the impact of other DNA adducts. After cells were treated with MMS (0-3 mM) plus 6 mM MX for 1 hr., the IC$_{50}$ DMFs, compared to MMS alone, were 2.0 in SW480 and 2.3 in HCT116 (FIG. 2: A. HCT116 cells; B. SW480 cells. (■), MMS alone; (♦), MX plus MMS; (●), BG plus MMS; (▲), BG and MX plus MMS). These DMFs were similar to that observed with TMZ. Compared to treatment of SW480 with BG plus TMZ (DMF was 14), BG plus MMS induced less enhancement of cytotoxicity (DMF was 6). When MMS was combined with BG and MX, >10 fold potentiation of cytotoxicity was observed in SW480 cells, whereas no additive effect was seen in HCT116 cells. In SW480 cells, the increased MMS-toxicity by BG suggests that despite the small number of O$^6$ mG adducts, they contribute to cytotoxicity. In HCT116 cells, increased cytotoxicity was only observed in the combination of TMZ with MX but not with BG, indicating that MX interfered with processing of N$^7$ mG and N$^3$ mA lesions which killed cells. From these data, we infer that MX had equal ability to interrupt BER in theses two cell lines.

Example 2

Inhibitors of PARP Modulate the Sensitivity of Cells to TMZ

Figure 3A:
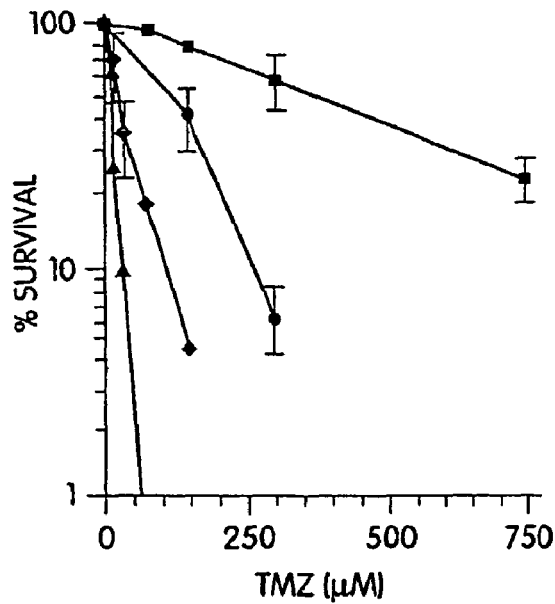
FIG. 3. Inhibitors of PARP enhance cytotoxicity of TMZ in MMR wt SW480 cells. A. Cells were treated with 0-1500 TMZ for 2 h or TMZ and 100 µM PD128763 or plus 10 µM BG for 2 h prior to 2 h exposure to TMZ. (■), TMZ alone; (♦), BG plus TMZ; (●), PD128763 plus TMZ; (▲), BG and TMZ plus PD128763. B. Cells were treated with 0-1500 µM TMZ for 2 h or TMZ and 10 µM 6-AN (pretreated for 48 h) or plus 10 µM BG for 2 h prior to 2 h exposure to TMZ. (■), TMZ alone; (♦), BG plus TMZ; (●), 6-AN plus TMZ; (▲), BG and TMZ plus 6-AN. C. Cells were treated with 0-1500 µM TMZ for 2 h or TMZ and 3 mM 3-AB (pretreated for 24 h) or plus 10 µM BG for 2 h prior to 2 h exposure to TMZ. (■), TMZ alone; (▲), BG plus TMZ; (●), 3-AB plus TMZ; (▲), BG and TMZ plus 3-AB. Results are the mean±SD of at least three separate experiments performed in duplicate.
Figure 3B:
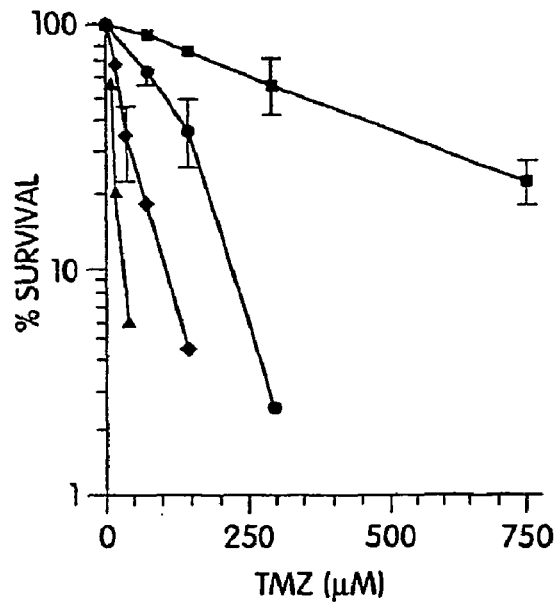
Figure 3C:
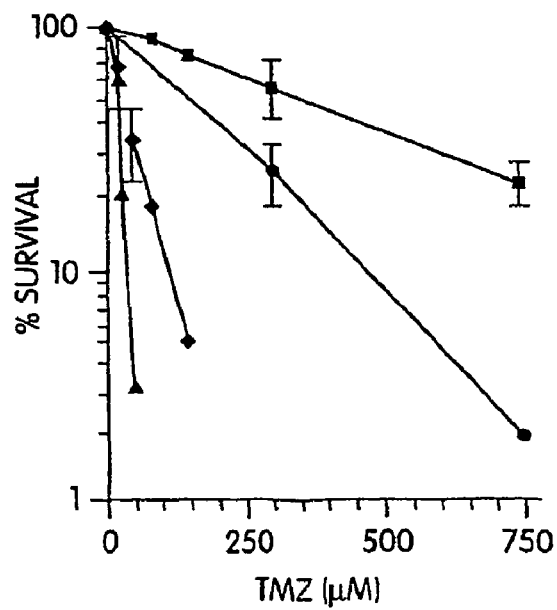
Figure 4A:
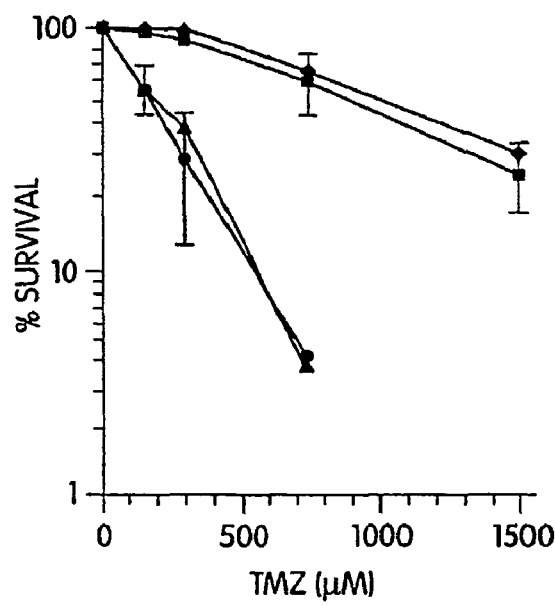
FIG. 4. Inhibitors of PARP enhance cytotoxicity of TMZ in MMR deficient HCT116 cells. A. Cells were treated with 0-1500 TMZ for 2 h or TMZ and 100 µM PD128763 or plus 10 µM BG for 2 h prior to 2 h exposure to TMZ. (■), TMZ alone; (▲), BG plus TMZ; (▲), PD128763 plus TMZ; (▲), BG and TMZ plus PD128763. B. Cells were treated with 0-1500 µM TMZ for 2 h or TMZ and 100 µM 6-AN (pretreated for 48 h) or plus 10 µM BG for 2 h prior to 2 h exposure to TMZ. (■), TMZ alone; (▲), BG plus TMZ; (●), 6-AN plus TMZ; (▲), BG and TMZ plus 6-AN. C. Cells were treated with 0-1500 µM TMZ for 2 h or TMZ and 3 mM 3-AB (pretreated for 24 h) or plus 10 µM BG for 2 h prior to 2 h exposure to TMZ. (■), TMZ alone; (♦), BG plus TMZ; (●), 3-AB plus TMZ; (A), BG and TMZ plus 3-AB. Results are the mean±SD of at least three separate experiments performed in duplicate.
Figure 4B:
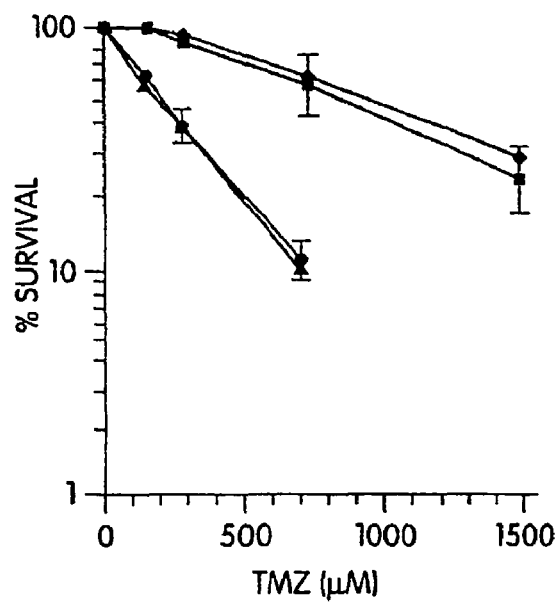
Figure 4C:
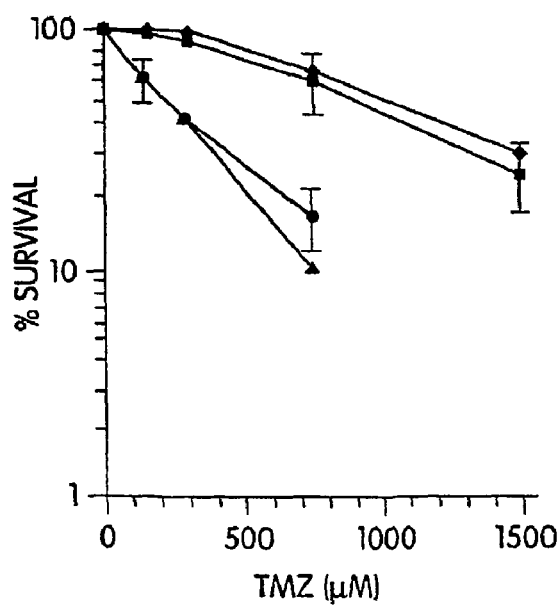

Since inhibitors of PARP may interrupt BER and increase sensitivity to methylating agents, we examined whether inhibitors of PARP sensitize cells to TMZ. FIG. 3a and FIG. 4a ((■), TMZ alone; (♦), BG plus TMZ; (●), PD128763 plus TMZ; (▲), BG and TMZ plus PD128763) display survival after combined treatment of TMZ with PD128763, 3-AB or 6-AN in both SW480 and HCT116 cells. In the SW480 cell line, PD128763 sensitized cells to TMZ with a DMF of 3.3-fold. The combination of PD128763, BG, and TMZ was even more toxic, with a DMF compared to TMZ alone of 36-fold. In HCT116 cells, the DMF for PD128763 and TMZ compared to TMZ alone was 5.0. However, the combination of PD128763, BG and TMZ had no greater effect than PD128763 and TMZ, indicating that persistent O$^6$ mG had no effect on cytotoxicity in this MMR defective cell line. Potentiation of TMZ cytotoxicity was also observed in both cell lines treated with two other PARP inhibitors, 3-AB (FIGS. 3b, 4b: (■), TMZ alone; (♦), BG plus TMZ; (●), 6-AN plus TMZ; (▲), BG and TMZ plus 6-AN) and 6-AN (FIGS. 4c, 4c: (■), TMZ alone; (▲), BG plus TMZ; (●), 3-AB plus TMZ; (▲), BG and TMZ plus 3-AB). Although the specific activity of these agents varied considerably, the DMFs were similar, 3-4-fold, for both 3-AB and 6-AN.

Example 3

Synergistic Interaction Between TMZ and MX or PD128763

Figure 5A:
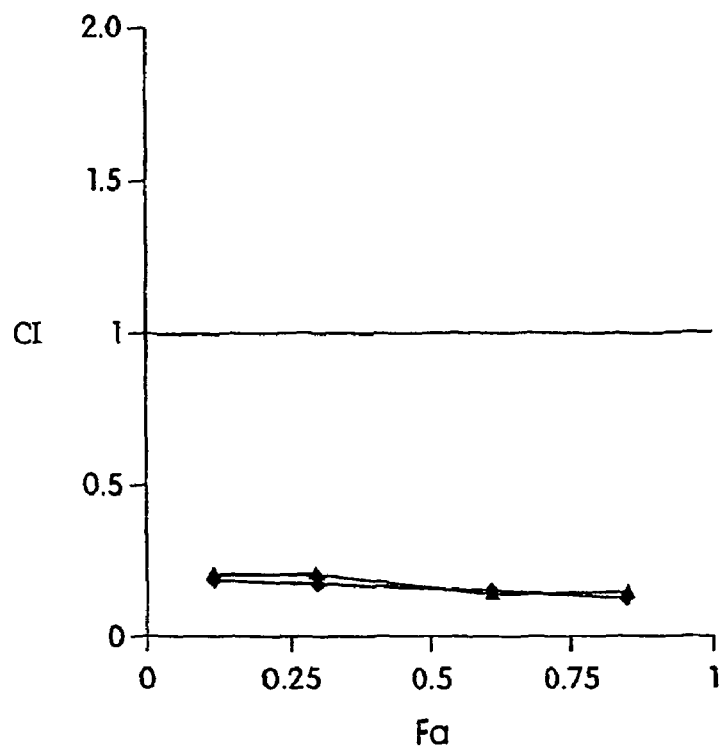
FIG. 5. Synergy analysis of the interaction between TMZ and MX (A) or PD128763 (B) in HTC116 cells.
Figure 5B:
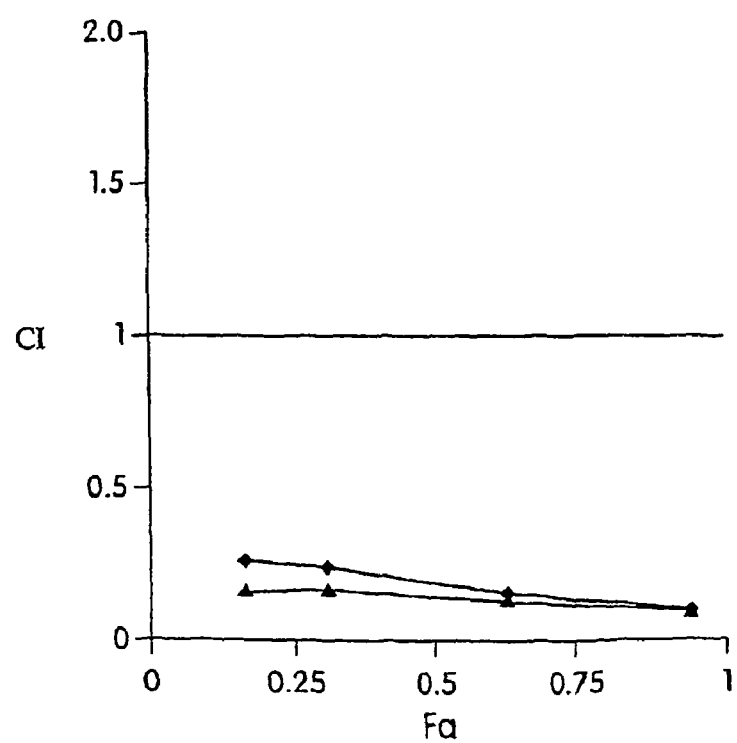

We investigated the nature of the reaction between TMZ and MX in the TMZ-resistant cell line, HCT116. These cells were incubated in the presence of a range of concentrations of TMZ (75-750 μM), of MX (1.5-15.0 mM), or constant molar ratio mixture of TMZ and MX (1:20) for 2 hr. HCT116 cells were also exposed to TMZ and PD128763 (62.5-625 μM) alone and to a combination of (1:0.83) for 2 hr to analyze synergism. As shown in FIGS. 5A and 5B, synergistic interaction (CI<<1, p<0.001) was found in both SW480 cells and HCT116 cells using the combination of TMZ with either MX or PD 128763. These results also showed a marked synergism at high Fa values. Since MDF for these combinations was similar to the observed with SW480 cells, we conclude that BER inhibitor synergizes methylating agent cytotoxicity in both MMR deficient and proficient colon cancer cells.

Example 4

Effect of BER Inhibitors on BCNU Cytotoxicity

Figure 6A:
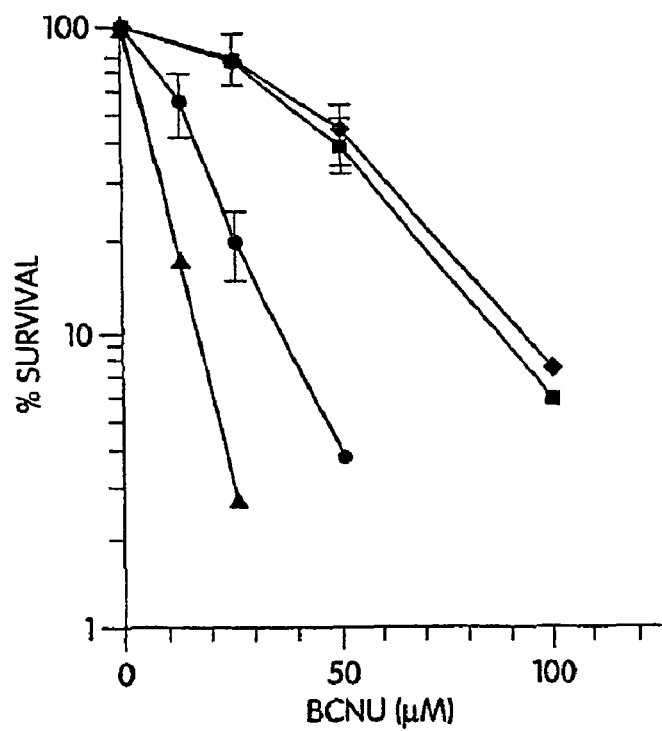
FIG. 6. Survival fraction of human colon cancer cell lines after exposure to BCNU plus MX. Cells were treated with 0-100 µM BCNU for 2 h or BCNU and 6 mM MX plus 10 µM BG for 2 h prior to 2 h exposure to BCNU. A. HCT116 cells; B. SW480 cells. (■), BCNU alone; (♦), MX plus BCNU; (●), BG plus BCNU; (▲), BG plus MX plus BCNU. Results are the mean±SD of at least three separate experiments performed in duplicate.
Figure 6B:
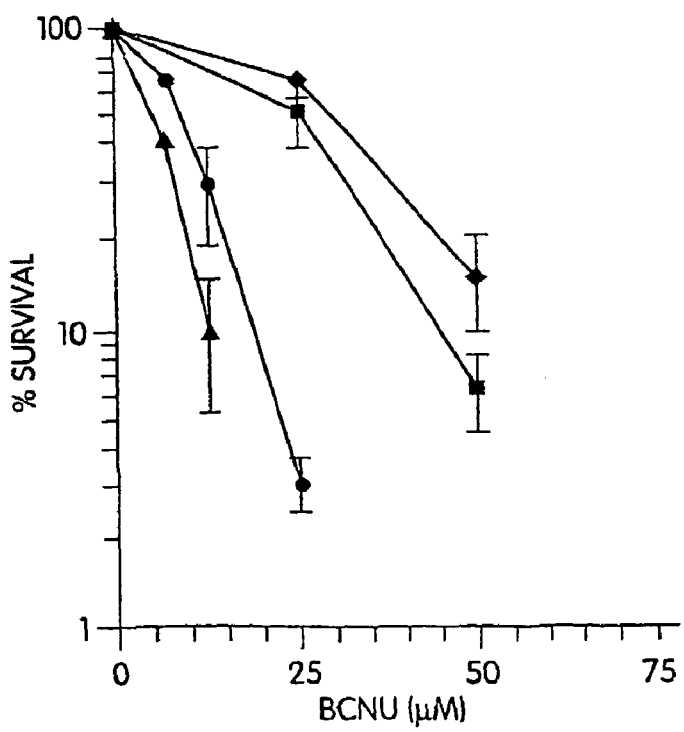
Figure 7A:
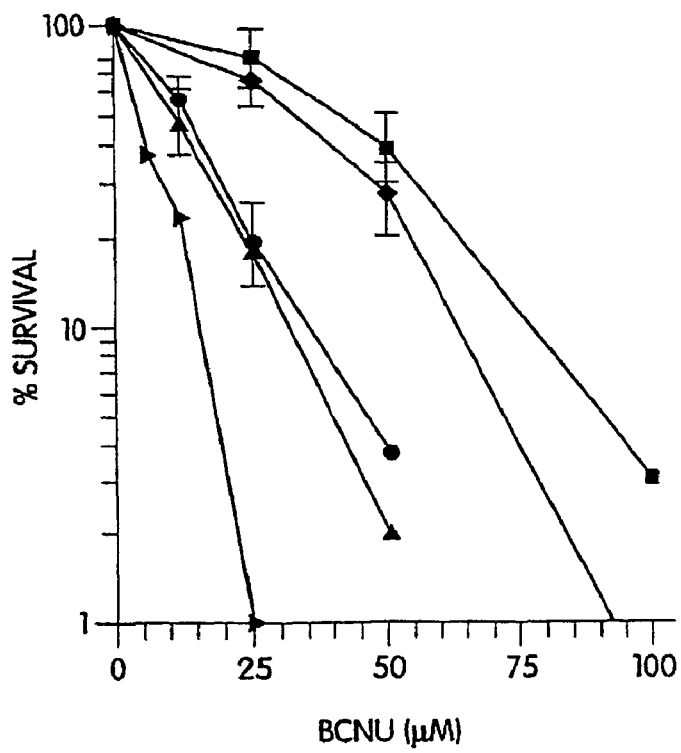
FIG. 7: Survival fraction of human colon cancer cell lines after exposure to BCNU plus PD128763. Cells were treated with 0-100 µM BCNU for 2 h or BCNU and 100 µM PD 128763 plus 10 µM BG for 2 h prior to 2 h exposure to BCNU. A. HCT116 cells; B. SW480 cells. (■), BNCU alone; (♦), PD 128763 plus BCNU; (●) BG plus BCNU; (▲), BG and PD 128763 plus BCNU; (⊕) BG, PD128763 and MX plus BCNU. Results are the mean±SD of at least three separate experiments performed in duplicate.
Figure 7B:
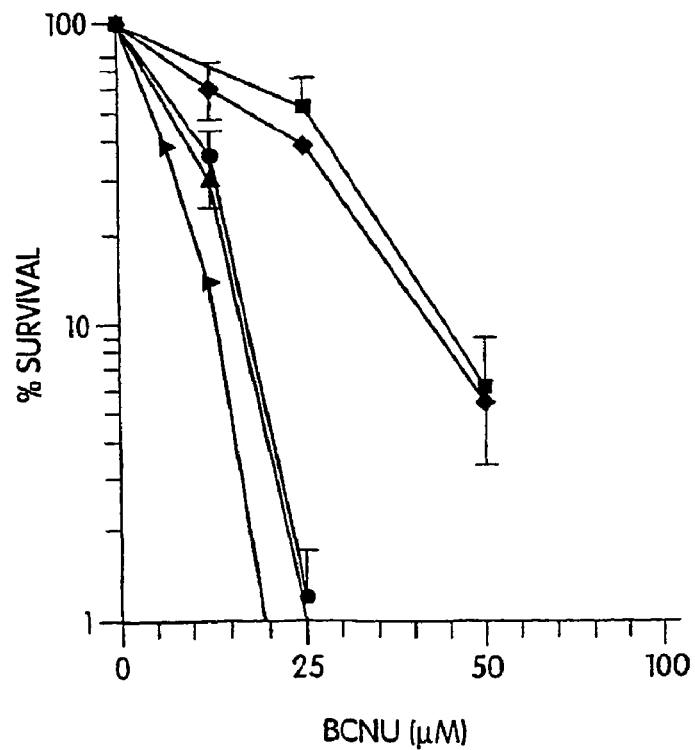

To test whether MX is also able to sensitize colon cancer cells to chloroethylating agents, these two cell lines were pretreated with 6 mM MX for 2 hr followed by BCNU. No enhancement of BCNU cytotoxicity by MX was observed (FIG. 6); the BCNU $IC_{50}$ was 45 µM in HCT116 cells (FIG. 6A: (■), BCNU alone; (♦) MX plus BCNU; (●), BG plus BCNU; (▲), BG plus MX plus BCNU) and 27-29 µM in SW480 cells, respectively, treated with BCNU alone or BCNU plus MX (FIG. 6B: (■), BCNU alone; (♦), MX plus BCNU; (●), BG plus BCNU; (▲), BG plus MX plus BCNU). A greater sensitization to BCNU was observed in these two cell lines when cells were treated with MX plus BG and BCNU, in which the BCNU $IC_{50}$ for both cell lines was 5 µM. However, most of the effect was potentiated due to BG, which increased BCNU cytotoxicity by 3-4 fold. As shown in FIG. 7, no sensitization to BCNU cytotoxicity was seen after treatment with PD 128763 or BG and PD 128763 ((■), BNCU alone; (♦), PD 128763 plus BCNU; (●), BG plus BCNU; (▲), BG and PD128763 plus BCNU; (☞), BG, PD128763 and MX plus BCNU.

Example 5

Effect of Inhibitors of BER on Cell Cycle Distribution and PARP Cleavage

The cell cycle and apoptosis response of SW480 and HCT116 cells was examined at various times after treatment with TMZ (300 µM) alone or with either MX (6 mM), PD128763 (100 µM) or BG (25 µM). After treatment, cells were divided into two aliquots for analysis of cell cycle/apoptosis on days 1 and 3, and (see below) for detection of PARP cleavage. Cell cycle distribution was measured by flow cytometry according to DNA content and estimation of the duration of G1, S and G2/M was based on untreated, exponentially growing, asynchronous cells. MX and PD128763 alone did not affect the distribution of the cell cycle in these two cell lines (data not shown). At 24 hr, 75-90% of SW480 cells accumulated in S and G2 after treatment With TMZ alone and this G2/S phase arrest was more pronounce in cells pretreated with either MX or PD 128763 (FIG. 8A). S/G2 arrest was still present at 3 days in cells treated with the combination of MX or PD 128763 and TMZ (in both instances, 13-20% of the cells were apoptotic). In SW480 cells treated with TMZ alone, the G2/S block was less obvious at day 3 with only 8% of the cells showing evidence of apoptosis. In contrast, HCT116 cells had a normal cell cycle distribution after treatment with TMZ alone and no effect was seen with BG and TMZ. However, accumulation in S phase was observed (FIG. 8B) 24 hr after treatment with PD128763 plus TMZ. At 72 hr, HCT116 cells had moved through S phase and thereafter, a significant portion of cells (90%) remained arrested in G2 with apoptosis present in 1% of the cells. A similar but less striking result was observed with MX and TMZ in HCT116 cells. By 72 hr, 60% of cells were still arrested in S and G2 and 10% of the cells were apoptotic.

Figure 9:
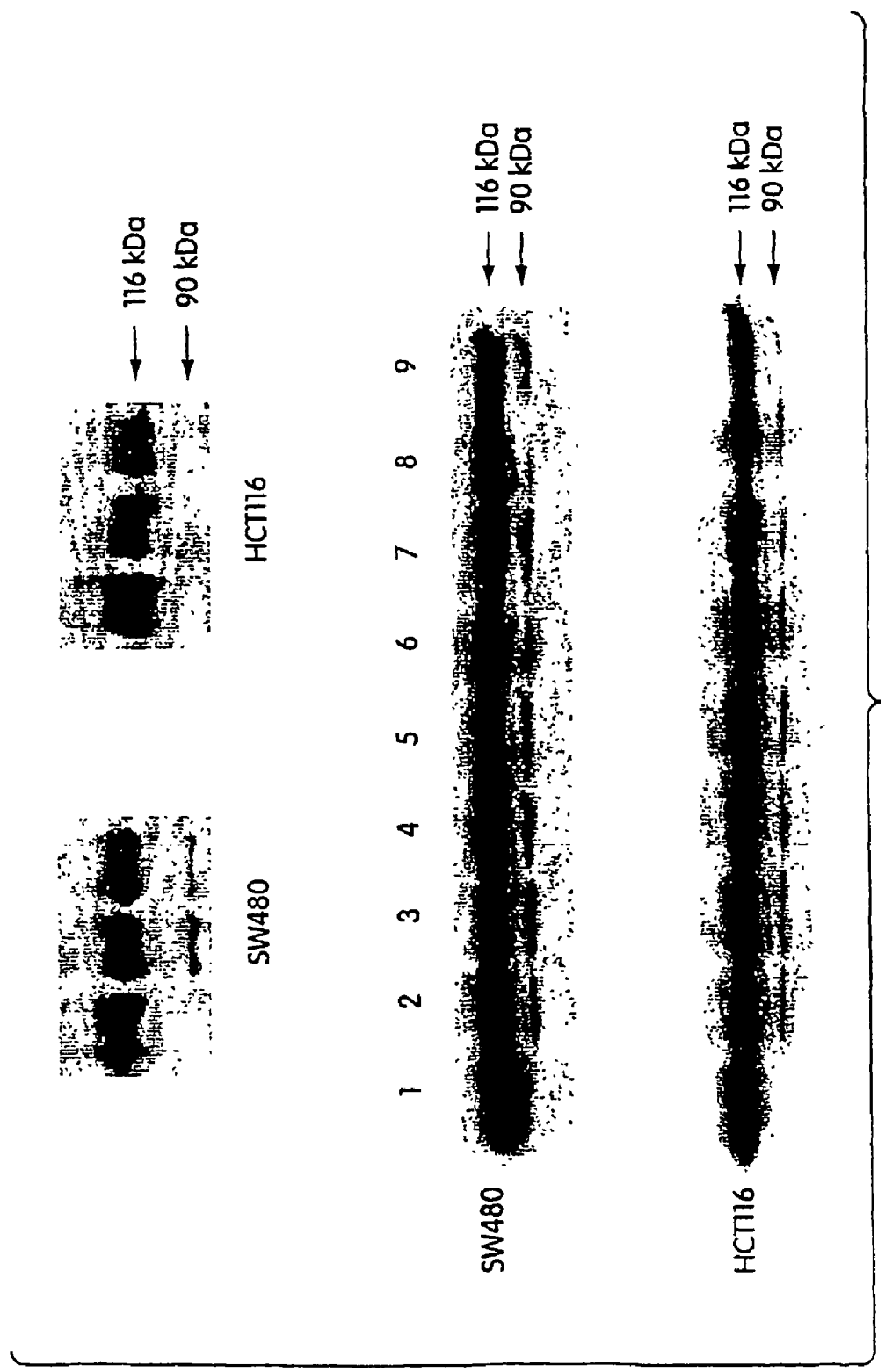
FIG. 9. PARP cleavage in colon cancer cells treated with TMZ plus modifiers. A. Controls, as labeled. B. SW480 cells; C. HCT116 cells; Lane 1, untreated; 2, TMX plus MX; 3, TMZ plus MX plus BG; 4, TMZ plus 3-AB; 5, TMZ plus 3-AB plus BG; 6, TMZ plus 6-AN; 7, TMZ plus 6-AN plus BG; 8, TMZ plus PD128763; 9, TMZ plus PD128763 plus BG.

Finally, as a marker of apoptosis induced cell death, we examined PARP cleavage after cells were treated with these drug combinations at 3 days (FIG. 9). PARP cleavage was observed in SW480 cells after exposure to TMZ alone and TMZ plus BG, but was not seen in HCT116 cells with the same treatment, indicating that the apoptotic process is triggered when $O^6$ mG lesions are repaired by the MMR system. However, PARP cleavage was detected in MMR wild type and deficient cells treated wit TMZ plus either MX or PARP inhibitors.

Example 6

Acute Toxicity of MX

Three mice per group were injected (i.p.) with MX at doses of 1, 2, 4, 6, 10 and 15 mg/kg for the test of acute toxicity. MX was lethal at 15 mg/kg causing death within 10 mins. At 10 mg/kg, mice appeared to have decreased motility but recovered one hour after treatment. Lower doses did not appear toxic.

Example 7

Figure 10:
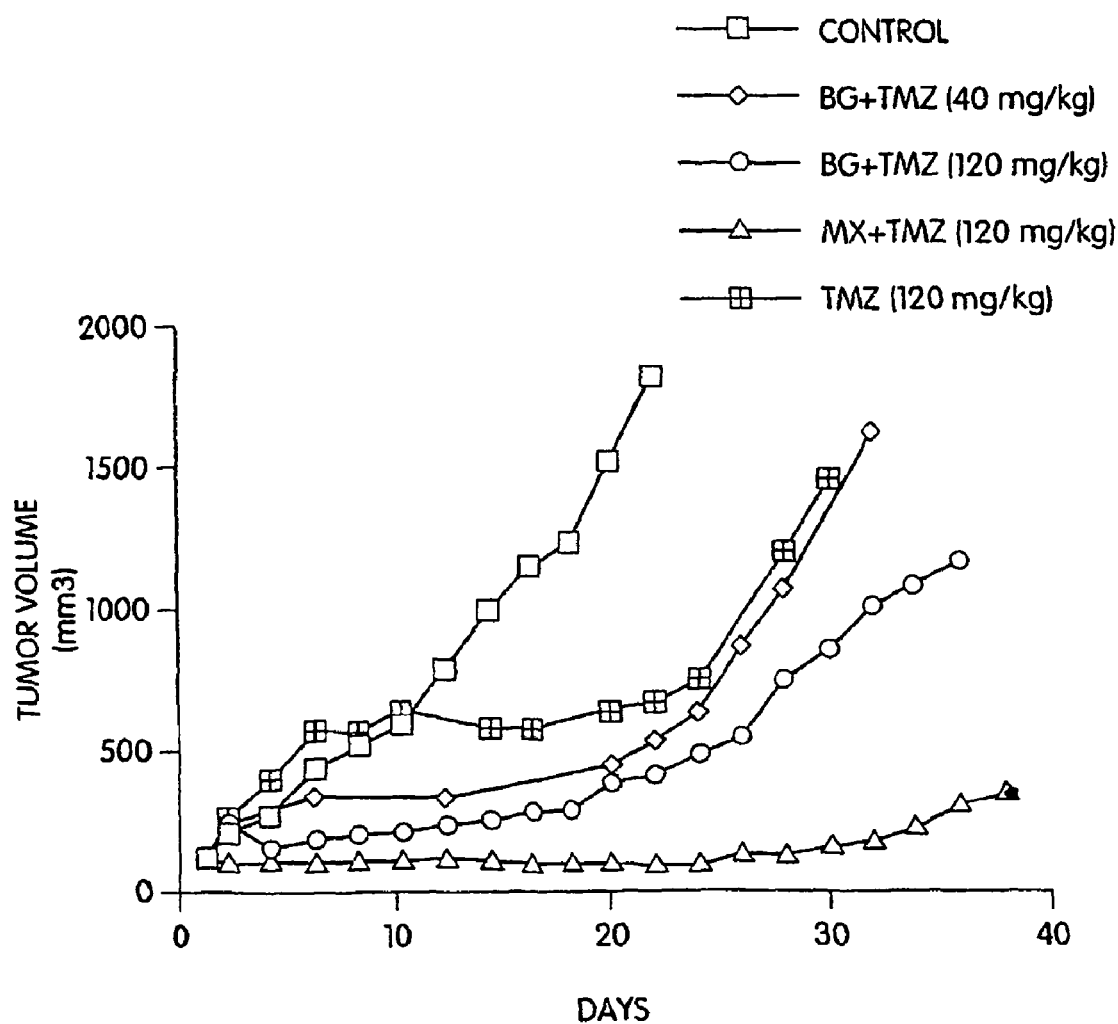
FIG. 10. The effect of MX plus TMZ on growth of SW480 xenograft.

Antitumor Effect of TMZ or TMZ Combined with Either BG or MX on SW480 Tumor Xenograft The response of SW480 xenograft to TMZ alone and combined treatments was shown in FIG. 10 and Table 1. At the highest tolerable does of TMZ, 120 mg/kg, a tumor growth delay of approximately 12 days was noted, indicating that SW480 is sensitive to TMZ. When given 30 mg/kg of BG for one hour prior to 40 mg/kg of TMZ, tumor growth delay was enhanced by BG up to 3-fold. Slightly greater efficacy was seen by combining the BG with high doses of TMZ, but significant weight loss (maximum body weight loss from 26 to 20 g, 23%) and very low leukocyte counts (90% decreased) at day 5 after the last treatment were observed in the mice. In contrast, mice treated with 0.2 mg/kg MX plus 120 mg/kg TMZ had an immediate cessation of tumor growth for 20 days and very slow regrowth of the tumor with tumor growth delays over 40 days (p<0.02). There was no evidence of toxicity to mice with this combined treatment.

TABLE 1

| SW480 xenograft toxicity and tumor response | | | |
|---|---|---|---|
| Group | Doses (mg/kg) | Toxicity (max. BW loss) | Tumor growth delays (Days) |
| TMZ | 120 | 11% (27 ± 1.9 – 24 ± 2.4 g) | 9.3 ± 1.2 |
| MX | 2 | 0% | 2.0 ± 0.5 |
| BG + TMZ | 30/120 | 23% (26 ± 1.5 – 20 ± 0.5 g) | 10.3 ± 2.4 |
| MX + TMZ | 2/120 | 8% (26 ± 1.5 – 24 ± 1.5 g) | 27.0 ± 1.2 |

Example 8

Antitumor Effect of TMZ or TMZ Combined with MX on HCT116 Tumor Xenograft

Figure 11:
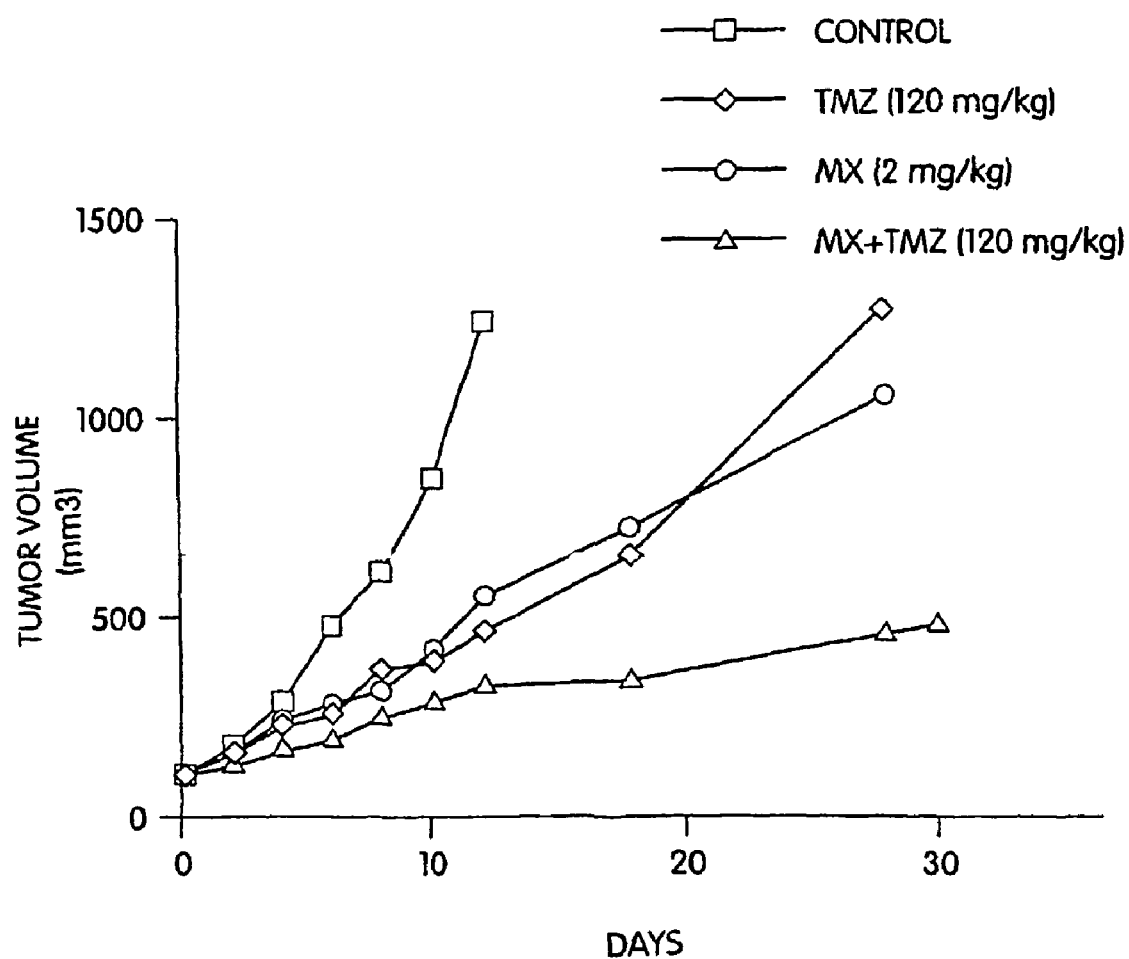
FIG. 11. The effect of MX plus TMZ on growth of HCT116 xenograft.

Mice bearing HCT116 xenograft appeared to be relatively sensitive to all treatment. Body weight loss was observed in all treated groups (Table 2). BG plus TMZ caused 28% body weight loss and toxic death (2 of 5 mice) at 5 days after treatment. As shown in FIG. 11, HCT116 xenografts treated either with TMZ or MX alone had similar growth rate and growth delays of tumor treated with 0.5 mg/kg MX plus 120 mg/kg TMZ were significantly prolonged compared with control tumors (p<0.05).

TABLE 2

HCT116 xenograft toxicity and tumor response

| Group | Doses (mg/kg) | Toxicity (max. BW loss) | Tumor growth delays (Days) |
|---|---|---|---|
| TMZ | 120 | 20.8% (24 ± 1.3 – 19 ± 1.7 g) | 2.5 ± 0.8 |
| MX | 2 | 8.3% (24 ± 1.6 – 22 ± 1.4 g) | 2.2 ± 0.4 |
| BG + TMZ | 30/120 | 28.0% (25 ± 0.8 – 18 ± 0.5 g)* | NA |
| MX + TMZ | 2/120 | 19.2% (26 ± 1.3 – 21 ± 0.4 g) | 17.0 ± 1.2 |

*toxic death: 2/5 mice
NA, did not analyze

Example 9

While an understanding of the underlying mechanism is not necessary to the practice of the invention, and with the understanding that the invention is not to be limited to any particular mechanism, MX potentiates the antitumor effect of methylating agents such as temozolomide (TMZ) both in vitro and in human tumor xenograft models. A nonlimiting hypothesis for the underlying mechanism is that the potentiation is mediated through the known ability of MX to bind apurinic/pyrimidinic (AP) sites in DNA. Thus, in this model, one test of which is provided in the instant example, MX would be hypothesized to be useful in chemotherapy against cancer, and to enhance the therapeutic efficacy of a broad class of agents that produce damaged DNA to generate AP sites, thereby interrupting AP-endonuclease (APE) in the base excision repair pathway.

This example shows that the combination of methoxyamine (MX) and 1,3-bis (chloroethyl) 2-nitrosourea (BCNU, a crosslinking agent known to produce AP sites) is effective in the treatment of cancer, using human tumor xenografts grown in nude mice.

Tumor cells ($5 \times 10^6$) were injected into both flanks of female athymic nude mice, at 6-8 weeks of age. The tumors were measured with calipers using the National Cancer Institute formula: $V = L(mm) \times I^2(mm)/2$, where L is the largest diameter and I is the smallest diameter of the tumor. When the volume of tumor nodules has achieved about 100-150 mm$^3$, tumor-bearing mice were assigned randomly for the control or the treatment groups (3-5 mice/group, 2 tumors/mouse).

Nude mice carrying tumor received a single injection (i.p.) of BCNU (30 mg/kg) or MX (2 mg/kg) combined with BCNU.

Tumor measurements were taken every 3 days. The relative tumor volume ($V/V_0$) was calculated by dividing the measured tumor volume (V) by the initial tumor volume ($V_0$) at day 0. Tumor responses were quantified by tumor regrowth delay. Tumor growth delays were calculated according to the following formula: tumor growth delay=$T_{2x}-C_{2x}$, where $T_{2x}$ and $C_{2x}$ represent the number of days treated and control tumors take to double in size from the day of treatment, respectively.

The human colon cancer cell lines HCT116 (hMLH mut., p53 wt and AGT expressing) and HCT116-Ch3 (having restored MLH1 activity) were inoculated into nude mice at 6-8 weeks of age. At the tumor sizes indicated above, the mice received a single i.p. injection, also as described above.

Figure 12A:
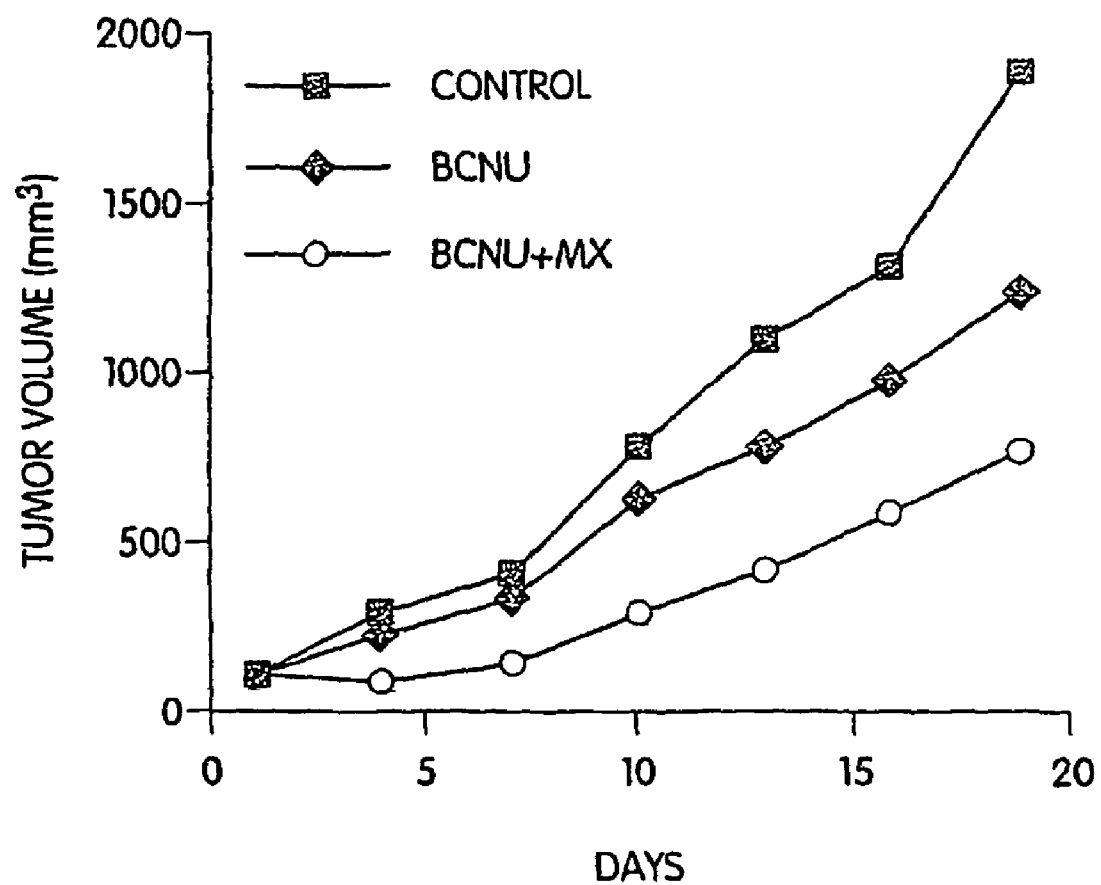
FIG. 12A shows the effects of BCNU alone and BCNU in combination with MX on HCT116 tumors grown in nude mice.
Figure 12B:
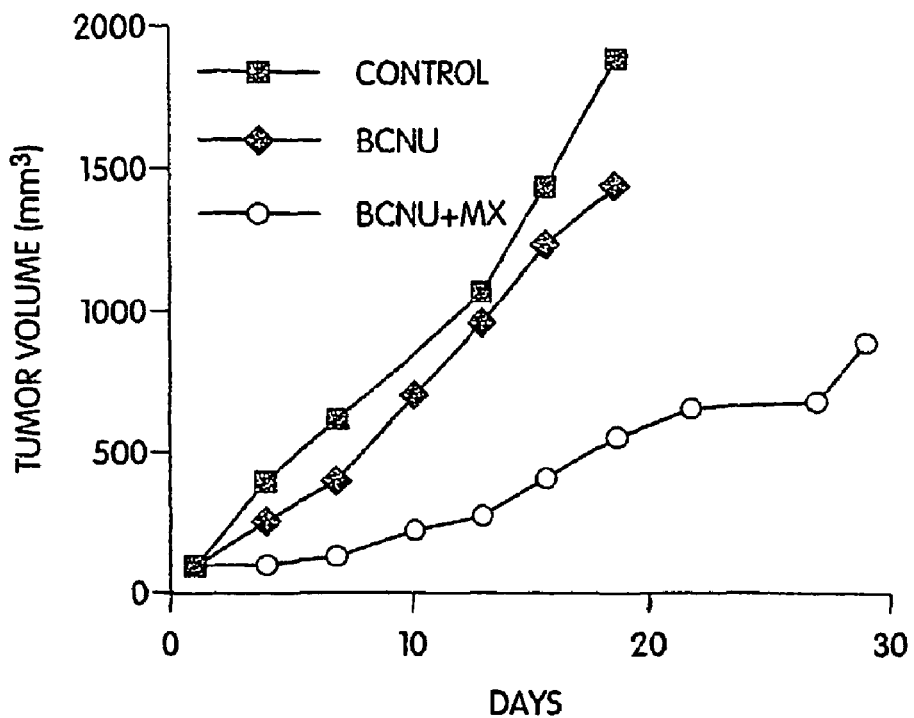
FIG. 12B shows the effects of BCNU alone and BCNU in combination with MX on HCT116-Ch3 tumors grown in nude mice.
Figure 12C:
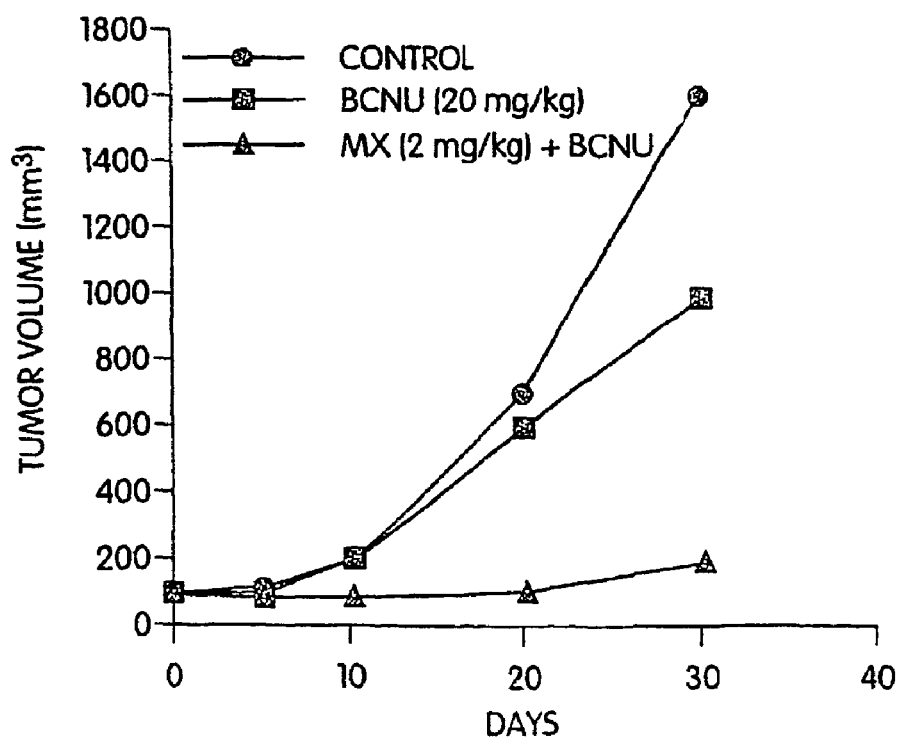
FIG. 12C shows the effects of BCNU alone and BCNU in combination with MX on SW480 tumors grown in nude mice.

The effects on HCT116 tumors are depicted in FIG. 12A. The effects on HCT116-Ch3 are depicted in FIG. 12B. At a dose of 30 mg/kg, BCNU alone had a very mild effect on tumor growth. Combined administration of MX and BCNU produced significant tumor growth inhibition. Tumor growth delays ($T_{2x}$—$C_{2x}$) were 14-16 days in HCT116 tumors (FIG. 12A) and HCT116-Ch3 (FIG. 12B) respectively. A similar result was also observed in SW480 tumor (MMR wt, p53 mutant and AGT expressing). Tumor growth delays were 25 days for the SW480 tumors (FIG. 12C).

Importantly, no systemic toxicity was noted in this combined treatment. In contrast, BCNU (at a dose of 25 mg/kg) combined with O6-benzylguanine (30 mg/kg), an AGT inhibitor being tested in clinical trials, caused toxic death at a 100% rate.

In in vitro studies, the inventors observed that cells exposed to MX combined with BCNU had increased DNA strand breaks (both single strand breaks (SSB) and double strand breaks (DSB) measured by comet assay and pulsed field gel) compared to BCNU alone in these two colon cell lines.

The potentiation of the BCNU-antitumor effect by MX suggests that the impact of the base excision repair pathway is important for BCNU-induced cytotoxicity and that MX-adducted AP sites efficiently interrupt BER leading to cell death. Again, this is only a hypothesis, and the invention is not to be limited to any particular mechanism, and the practice of the invention does not require any knowledge of the underlying mechanism.

Example 10

This example shows the combination of MX and an oxidizing agent for the treatment of cancer.

Again, while the present invention is not limited to any mechanism, BER comprises a ubiquitous series of biochemical pathways for the removal of oxidative damage to the nitrogenous bases in DNA. Initiating proteins of the BER are DNA glycosylases, which hydrolyze the N-glycosylic bond between the deoxyribose sugar moiety and the DNA base, generating AP sites. AP sites can also be generated by spontaneous destabilization of N-glycosyl bonds, particularly after oxidative damage to the bases. The AP sites are the target for MX, resulting in the disruption of BER.

In this experiment, a growth inhibition assay was carried out with $H_2O_2$, an oxidizing agent that mimics the effect of chemotherapeutic agents and radiation. Cells in the exponential phase were plated ($1 \times 10^4$) in 24-well tissue culture plates. After attachment overnight, the cells were incubated with hydrogen peroxide ($H_2O_2$) (0-150 μM) or MX (6 mM) plus $H_2O_2$ for 1 hr. Five days after treatment, the media was discarded, and 100 μl of MTT (5 mg/ml in PBS) was added in 1 ml fresh media to each well for 4 hrs at 37° C. The MTT solution was then removed, and the formazan crystals were dissolved in 200 μl/well of DMSO for 20 min and changes in absorbance were determined at $A_{540nm}$. Percentage growth inhibition was calculated by comparison of the $A_{540nm}$ reading from treated versus control cells. Drug concentrations that resulted in an $IC_{50}$ were determined from the plots of percentage growth inhibition versus the logarithm of the drug concentration.

Figure 13:
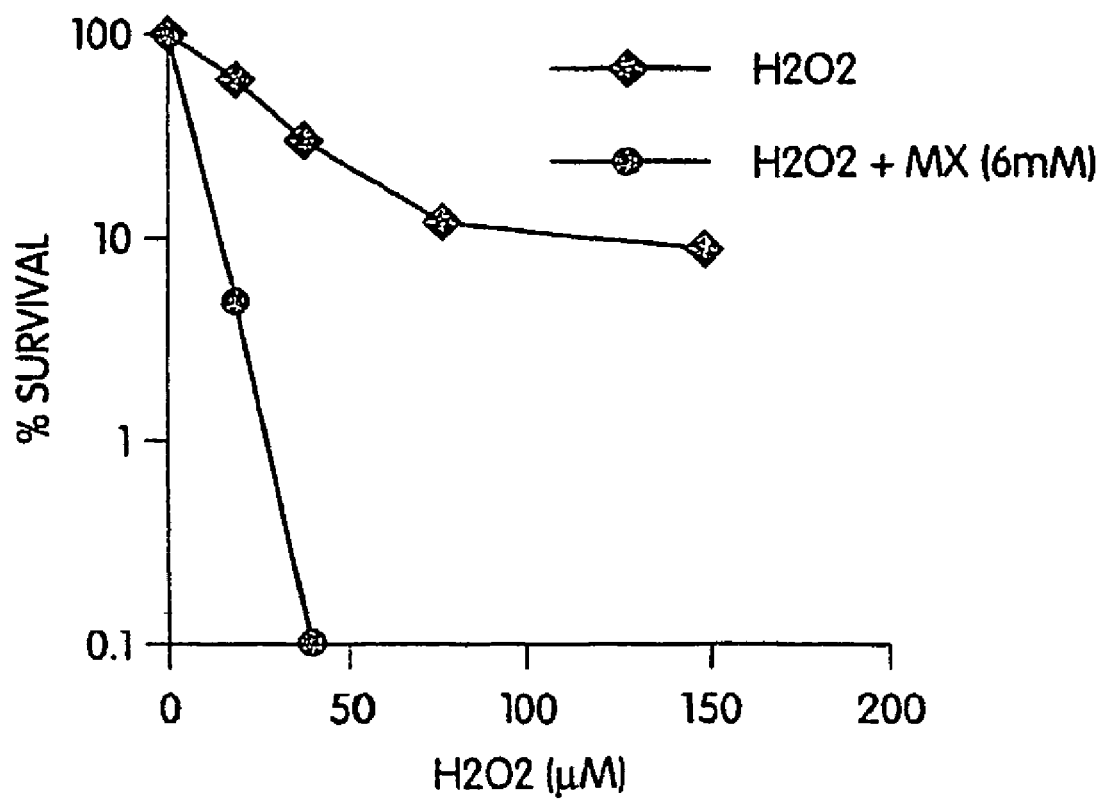
FIG. 13 shows the effects of hydrogen peroxide ($H_2O_2$) alone and $H_2O_2$ in combination with MX on HCT116 cells in a growth inhibition assay.

As shown in FIG. 13, MX results in significantly increased sensitivity of colon cancer cells, HCT116, to killing induced by $H_2O_2$.

This result indicates that MX potentially increases the therapeutic efficacy of a class of anticancer drugs that exert cytotoxicity mediated by oxidative damage in DNA, including but not limited to bleomycin, adriamycin and gamma radiation.

Example 11

This example is directed to combinations of MX with members of a group of agents including, but not limited to hypoxanthine, 5-FU, uracil, IUdR, bleomycin, adriamycin and gamma radiation.

The agents contemplated for combinations with MX in this example are agents which incorporate into DNA and are repaired by BER to form AP sites. Cell-growth inhibition was carried out with HCT116 cells to test MX-potentiated cytotoxicity of iododeoxyuridine (IUdR), which has been recognized as a radiosensitizing agent since the early 1960's. As shown in Table 3, MX increases the killing effect of IUdR (or MX decreases the IC50 of >>60 μM for IUdR alone to 35 μM) in MMR deficient HCT116 cells. This suggests that MX and IUdR combined with radiation therapy will further increase the radiosensitivity of tumor cells.

These experiments demonstrate that a significant enhancement of antitumor effect of TMZ by MX or PARP inhibitors in human colon cancer xenographs with mismatch repair proficiency and deficiency. Therefore, from the above it should be 15 clear that the present invention provides a wide variety of ways to 1) screen for compounds that can potentiate agents useful in the treatment of cancer, 2) provide model systems for the study of cancer treatment by agents that modulate DNA repair mechanisms and, 3) provide treatments for various cancers.

TABLE 3

|  | IUdR | IUdR + MX (6 mM) |
| --- | --- | --- |
| IC 50 (μM) | >>60 | 35 |

Example 12

We observed that MX synergistically increased TMZ-induced cytotoxicity in colon cancer cell lines in both MMR proficient and deficient cells. We hypothesized that TMZ-induced N3 mA and N7 mG DNA adducts generate AP sites as the major targets for MX-potentiation, and thus that the formation and persistence of these DNA adducts (previous study showed that N7 mG half life was 24-48 hrs) become the potential lesions causing cell death in the presence of MX. To test this hypothesis, we treated cells with TMZ+MX (25 mM) for 2 hrs and after washing out drugs, we added low concentrations of MX (2.5 mM) over a 72-hr period in colon cancer cell lines. Cell lines used in this study include SW480 (MMR wt, p53 mut), HCT116 (hMLH1 mut, p53 wt) and HCT15 (hMSH6 mut, p53 mut). We measured AP sites using ARP reagent, noting that ARP and MX compete for binding to AP sites. In SW480 cells, AP sites peaked at 2 h after exposure to TMZ (375 μM, $IC_{50}$ for this cell line) alone and half maximal amounts of AP sites remained at 72 hr. In contrast, lower levels of AP sites were detected (20% of AP sites generated by TMZ alone) over a period of 72 h when cells were treated with MX and TMZ, because MX-adducted AP sites were not recognized by ARP. Thus 80% of AP sites were MX bound. Prolonged exposure to MX apparently results in more MX-AP sites during repair of N7 mG. Moreover, after treatment, 50% of cells accumulate in S phase resulting in increased DNA double strand breaks (DSB) detected by pulsed field gel assay. S phase arrest indicates that DNA replication was blocked by DNA damage, as a consequence of MX-adducted AP sites. The combination of MX and TMZ also induced topoisomerase IIa, whereas topo I levels remained consistent, similar to the effect of the known topo II inhibitor, etoposide. This suggests that MX-AP sites form complexes with topo I and II. It is likely that cytotoxicity elicited by both topoI/II inhibitors and MX-AP sites is due to DNA cleavable complexes, and is thus dependent on the level of topo I/II expression. To exploit this pathway, we added a topo II inhibitor, etoposide (5 μM) to the combination of TMZ and MX and found a remarkable increase in DSB. At 72 hr after treatment, this profound degree of DSB was not noted in cells treated with etoposide and TMZ. MX-AP sites (more than AP sites) thus act as a topo II poison and synergistically enhance the effect of a topo II inhibitor to stabilize cleavable complexes with DNA.

Example 13

As demonstrated above, both $O^6$benzylguanine (BG) and methoxyamine (MX) potentiate the antitumor effect of methylating agents such as temozolomide (TMZ) in human tumor xenografts in nude mice. We observed less myelosuppression and less weight loss using TMZ and MX than using TMZ and BG. These results suggested that MX may not potentiate TMZ cytotoxicity in hematopoietic cells. To test this hypothesis, we conducted in vitro experiments comparing the sensitivity to BG+TMZ and MX+TMZ in colon cancer cell lines with that of mouse bone marrow and human bone marrow cells. We found that BG potentiated TMZ-cytotoxicity up to 14 fold in SW480 tumor cells and 10 fold in human and mouse bone marrow cells respectively. These results indicate the sensitization of BG to TMZ is similar in the two cell types and results from the inactivation of AGT. MX increased TMZ killing by 4 fold in SW480 cells. However, no potentiation of TMZ cytotoxicity was observed with addition of MX in either human CD34+ cells or murine bone marrow progenitor cells when analyzed by colony forming assay. Topoisomerase (Topo) I and Topo II recognize spontaneous AP sites and form stable cleavable complexes. We hypothesized that AP sites formed during repair of TMZ-induced N7 mG and N3 mA adducts would also be recognized by Topo I and Topo II. However since Base Excision Repair [BER] is normally quite efficient, we further hypothesized that the impact of Topo I and Topo II would be most important after MX inhibition of BER; increased unrepaired MX adducted AP sites should increase Topo mediated strand breaks and apoptosis. Therefore, potentiation of TMZ cytotoxicity by MX would be dependent on Topo I and II. We found that levels of topoisomerases I and II were much higher (>20-fold) in human tumor cell lines than in either human CD34+ or murine bone marrow progenitor cells. Thus, we propose that MX does not potentiate TMZ toxicity in hematopoietic progenitors because these cells express low levels of Topo I and II. Lack of Topo I and II results in less cleavable complex formation, fewer double strand DNA breaks, and less apoptosis. We predict a better therapeutic index for the combination of MX/TMZ than observed with BG/TMZ because of the relative overexpression of topoisomerases I and II in malignant cells compared to marrow progenitors.

Example 14

Figures 14A, 14B:
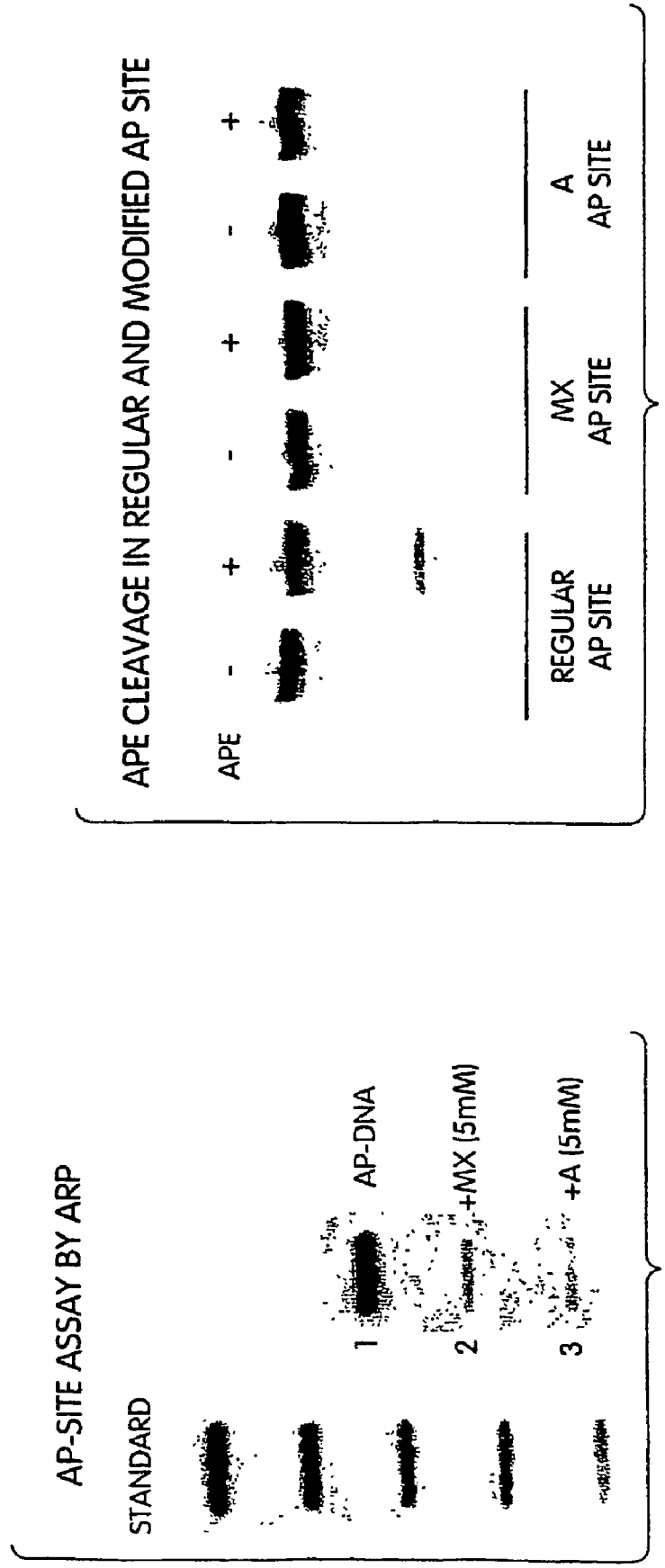
FIG. 14 shows that Compound A and MX have the same reactivity to AP sites. (A) Binding of A or MX to AP sites as assayed by ARP. (B) APE cleavage assays in regular and modified AP sites.
Figure 15:
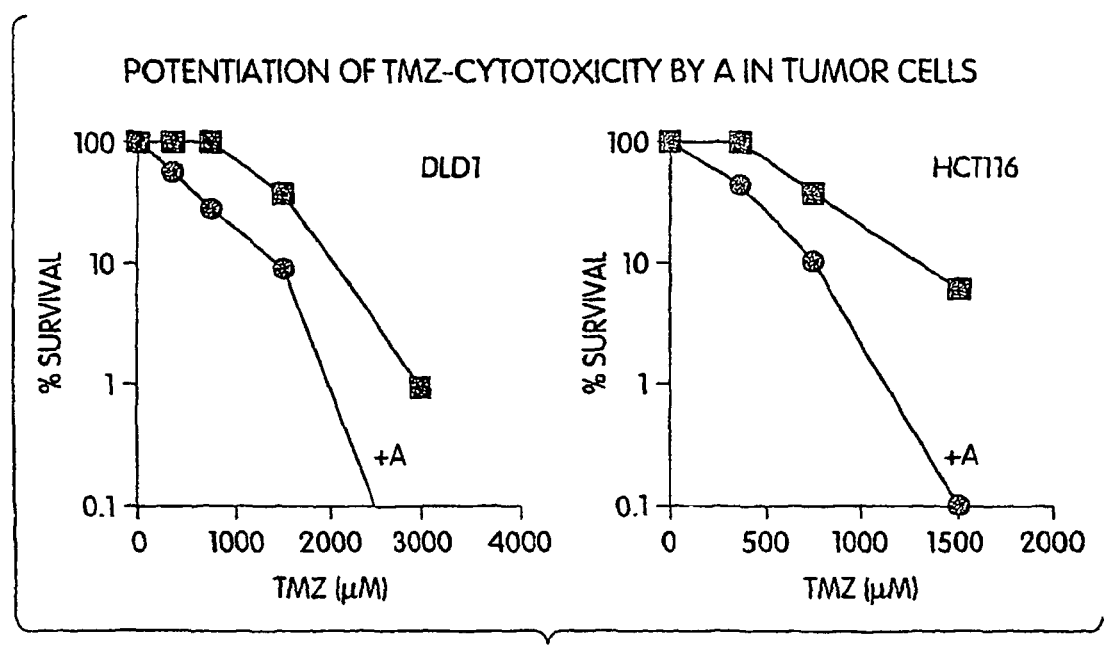
FIG. 15 shows that A potentiates TMZ cytotoxicity in two tumor cells: DLD1 cells and HCT116 cells.

The results that methoxyamine (MX) potentiated the cytotoxic effect of temozolomide (TMZ) and BCNU indicated that molecules targeting abasic lesions in DNA are important approach to improve chemotherapeutic efficacy of alkylating agents. On the basis of a similar molecular reaction to MX, (e.g., a primary amine with the carbonyl group of the abasic site), we tested whether a compound (Compound A) would have the ability to bind to AP site generated by TMZ and enhance the killing effect of TMZ. A has a MX-like structure to bind to AP site and also has fluorescence molecules to provide a signal for direct detection of modified AP sites using cellular image. We found that this compound was able to bind to AP sites assayed with aldehyde-reactive probe (ARP) that competitively binds to the aldehyde group of AP site. A-modified AP sites were refractory to cleavage of APE, suggesting that it can block base excision repair (BER) pathway by inhibiting repair of AP sites. Cellular image showed 30% of cells with fluorescent signal that was located in nuclear at 2 hr after treatments with TMZ plus A. In contrast, cells treated with A alone had no visualized fluorescence signal. This data suggest that A specifically binds to AP sites in DNA. In in vitro study, we observed A at non-toxic concentrations (1 mM) sensitized cells to TMZ-cytotoxicity 2-3-fold. In a xenograft model, A (2 mg/kg) combined with TMZ (80 mg/kg) enhanced anti-tumor effect in HCT116 and DLD1, two xenograft tumors with very high resistance to TMZ. Tumor growth delays were 13 days in HCT116 and 12 days in DLD1 treated with the combination of A and TMZ over TMZ alone. Thus, A has a similar effect to MX on interruption of BER and can potentiate chemotherapeutic agents such as alkylating agents. Results are depicted in FIGS. 14-16.

Example 15

The experiments above suggest that MX synergistically increased TMZ-induced cytotoxicity in colon cancer with either MMR proficiency or deficiency as a result of TMZ-AP sites generated from induced N3 mA and N7 mG DNA adducts. AP sites are the major targets being responsible for MX-induced potentiation of alkylating therapeutic agents.

In vivo studies showed that the treatment with MX and TMZ induced extremely high frequencies of chromosomal aberration (present in over 90% of chromosomes) in tumor xenografts after three daily treatments, including aneuploidy, sister chromosome exchange, and severe DNA breakage. The single strand and double strand DNA breaks (FIG. 4) are visible at metaphase. It is well known that topoisomerases are essential enzymes that interconvert topological forms of DNA for transcription, DNA replication, and chromosome segregation, and it has been demonstrated that AP sites, when located within a topoisomerase I/II DNA cleavage site, act as topoisomerase poisons and stimulate enzyme-mediated DNA scission. Therefore, these results suggest that topoisomerases may be involved in the induction of DNA aberration induced by TMZ and MX. We hypothesize that MX-AP sites act as topo II poisons to abort cleavage and ligation reaction of topo II (higher levels of endogenous topoisomerase II or) and induced levels of topoisomerase II will promote topo II mediated-DNA cleavage resulting in accumulation of DNA double-strand breaks. To test this hypothesis, we developed a combined treatment with TMZ, MX, and a topoII inhibitor, etoposide, in colon cancer cell lines.

Figure 17:
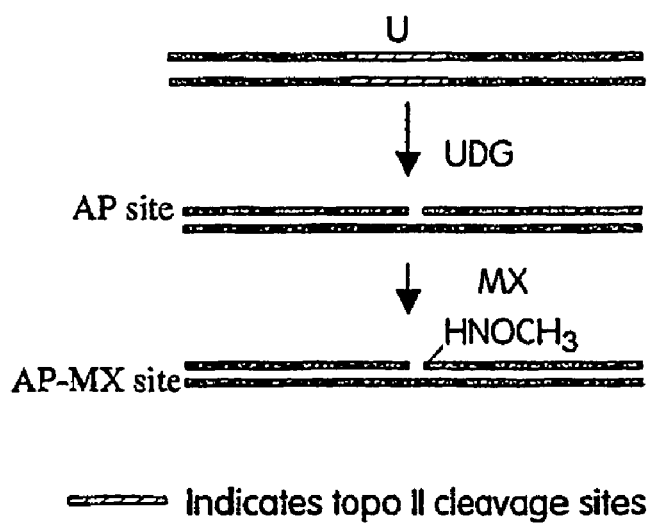
FIG. 17 shows a schematic diagram of the preparation of DNA substrates with regular AP sites or MX-AP sites.

Methods:

Analysis of the effect of AP site or MX-AP site on topoisomerase II-mediated DNA cleavage. A position-specific apurinic site was incorporated by replacing a single nucleoside with deoxyuridine at a topoisomerase II cleavage site and then removing the uracil base with uracil-DNA glycosylase, generating AP sites that further are incubated with MX to produce MX-AP sites (FIG. 17).

Measurement of DNA double-strand breaks by pulsed-field gel electrophoresis (PFGE). A PFGE procedure was used to visualize induction of DSBs. Log-phase cultures were exposed to the DNA-damaging agents for 15 min at 37° C., then cells were harvested by scraping into ice-cold PBS. Cells were centrifuged and washed twice with ice-cold PBS. The cells were resuspended in an appropriate volume of PBS, and an equal volume of 1.5% low melting point agarose in TAE buffer to yield $5\times10^6$ cells per 75 μl plug. The plugs were allowed to solidify on ice, then were incubated at 50° C. overnight in approximately 5 ml of a lysis solution of 1% sarcosyl, 100 mM EDTA, 10 mM Tris-HCl, pH 7.5, and 100 μg/ml of proteinase K. The following day, the lysis solution was replaced with TE buffer (10 mM Tris-HCl, pH 7.5 with 50 mM EDTA). Plugs were inserted into the wells of a 0.7% agarose gel. The gel was run using a clamped homogeneous electric field (CHEF) Mapper XA system (BioRad) using the 180° field inversion gel electrophoresis (FIGE) program, at electrophoresis conditions that can achieve the best sensitivity in detection of DNA DSB and good resolution in the megabase size region. After electrophoresis, the gel was stained with ethidium bromide to visualize DNA.

Median Effect Analysis (MEA). MEA was used to determine the dose-response interactions between Docetaxel and Rebecomycine. Drugs were combined at the ratio of the $IC_{50}$ values for either Docetaxel alone or Rebecomycine alone as determined by survival/concentration curves. The combination was compared to the cytotoxicity of each drug alone in every experiment. The combination index (CI) was determined from survival fractions at increasing levels of cell killing, using analysis of multiple drug interaction program (Biosoft, Cambridge, United Kingdom) developed based on a method of Chou and Talalay. CI values of less than or greater than 1 indicate synergy and antagonism, respectively, whereas a CI value of 1 indicates additivity of the drugs.

Figure 18:
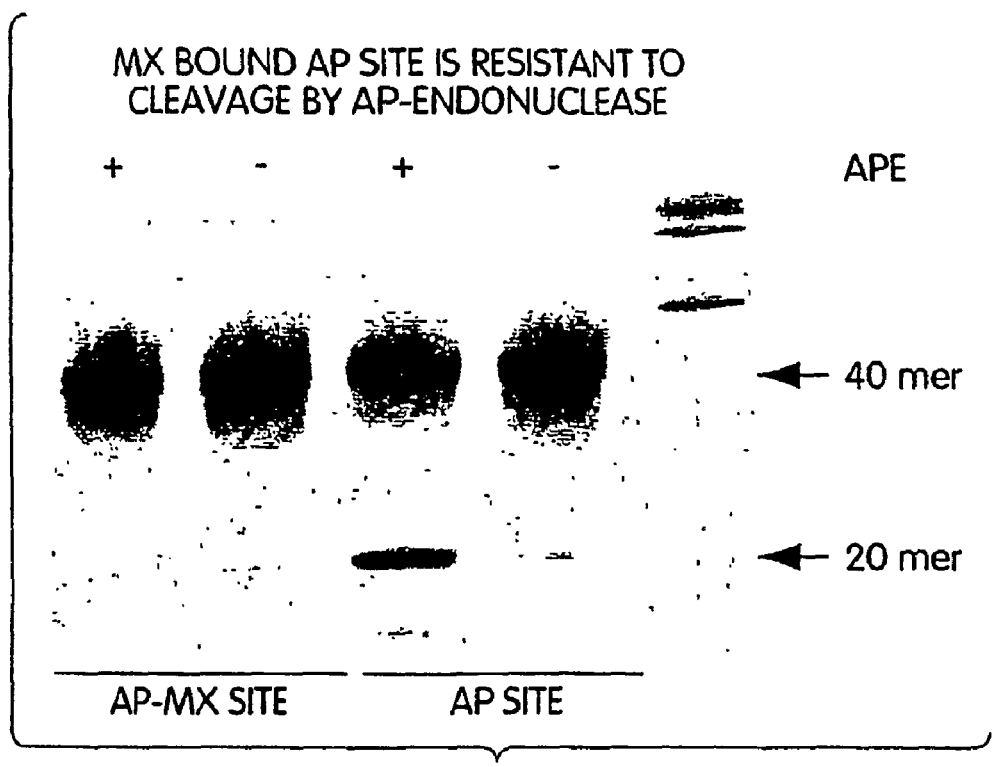
FIG. 18 shows that MX-bound AP sites are resistant to cleavage by AP-endonuclease (APE).
Figure 19:
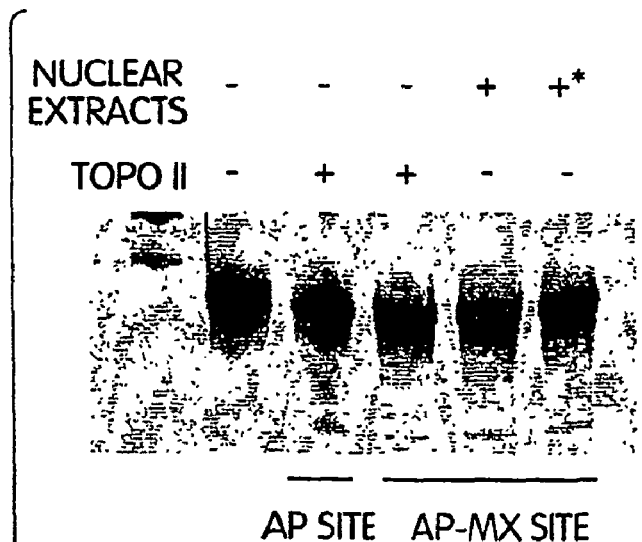
FIG. 19 shows topo II-mediated DNA cleavage in oligonucleotides containing a topo II cleavage site, in the presence or absence of etoposide.

Results:

First, we examined whether APE has a differential effect between regular AP sites and MX-AP sites located in a position specific site for topo II cleavage. Results show that APE is able to cleave regular AP sites rather than MX-bound AP sites (FIG. 18), however, both AP and MX-AP sites are cleaved by topoisomerase II, indicating MX-AP sites are able to stimulate topoisomerase II-mediated DNA cleavage. The cleavage is also observed after incubation of DNA substrates with nuclear extract of colon cancer cells, even having pretreatment with etoposide, indicating that MX-AP site-stimulated Topo II cleavage is independent of the presence of etoposide (FIG. 19).

We predicted that after treatment with MX and TMZ to generate MX-AP sites, the DNA lesion is able to trap topo II in cleavage complex, whereas etoposide interacts with topo II to form Topo II-DNA cleavage complexes. We thus suspected that they all convert topo II into a physiological toxin that creates DNA double strand breaks, thus, synergistically inducing cell death.

To exploit this pathway, we added a topo II inhibitor, etoposide (5 μM), to the combination of TMZ and MX and found a remarkable increase in DSB. Even at 72 hr after treatment, this profound degree of DSB was noted in cells treated with etopside, TMZ, and MX (FIG. 20).

Figure 21A:
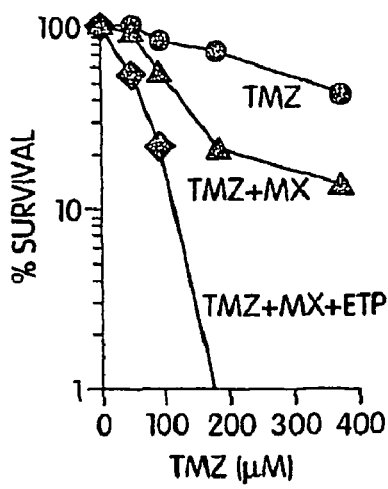
FIG. 21 shows colony survival assays in the cell line SW480 after either individual treatment with TMZ (A or D) or etoposide (C), or combination treatment with TMZ and MX (A), TMZ, MX and etoposide (A), or TMZ and etoposide (D). The synergy analysis of the interaction among TMZ, MX, and etoposide is indicated by the combination index (CI) (shown in B and E).
Figure 21B:
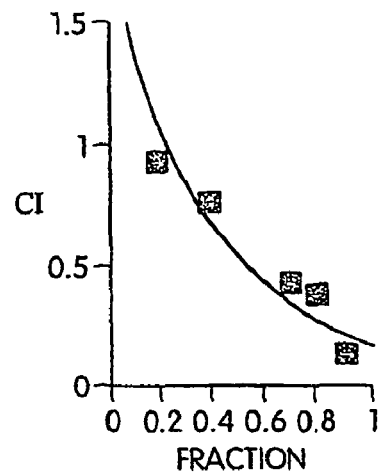
Figure 21C:
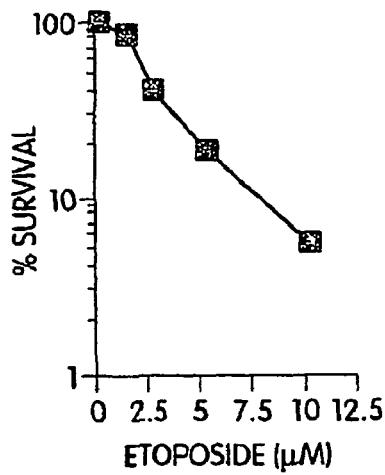
Figure 21D:
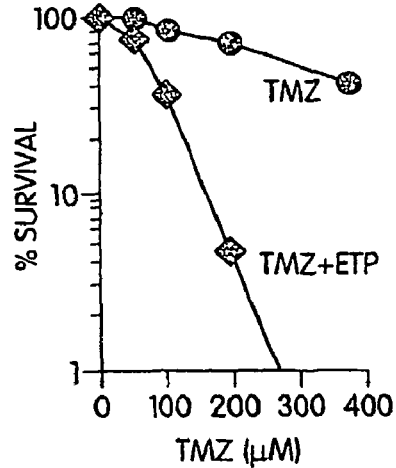
Figure 21E:
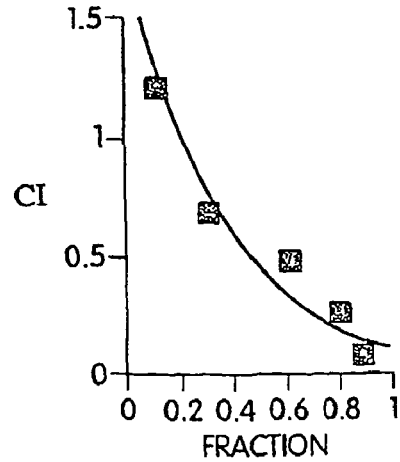

Colony survival assay shows that the combination treatment increased the cell-killing effect (FIG. 21A), and evidenced a synergistic interaction between TMZ, MX, and etoposide (FIG. 21B) when analyzed with multiple drug interaction program (based on the method of Chou and Talalay: combination index values of less than or greater than 1 indicate synergy and antagonism, whereas a combination index value of 1 indicates additivity of the drugs).

In summary, MX-AP sites (to a greater degree than AP sites) act as topo II poisons and synergistically enhance the effect of a topo II inhibitor, etoposide, by stabilizing cleavable complexes with DNA and increasing DNA double-strand breaks, leading to increased cell death.

We claim:

1. A method for potentiating a therapeutic effect of an anticancer agent that induces formation of AP sites in cancer cells of a patient, comprising administering to a patient with cancer an anticancer agent that induces formation of AP sites in cancer cells of the patient and an amount of a base excision repair (BER) inhibitor that is effective to potentiate the cytotoxicity of the anticancer agent to the cancer cells, the BER inhibitor comprising an AP endonuclease inhibitor, the AP endonuclease inhibitor comprising a small molecule compound having a primary amine group that binds to an aldehyde group of the AP site and prevents AP endonuclease-mediated cleavage of phosphodiester bonds.

2. The method of claim 1, wherein said anticancer agent is selected from a DNA oxidizing agent, ultraviolet radiation, a DNA intercalating agent, a radiosensitizing agent, a cross-linking agent, and an alkylating agent.

3. The method of claim 2, wherein said AP endonuclease inhibitor is selected from methoxyamine and a compound having a structure of Formula I:

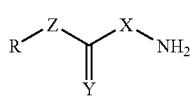

Formula I wherein X is O or NH,
Y is O, S, or NH,
Z is absent or represents O, S, or NH, and
R represents a hydrogen or a hydrocarbon moiety,
and pharmaceutically acceptable salts thereof.

4. The method of claim 2, wherein said anticancer agent is an alkylating agent.

5. The method of claim 4, wherein said AP endonuclease inhibitor is selected from methoxyamine and a compound having a structure of Formula I:

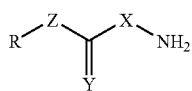

Formula I wherein X is O or NH,
Y is O, S, or NH,
Z is absent or represents O, S, or NH, and
R represents a hydrogen or a hydrocarbon moiety,
and pharmaceutically acceptable salts thereof.

6. The method of claim 1, wherein the amount of anticancer agent is subtherapeutic when administered in the absence of the base excision repair inhibitor.

7. The method of claim 1, the AP endonuclease inhibitor is selected from group consisting of methoxyamine; O-benzylohydroxylamine; ethyl aminooxyacetate; aminooxyacetic acid; ethyl aminooxyacetate; H$_2$NOCHMeCO$_2$H; carboxymethoxyamine; aminooxyacetic acid; HN=C(NH$_2$)SCH$_2$CH$_2$ONH$_2$; H$_2$NO(CH$_2$)$_3$SC(NH$_2$)=NH; MeOC(O)CH(NH$_2$)CH$_2$ONH$_2$; H$_2$NOCH$_2$CH(NH$_2$)CO$_2$H; canaline; H$_2$NO(CH$_2$)$_4$ONH$_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene) dihydroxylamine; O,O'-(p-phenylenedimethylene)dihydroxylamine; H$_2$C=CHCH$_2$ONH$_2$; H$_2$NO(CH$_2$)$_4$OH$_2$; H$_3$C—(CH$_2$)$_{15}$—O—NH$_2$, 2,2'-(1,2-ethanediyl)bis(3-aminooxy)butenedioic acid dimethyl diethyl ester;

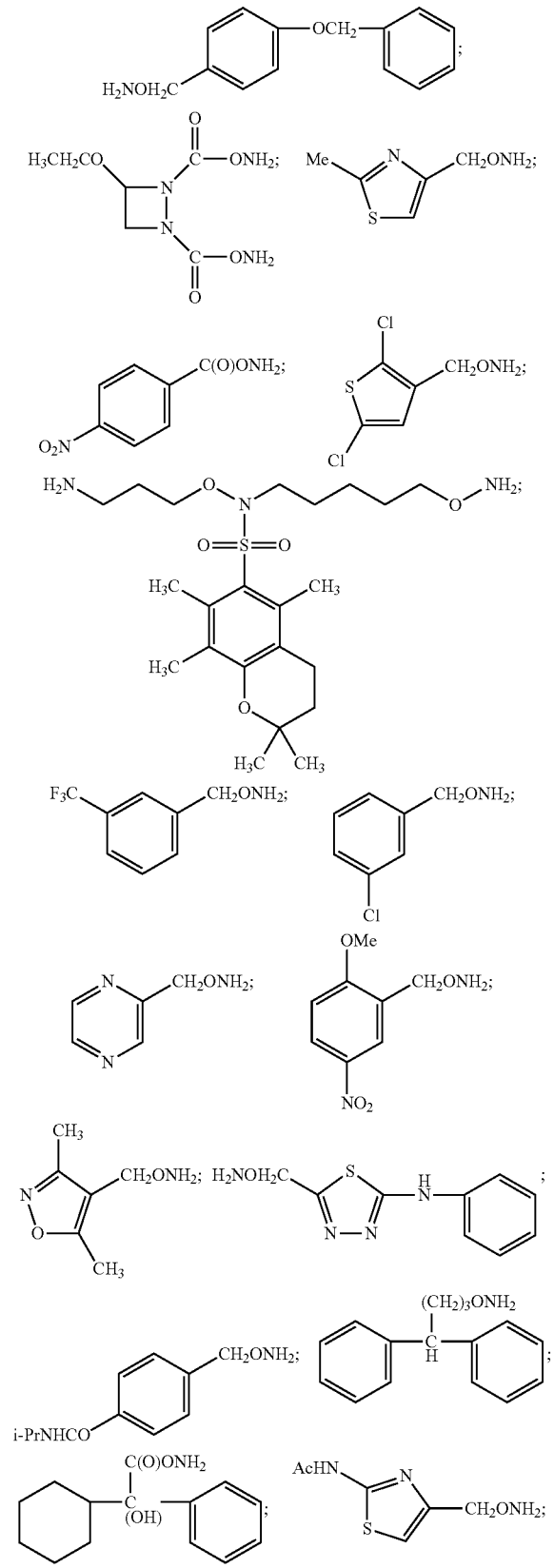

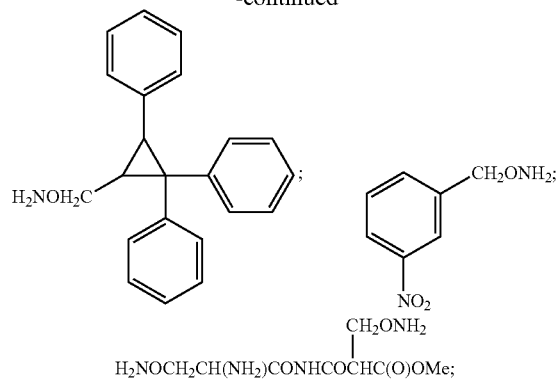

H₂NOCH₂CH(NH₂)CONHCOCHC(O)OMe;

a compound having a structure of Formula I:

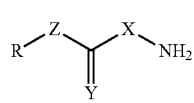

Formula I wherein X is O or NH,
Y is O, S, or NH,
Z is absent or represents O, S, or NH, and
R represents a hydrogen or a hydrocarbon moiety,
and pharmaceutically acceptable salts thereof.

8. A method for potentiating a therapeutic effect of an anticancer agent that induces formation of AP sites in cancer cells of a patient, comprising administering to a patient with cancer an anticancer agent that induces formation of AP sites in cancer cells of the patient and an amount of a base excision repair (BER) inhibitor that is effective to potentiate the cytotoxicity of the anticancer agent to the cancer cells, the BER inhibitor comprising an AP endonuclease inhibitor selected from the group consisting of methoxyamine; O-benzylohydroxylamine; ethyl aminooxyacetate; aminooxyacetic acid; ethyl aminooxyacetate; H₂NOCHMeCO₂H; carboxymethoxyamine; aminooxyacetic acid; HN=C(NH₂)SCH₂CH₂ONH₂; H₂NO(CH₂)₃SC(NH₂)=NH; MeOC(O)CH(NH₂)CH₂ONH₂; H₂NOCH₂CH(NH₂)CO₂H; canaline; H₂NO(CH₂)₄ONH₂; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; H₂C=CHCH₂ONH₂; H₂NO(CH₂)₄ONH₂; H₃C—(CH₂)₁₅—O—NH₂, 2,2'-(1,2-ethanediyl)bis(3-aminooxy)butenedioic acid dimethyl diethyl ester;

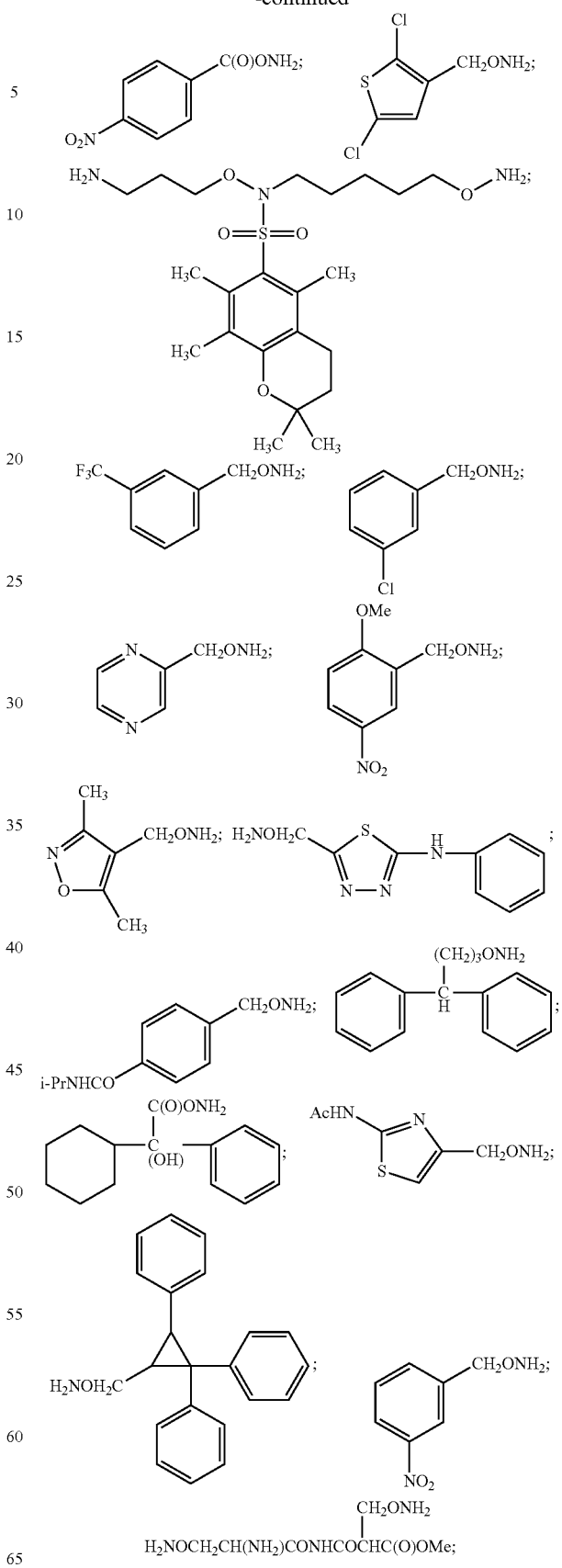

a compound having a structure of Formula I:

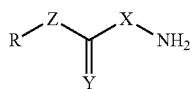

Formula I wherein X is O or NH,
Y is O, S, or NH,
Z is absent or represents O, S, or NH, and
R represents a hydrogen or a hydrocarbon moiety,
and pharmaceutically acceptable salts thereof.

9. The method of claim 8, wherein said AP endonuclease inhibitor is selected from methoxyamine and a compound having a structure of Formula I:

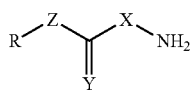

Formula I wherein X is O or NH,
Y is O, S, or NH,
Z is absent or represents O, S, or NH, and
R represents a hydrogen or a hydrocarbon moiety,
and pharmaceutically acceptable salts thereof.

10. The method of claim 8, wherein said anticancer agent is selected from a DNA oxidizing agent, ultraviolet radiation, a DNA intercalating agent, a radiosensitizing agent, a cross-linking agent, and an alkylating agent.

11. The method of claim 8, wherein said anticancer agent is an alkylating agent.

12. The method of claim 8, wherein the amount of anticancer agent is subtherapeutic when administered in the absence of the base excision repair inhibitor.

* * * * *